US008993837B2

(12) United States Patent
Albert et al.

(10) Patent No.: US 8,993,837 B2
(45) Date of Patent: Mar. 31, 2015

(54) CHIMERIC PROMOTERS AND METHODS OF USE

(75) Inventors: Henrik Albert, Alameda, CA (US); Linda A. Castle, Mountain View, CA (US); Jian Lu, Union City, CA (US); Yumin Tao, Urbandale, IA (US)

(73) Assignee: Pioneer Hi-Bred International, Inc, Johnston, IA (US)

( * ) Notice: Subject to any disclaimer, the term of this patent is extended or adjusted under 35 U.S.C. 154(b) by 617 days.

(21) Appl. No.: 13/209,017

(22) Filed: Aug. 12, 2011

(65) Prior Publication Data

US 2012/0042414 A1 Feb. 16, 2012

Related U.S. Application Data

(60) Provisional application No. 61/401,456, filed on Aug. 13, 2010, provisional application No. 61/393,507, filed on Oct. 15, 2010, provisional application No. 61/501,042, filed on Jun. 24, 2011.

(51) Int. Cl.

| | |
|---|---|
| ***C12N 15/82*** | (2006.01) |
| ***A01H 5/00*** | (2006.01) |
| ***C12N 15/00*** | (2006.01) |
| ***C12N 5/10*** | (2006.01) |
| ***C07H 21/04*** | (2006.01) |
| ***C12N 9/02*** | (2006.01) |

(52) U.S. Cl.

CPC .......... *C12N 15/8274* (2013.01); *C12N 9/0069* (2013.01); *C12N 15/8221* (2013.01)

USPC ........... 800/278; 800/298; 800/306; 800/312; 800/314; 800/320; 800/320.1; 800/320.2; 800/320.3; 800/322; 435/468; 435/320.1; 435/419; 536/24.1

(58) Field of Classification Search

None

See application file for complete search history.

(56) References Cited

U.S. PATENT DOCUMENTS

| | | | |
|---|---|---|---|
| 6,072,050 | A | 6/2000 | Bowen et al. |
| 6,118,050 | A | 9/2000 | Sturner et al. |
| 6,268,549 | B1 | 7/2001 | Sailland et al. |
| 6,555,673 | B1 | 4/2003 | Bowen et al. |
| 6,768,044 | B1 | 7/2004 | Boudec et al. |
| 7,312,379 | B2 | 12/2007 | Andrews et al. |
| 2003/0066102 | A1 | 4/2003 | Maxwell et al. |
| 2005/0193445 | A1 | 9/2005 | Cahoon et al. |
| 2010/0197503 | A1 | 8/2010 | Hawkes et al. |

FOREIGN PATENT DOCUMENTS

| | | | |
|---|---|---|---|
| WO | WO 97/47756 | A1 | 12/1997 |
| WO | WO 97/49816 | A1 | 12/1997 |
| WO | WO99/43838 | * | 9/1999 |
| WO | WO 00/32757 | A2 | 6/2000 |
| WO | WO 02/46387 | A2 | 6/2002 |

OTHER PUBLICATIONS

Falk_J Plant Physiol 159_1245_2002.*

Potenza_In Vitro Cell Dev Biol Plant_40_1_2004.*

Database EMBL—Accession No. AAA29168, "Soybean 4-hydroxyphenylpyruvate dioxygenase cDNA," 2000, 1 page.

Kiran, K., et al., "The TATA-Box Sequence in the Basal Promoter Contributes to Determining Light-Dependent Gene Expression in Plants," Plant Physiology, 2006, vol. 142(1), pp. 364-376.

Lodhi, N. et al., "Interactions between upstream and core promoter sequences determine gene expression and nucleosome positioning in tobacco PR-la promoter," Biochimica et Biophysica Acta, 2008, vol. 1779(10), pp. 634-644.

Rushton, P., et al., "Synthetic Plant Promoters Containing Defined Regulatory Elements Provide Novel Insights into Pathogen—and Wound-Induced Signaling," The Plant Cell, 2002, vol. 14(4), pp. 749-762.

U.S. Appl. No. 13/208,966, entitled *Compositions And Methods Comprising Sequences Having Hydroxyphenylpyruvate Dioxygenase (HPPD) Activity*, filed Aug. 12, 2011.

U.S. Appl. No. 13/208,960, entitled *Methods and Compositions for Targeting Sequences of Interest to the Chloroplast*, filed Aug. 12, 2011.

Vedel, et al., "Promoting the promoter," *Plant Science*, 2011,vol. 180(2), pp. 182-189 (Abstract Only).

* cited by examiner

*Primary Examiner* — Medina A Ibrahim
*Assistant Examiner* — Russell Boggs
(74) *Attorney, Agent, or Firm* — Ballard Spahr LLP

(57) ABSTRACT

Compositions and methods comprising promoters from the 4-hydroxyphenylpyruvate dioxygenase (HPPD) gene and active variants and fragments thereof, as well as chimeric promoters employing regulatory regions of the HPPD promoters are provided. Further provided are expression cassettes and plants comprising the various promoters disclosed herein operably linked to a polynucleotide of interest. Methods employing the various promoters described herein to modulate the expression of polynucleotides of interest are further provided.

46 Claims, 11 Drawing Sheets

Figure 1.

TCAAGATGAGGATGATCCTCTTGTTAGTGTGTTTTGATTGTTCTTTATAGTTTATACCTAATTTTATCTAT
ATAAGCTTATTAAATTAAATTTATGTGCAATAGTGACCCCTGATCTTCTGTAATTATCATTCAATAGCTGT
AGTCATTTTGTTTCCAATTGTAACCGTAGCCAAGATGTACGGTGGCATAAACCTTGGAGATATTTTGTTCT
CTCTTCCCTTCATAGAGGACAACCTTCATGTAATGGACATACTAACGACAATTAAATTTATTTATCATTTTA
AAAGATTAAATATTTTTTTCTTAAATTATTCCTGTGCTTTAAAATTCTTAACAGAAAATTTAAAATTAGACA
TTTGTACCATTAGAGAAAAACTGTGGGACTCATTTGTTTATTAGATTATTTCAGCTAGCAACTGACTCTCT
TGTACATTTCATTTTTACATTCCTTTAATTATGCATCATTAACAGTAGTAGATTGCATCTCTTAAAAAAAA
AATTAGATTGCAGTATTGCCTTGGAAATATGGAATTACAATGTCAAAATATTTTAACGAATAACGATGCGT
AGCTTAAAGTTCAAGACACAATTTTAACGTTATATAGTGCATCAATGTTTGAAATTTTAGTGTATAAATAA
CGTATTTTTGATAATATTTTTTACACAACAATCCTCTTAAATTTTCTTATCTTATTTCATTTAACCGTTCT
CTTAAATTGTCTTATCTTTTTTACACACAAATGAATCCCAATAAACATGGTTGGGATTTATTTGAGTTCTT
AACTTTAGGAACCAAATATATAATAATTTTTTTTTTTTAAAAAAAAAGAAGATAAATATAGAAGAAAAGGA
TGTGATAAAGGCAAGAGAAGCGTGTGAACAAGAGAGAGACGAATCTAGGTGGATTTGACGTACGTTGAATG
AATGTTGAATATAAGTAATAACGCTGAGGCTGTAGGTGTGGGTAATAAAAAAAGAGAGAAGCCGCATCAAC
ATCATCCAATATATGGACGTTAAAAGAGCGTCGTAATCCATTTCCATTTCTCATCTATCTTCACTTCCTCG
TCCTCATCCTCATCCACCTATTCTCAACCCAGACGCAATGCCCATGTACACTCCATCACTCTCCGCACCCT
CCTCCAATCACATTCAACCAAGTGTCACACTCCCCTTATATATCACAACCACCAAGCTCAATCTCAAGCAG
CAGCATCACACCACACCAATG

HPPD Promoters

| Native Soy HPPD Promoter | | Experimental Name |
|---|---|---|
| T1 T4 T5 T2 T3 | SEQ ID NO: 1 | GmHPPD PRO |
| T1 T4 T5 T2 | SEQ ID NO: 4 | SHP103C |
| T1 T4 T5 | SEQ ID NO: 11 | SHP110C |
| T1 T4 | SEQ ID NO: 20 | SHP0C |
| T1 | SEQ ID NO: 3 | SHP102C |
|  | SEQ ID NO: 2 | SHP101C |
| T1 T4 T5 T2 T3 | SEQ ID NO: 76 | SHP122C |

- ■ TATA1 (T1)
- ■ TATA2 (T2)
- ▨ TATA3 (T3)
- ▦ TATA4 (T4)
- ▒ TATA5 (T5)
- ∗ Point mutations

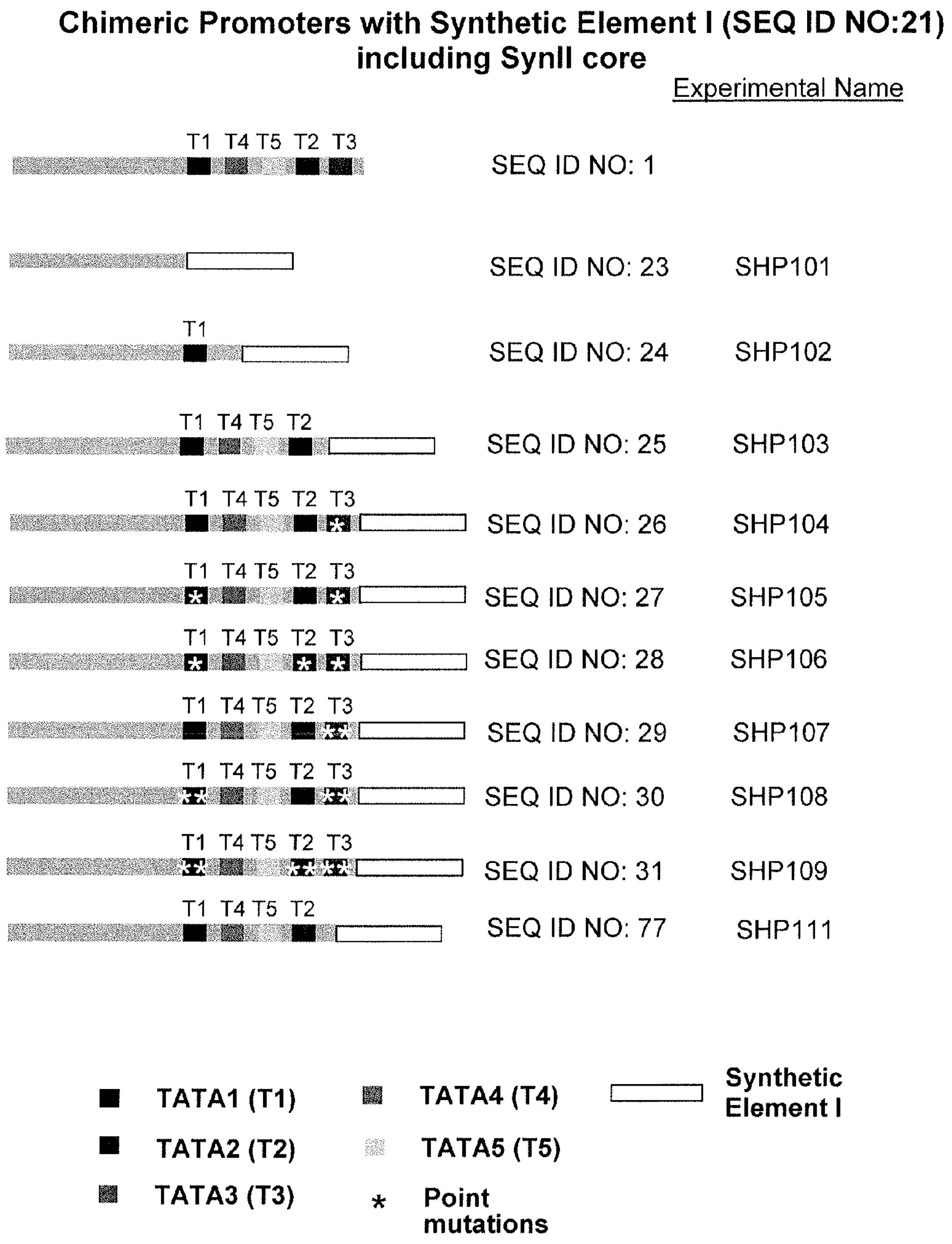

Figure 8.

Chimeric Promoters with Synthetic Element I (SEQ ID NO:21) including SynII core Experimental Name

| Diagram | SEQ ID | Name |
|---|---|---|
| T1 T4 T5 T2 T3 | SEQ ID NO: 1 | |
| | SEQ ID NO: 23 | SHP101 |
| T1 | SEQ ID NO: 24 | SHP102 |
| T1 T4 T5 T2 | SEQ ID NO: 25 | SHP103 |
| T1 T4 T5 T2 T3 | SEQ ID NO: 26 | SHP104 |
| T1 T4 T5 T2 T3 | SEQ ID NO: 27 | SHP105 |
| T1 T4 T5 T2 T3 | SEQ ID NO: 28 | SHP106 |
| T1 T4 T5 T2 T3 | SEQ ID NO: 29 | SHP107 |
| T1 T4 T5 T2 T3 | SEQ ID NO: 30 | SHP108 |
| T1 T4 T5 T2 T3 | SEQ ID NO: 31 | SHP109 |
| T1 T4 T5 T2 | SEQ ID NO: 77 | SHP111 |

- ■ TATA1 (T1)
- ■ TATA2 (T2)
- ■ TATA3 (T3)
- ■ TATA4 (T4)
- ▨ TATA5 (T5)
- ✳ Point mutations
- ▭ Synthetic Element I

SEQUENCE LISTING

<160> NUMBER OF SEQ ID NOS: 83

<210> SEQ ID NO 1
<211> LENGTH: 2166
<212> TYPE: DNA
<213> ORGANISM: Glycine max
<220> FEATURE:
<221> NAME/KEY: misc_feature
<222> LOCATION: (1)...(2166)
<223> OTHER INFORMATION: Glycine max genomic sequence comprising the HPPD promoter

<400> SEQUENCE: 1
gcaagtattt caatacaata gccaaatttc tgattctgta aaagataata atcaaatagg 60

-continued

```
gggaaattag tttccccaca ttttcatcaa tagttttctg agggtgttga tcctttttct    120
ctccccttgt tggggcttta actgaatctt acttgactga tttgaatttc tttttcagtc    180
tttgaaaatt atgagattgt gatagattca ttgagacaag catctgaaga actccaactt    240
ttggaggtat gcaaactttc tgccttttaa tcttttgtgt aatcccttgt gagaggaaga    300
aaaatgagag ttcatgtgaa tgaatgtgtc ttgactacac agtggagact cttatttata    360
attagaactg caaatacagt agataattgt catataatta tacaactcat aatatcccta    420
atttacaata cttcttttac acaatatatt acataattac aagcttccga acagttgtca    480
ttggtccttt ttcatttgta agccttttttg ctgcatctct gcttcccgcc aaagttcact    540
tggatacatg attgcatgct tgtgatagat gctagagttg tgtaaagcgt aaaatgaagt    600
agggatgact gtcgcaatga aaaaccagtg caaaccaaaa gcagaggcat acattatatt    660
cgggcatata gatactggat aaatgtttat caaattgatt ttatggggtc ttaatacttg    720
caagatttat gttgtgatgg tgaaagctca ctagtcttaa tacacccaaa tccccttcta    780
ttgcttttta tttaagattt gattttcttg cagtttcatg aactggcagc tgaagctttc    840
tatctgatgg ccatggtata tgacaaactg gggcaattag aagaaaggga agaagctgca    900
gcttcatttc agaaacatat tttggctctc cgcaatcctc aagatgagga tgatcctctt    960
gttagtgtgt tttgattgtt ctttatagtt tatacctaat tttatctata taagcttatt   1020
aaattaaatt tatgtgcaat agtgacccct gatcttctgt aattatcatt caatagctgt   1080
agtcattttg tttccaattg taaccgtagc caagatgtac ggtggcataa accttggaga   1140
tattttgttc tctcttccct tcatagagga caaccttcat gtaatggaca tactaacgac   1200
aattaaatta tttatcattt taaaagatta aatatttttt cttaaattat tcctgtgctt   1260
taaaattctt aacagaaaat ttaaaattag acatttgtac cattagagaa aaactgtggg   1320
actcatttgt ttattagatt atttcagcta gcaactgact ctcttgtaca tttcattttt   1380
acattccttt aattatgcat cattaacagt agtagattgc atctcttaaa aaaaaaatta   1440
gattgcagta ttgccttgga aatatggaat tacaatgtca aaatatttta acgaataacg   1500
atgcgtagct taaagttcaa gacacaattt taacgttata tagtgcatca atgtttgaaa   1560
ttttagtgta taaataacgt atttttgata atattttta cacaacaatc ctcttaaatt   1620
ttcttatctt atttcattta accgttctct taaattgtct tatcttttt acacacaaat   1680
gaatcccaat aaacatggtt gggatttatt tgagttctta actttaggaa ccaaatatat   1740
aataattttt ttttttaaa aaaaaagaag ataaatatag aagaaaagga tgtgataaag   1800
gcaagagaag cgtgtgaaca agagagagac gaatctaggt ggatttgacg tacgttgaat   1860
gaatgttgaa tataagtaat aacgctgagg ctgtaggtgt gggtaataaa aaaagagaga   1920
agccgcatca acatcatcca atatatggac gttaaaagag cgtcgtaatc catttccatt   1980
tctcatctat cttcacttcc tcgtcctcat cctcatccac ctattctcaa cccagacgca   2040
atgcccatgt acactccatc actctccgca ccctcctcca atcacattca accaagtgtc   2100
acactcccct tatatatcac aaccaccaag ctcaatctca agcagcagca tcacaccaca   2160
ccaatg                                                                2166
```

<210> SEQ ID NO 2
<211> LENGTH: 1455
<212> TYPE: DNA
<213> ORGANISM: Artificial Sequence
<220> FEATURE:

-continued

<223> OTHER INFORMATION: SHP101C

<400> SEQUENCE: 2

```
gggtgttgat ccttttctc tccccttgtt ggggctttaa ctgaatctta cttgactgat     60
ttgaatttct ttttcagtct ttgaaaatta tgagattgtg atagattcat tgagacaagc   120
atctgaagaa ctccaacttt tggaggtatg caaactttct gccttttaat cttttgtgta   180
atcccttgtg agaggaagaa aaatgagagt tcatgtgaat gaatgtgtct tgactacaca   240
gtggagactc ttatttataa ttagaactgc aaatacagta gataattgtc atataattat   300
acaactcata atatccctaa tttacaatac ttcttttaca caatatatta cataattaca   360
agcttccgaa cagttgtcat tggtcctttt tcatttgtaa gccttttgc tgcatctctg   420
cttcccgcca aagttcactt ggatacatga ttgcatgctt gtgatagatg ctagagttgt   480
gtaaagcgta aaatgaagta gggatgactg tcgcaatgaa aaaccagtgc aaaccaaaag   540
cagaggcata cattatattc gggcatatag atactggata aatgtttatc aaattgattt   600
tatggggtct taatacttgc aagatttatg ttgtgatggt gaaagctcac tagtcttaat   660
acacccaaat ccccttctat tgctttttat ttaagatttg attttcttgc agtttcatga   720
actggcagct gaagctttct atctgatggc catggtatat gacaaactgg ggcaattaga   780
agaaagggaa gaagctgcag cttcatttca gaaacatatt ttggctctcc gcaatcctca   840
agatgaggat gatcctcttg ttagtgtgtt ttgattgttc tttatagttt atacctaatt   900
ttatctatat aagcttatta aattaaattt atgtgcaata gtgacccctg atcttctgta   960
attatcattc aatagctgta gtcattttgt ttccaattgt aaccgtagcc aagatgtacg  1020
gtggcataaa ccttggagat attttgttct ctcttccctt catagaggac aaccttcatg  1080
taatggacat actaacgaca attaaattat ttatcatttt aaaagattaa atattttttc  1140
ttaaattatt cctgtgcttt aaaattctta acagaaaatt taaaattaga catttgtacc  1200
attagagaaa aactgtggga ctcatttgtt tattagatta tttcagctag caactgactc  1260
tcttgtacat ttcattttta cattccttta attatgcatc attaacagta gtagattgca  1320
tctcttaaaa aaaaaattag attgcagtat tgccttggaa atatggaatt acaatgtcaa  1380
aatattttaa cgaataacga tgcgtagctt aaagttcaag acacaatttt aacgttatat  1440
agtgcatcag gtacc                                                   1455
```

<210> SEQ ID NO 3
<211> LENGTH: 1583
<212> TYPE: DNA
<213> ORGANISM: Artificial Sequence
<220> FEATURE:
<223> OTHER INFORMATION: SHP102C

<400> SEQUENCE: 3

```
gggtgttgat ccttttctc tccccttgtt ggggctttaa ctgaatctta cttgactgat     60
ttgaatttct ttttcagtct ttgaaaatta tgagattgtg atagattcat tgagacaagc   120
atctgaagaa ctccaacttt tggaggtatg caaactttct gccttttaat cttttgtgta   180
atcccttgtg agaggaagaa aaatgagagt tcatgtgaat gaatgtgtct tgactacaca   240
gtggagactc ttatttataa ttagaactgc aaatacagta gataattgtc atataattat   300
acaactcata atatccctaa tttacaatac ttcttttaca caatatatta cataattaca   360
agcttccgaa cagttgtcat tggtcctttt tcatttgtaa gccttttgc tgcatctctg   420
cttcccgcca aagttcactt ggatacatga ttgcatgctt gtgatagatg ctagagttgt   480
```

-continued

```
gtaaagcgta aaatgaagta gggatgactg tcgcaatgaa aaaccagtgc aaaccaaaag     540

cagaggcata cattatattc gggcatatag atactggata aatgtttatc aaattgattt     600

tatggggtct taatacttgc aagatttatg ttgtgatggt gaaagctcac tagtcttaat     660

acacccaaat ccccttctat tgctttttat ttaagatttg attttcttgc agtttcatga     720

actggcagct gaagctttct atctgatggc catggtatat gacaaactgg ggcaattaga     780

agaaagggaa gaagctgcag cttcatttca gaaacatatt ttggctctcc gcaatcctca     840

agatgaggat gatcctcttg ttagtgtgtt ttgattgttc tttatagttt atacctaatt     900

ttatctatat aagcttatta aattaaattt atgtgcaata gtgacccctg atcttctgta     960

attatcattc aatagctgta gtcattttgt ttccaattgt aaccgtagcc aagatgtacg    1020

gtggcataaa ccttggagat attttgttct ctcttccctt catagaggac aaccttcatg    1080

taatggacat actaacgaca attaaattat ttatcatttt aaaagattaa atattttttc    1140

ttaaattatt cctgtgcttt aaaattctta acagaaaatt taaaattaga catttgtacc    1200

attagagaaa aactgtggga ctcatttgtt tattagatta tttcagctag caactgactc    1260

tcttgtacat ttcattttta cattccttta attatgcatc attaacagta gtagattgca    1320

tctcttaaaa aaaaaattag attgcagtat tgccttggaa atatggaatt acaatgtcaa    1380

aatattttaa cgaataacga tgcgtagctt aaagttcaag acacaatttt aacgttatat    1440

agtgcatcaa tgtttgaaat tttagtgtat aaataacgta tttttgataa tattttttac    1500

acaacaatcc tcttaaattt tcttatctta tttcatttaa ccgttctctt aaattgtctt    1560

atcttttta cacacaaggt acc                                             1583
```

<210> SEQ ID NO 4
<211> LENGTH: 1946
<212> TYPE: DNA
<213> ORGANISM: Artificial Sequence
<220> FEATURE:
<223> OTHER INFORMATION: SHP103C

<400> SEQUENCE: 4

```
gggtgttgat cctttttctc tccccttgtt ggggctttaa ctgaatctta cttgactgat      60

ttgaatttct ttttcagtct ttgaaaatta tgagattgtg atagattcat tgagacaagc     120

atctgaagaa ctccaacttt tggaggtatg caaactttct gccttttaat cttttgtgta     180

atcccttgtg agaggaagaa aaatgagagt tcatgtgaat gaatgtgtct tgactacaca     240

gtggagactc ttatttataa ttagaactgc aaatacagta gataattgtc atataattat     300

acaactcata atatccctaa tttacaatac ttcttttaca caatatatta cataattaca     360

agcttccgaa cagttgtcat tggtcctttt tcatttgtaa gcctttttgc tgcatctctg     420

cttcccgcca aagttcactt ggatacatga ttgcatgctt gtgatagatg ctagagttgt     480

gtaaagcgta aaatgaagta gggatgactg tcgcaatgaa aaaccagtgc aaaccaaaag     540

cagaggcata cattatattc gggcatatag atactggata aatgtttatc aaattgattt     600

tatggggtct taatacttgc aagatttatg ttgtgatggt gaaagctcac tagtcttaat     660

acacccaaat ccccttctat tgctttttat ttaagatttg attttcttgc agtttcatga     720

actggcagct gaagctttct atctgatggc catggtatat gacaaactgg ggcaattaga     780

agaaagggaa gaagctgcag cttcatttca gaaacatatt ttggctctcc gcaatcctca     840

agatgaggat gatcctcttg ttagtgtgtt ttgattgttc tttatagttt atacctaatt     900
```

-continued

```
ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa ggtacc                                        1946
```

<210> SEQ ID NO 5
<211> LENGTH: 2068
<212> TYPE: DNA
<213> ORGANISM: Artificial Sequence
<220> FEATURE:
<223> OTHER INFORMATION: SHP104C

<400> SEQUENCE: 5

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gccttttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020
```

-continued

```
gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tattttttac   1500

acaacaatcc tcttaaattt tcttatctta tttcatttaa ccgttctctt aaattgtctt   1560

atcttttttta cacacaaatg aatcccaata aacatggttg ggatttattt gagttcttaa   1620

ctttaggaac caaatatata ataatttttt ttttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt atctatcaca accaccaagc tcaatctcaa   2040

gcagcagcat cacaccacac caggtacc                                      2068
```

<210> SEQ ID NO 6
<211> LENGTH: 2068
<212> TYPE: DNA
<213> ORGANISM: Artificial Sequence
<220> FEATURE:
<223> OTHER INFORMATION: SHP105C

<400> SEQUENCE: 6

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atccccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960
```

-continued

```
attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtac aaataacgta tttttgataa tatttttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt ttttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt atctatcaca accaccaagc tcaatctcaa   2040

gcagcagcat cacaccacac caggtacc                                      2068


<210> SEQ ID NO 7
<211> LENGTH: 2068
<212> TYPE: DNA
<213> ORGANISM: Artificial Sequence
<220> FEATURE:
<223> OTHER INFORMATION: SHP106C

<400> SEQUENCE: 7

gggtgttgat ccttttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960
```

-continued

```
attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtac aaataacgta tttttgataa tatttttttac  1500

acaacaatcc tcttaaattt tcttatctta tttcatttaa ccgttctctt aaattgtctt   1560

atcttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tagatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt atctatcaca accaccaagc tcaatctcaa   2040

gcagcagcat cacaccacac caggtacc                                      2068
```

<210> SEQ ID NO 8
<211> LENGTH: 2068
<212> TYPE: DNA
<213> ORGANISM: Artificial Sequence
<220> FEATURE:
<223> OTHER INFORMATION: SHP107C

<400> SEQUENCE: 8

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900
```

ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcaca accaccaagc tcaatctcaa 2040
gcagcagcat cacaccacac caggtacc 2068

<210> SEQ ID NO 9
<211> LENGTH: 2068
<212> TYPE: DNA
<213> ORGANISM: Artificial Sequence
<220> FEATURE:
<223> OTHER INFORMATION: SHP108C

<400> SEQUENCE: 9
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtcc gaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcaca accaccaagc tcaatctcaa 2040
gcagcagcat cacaccacac caggtacc 2068

<210> SEQ ID NO 10
<211> LENGTH: 2068
<212> TYPE: DNA
<213> ORGANISM: Artificial Sequence
<220> FEATURE:
<223> OTHER INFORMATION: SHP109C

<400> SEQUENCE: 10
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840

```
agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtcc gaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga    1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa cagatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt agcaatcaca accaccaagc tcaatctcaa   2040

gcagcagcat cacaccacac caggtacc                                      2068
```

```
<210> SEQ ID NO 11
<211> LENGTH: 1841
<212> TYPE: DNA
<213> ORGANISM: Artificial Sequence
<220> FEATURE:
<223> OTHER INFORMATION: SHP110C

<400> SEQUENCE: 11
```

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840
```

-continued

```
agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tatttttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcaggtac c                       1841
```

<210> SEQ ID NO 12
<211> LENGTH: 2068
<212> TYPE: DNA
<213> ORGANISM: Artificial Sequence
<220> FEATURE:
<223> OTHER INFORMATION: SHP111C

<400> SEQUENCE: 12

```
gggtgttgat ccttttctc tcccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gccttttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020
```

-continued gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa cagatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt atatatcaca accaccaagc tcaatctcaa 2040
gcagcagcat cacaccacac caggtacc 2068

<210> SEQ ID NO 13
<211> LENGTH: 2068
<212> TYPE: DNA
<213> ORGANISM: Artificial Sequence
<220> FEATURE:
<223> OTHER INFORMATION: SHP112C

<400> SEQUENCE: 13
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatacaga ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt atatatcaca accaccaagc tcaatctcaa 2040
gcagcagcat cacaccacac caggtacc 2068

<210> SEQ ID NO 14
<211> LENGTH: 2068
<212> TYPE: DNA
<213> ORGANISM: Artificial Sequence
<220> FEATURE:
<223> OTHER INFORMATION: SHP113C

<400> SEQUENCE: 14
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180 atccccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaac agaagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt atatatcaca accaccaagc tcaatctcaa 2040
gcagcagcat cacaccacac caggtacc 2068

<210> SEQ ID NO 15
<211> LENGTH: 2068
<212> TYPE: DNA
<213> ORGANISM: Artificial Sequence
<220> FEATURE:
<223> OTHER INFORMATION: SHP114C

<400> SEQUENCE: 15
gggtgttgat ccttttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960

```
attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt ttttttaaaa aaaaagaaga taaatataga   1680

agaaaaggat gtgataaagg caagagaagc gtgtgaacaa gagagagacg aatctaggtg   1740

gatttgacgt acgttgaatg aatgttgaac agaagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt agcaatcaca accaccaagc tcaatctcaa   2040

gcagcagcat cacaccacac caggtacc                                      2068
```

<210> SEQ ID NO 16
<211> LENGTH: 2068
<212> TYPE: DNA
<213> ORGANISM: Artificial Sequence
<220> FEATURE:
<223> OTHER INFORMATION: SHP115C

<400> SEQUENCE: 16

```
gggtgttgat ccttttctc tccccttgtt ggggctttaa ctgaatctta cttgactgat      60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gccttttgc tgcatctctg     420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900
```

-continued

```
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atattttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt tttttaaaa aaaaagaaga taaatataga   1680
agaaaaggat gtgataaagg caagagaagc gtgtgaacaa gagagagacg aatctaggtg   1740
gatttgacgt acgttgaatg aatgttgaac agaagtaata acgctgaggc tgtaggtgtg   1800
ggtaataaaa aaagagagaa gccgcatcaa catcatccaa cagatggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt atatatcaca accaccaagc tcaatctcaa   2040
gcagcagcat cacaccacac caggtacc                                      2068
```

```
<210> SEQ ID NO 17
<211> LENGTH: 2068
<212> TYPE: DNA
<213> ORGANISM: Artificial Sequence
<220> FEATURE:
<223> OTHER INFORMATION: SHP116C

<400> SEQUENCE: 17
```

```
gggtgttgat cctttttctc tccccttgtt ggggctttaa ctgaatctta cttgactgat     60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
```

ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtcc gaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaac agaagtaata acgctgaggc tgtaggtgtg 1800
ggtaataaaa aaagagagaa gccgcatcaa catcatccaa cagatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcaca accaccaagc tcaatctcaa 2040
gcagcagcat cacaccacac caggtacc 2068

<210> SEQ ID NO 18
<211> LENGTH: 2068
<212> TYPE: DNA
<213> ORGANISM: Artificial Sequence
<220> FEATURE:
<223> OTHER INFORMATION: SHP117C

<400> SEQUENCE: 18
gggtgttgat ccttttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840

-continued agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatacaga ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcaca accaccaagc tcaatctcaa 2040
gcagcagcat cacaccacac caggtacc 2068

<210> SEQ ID NO 19
<211> LENGTH: 2068
<212> TYPE: DNA
<213> ORGANISM: Artificial Sequence
<220> FEATURE:
<223> OTHER INFORMATION: SHP118C

<400> SEQUENCE: 19
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtcc gaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatacaga ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaac agaagtaata acgctgaggc tgtaggtgtg 1800
ggtaataaaa aaagagagaa gccgcatcaa catcatccaa cagatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcaca accaccaagc tcaatctcaa 2040
gcagcagcat cacaccacac caggtacc 2068

<210> SEQ ID NO 20
<211> LENGTH: 1754
<212> TYPE: DNA
<213> ORGANISM: Artificial Sequence
<220> FEATURE:
<223> OTHER INFORMATION: SHP0C

<400> SEQUENCE: 20
gggtgttgat ccttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780

-continued

```
agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgg tacc                                                     1754


<210> SEQ ID NO 21
<211> LENGTH: 99
<212> TYPE: DNA
<213> ORGANISM: Artificial Sequence
<220> FEATURE:
<223> OTHER INFORMATION: Synthetic Element I

<400> SEQUENCE: 21

actcgagcgg ctataaatac gtacctacgc acgctgcgct accatcccac aaccaccaag     60

ctcaatctca agcagcagca tcacaccaca ccaggtacc                            99


<210> SEQ ID NO 22
<211> LENGTH: 204
<212> TYPE: DNA
<213> ORGANISM: Artificial Sequence
<220> FEATURE:
<223> OTHER INFORMATION: Synthetic Element II

<400> SEQUENCE: 22

ggtctcatcg atcctatgcg tatggtatga cgtgtgttca agatgatgac ttcaaaccta     60

cctatgacgt atggtatgac gtgtgtcgac tgatgactta gatccactcg agcggctata    120

aatacgtacc tacgcacgct gcgctaccat cccacaacca ccaagctcaa tctcaagcag    180

cagcatcaca ccacaccagg tacc                                           204


<210> SEQ ID NO 23
<211> LENGTH: 1548
<212> TYPE: DNA
<213> ORGANISM: Artificial Sequence
<220> FEATURE:
<223> OTHER INFORMATION: SHP101

<400> SEQUENCE: 23

gggtgttgat ccttttctc tccccttgtt ggggctttaa ctgaatctta cttgactgat     60

ttgaatttct ttttcagtct ttgaaaatta tgagattgtg atagattcat tgagacaagc    120
```

atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa ctcgagcggc tataaatacg tacctacgca cgctgcgcta ccatccccaca 1500 accaccaagc tcaatctcaa gcagcagcat cacaccacac caggtacc 1548

<210> SEQ ID NO 24
<211> LENGTH: 1676
<212> TYPE: DNA
<213> ORGANISM: Artificial Sequence
<220> FEATURE:
<223> OTHER INFORMATION: SHP102

<400> SEQUENCE: 24
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600

-continued

```
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atattttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atctttttta cacacaaact cgagcggcta taaatacgta cctacgcacg ctgcgctacc   1620
atcccacaac caccaagctc aatctcaagc agcagcatca caccacacca ggtacc       1676
```

<210> SEQ ID NO 25
<211> LENGTH: 2039
<212> TYPE: DNA
<213> ORGANISM: Artificial Sequence
<220> FEATURE:
<223> OTHER INFORMATION: SHP103

<400> SEQUENCE: 25

```
gggtgttgat cctttttctc tccccttgtt ggggctttaa ctgaatctta cttgactgat     60
ttgaatttct ttttcagtct ttgaaaatta tgagattgtg atagattcat tgagacaagc    120
atctgaagaa ctccaacttt tggaggtatg caaactttct gccttttaat cttttgtgta    180
atccccttgtg agaggaagaa aaatgagagt tcatgtgaat gaatgtgtct tgactacaca   240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gccttttttgc tgcatctctg   420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
attatcattc aatagctgta gtcattttgt ttccaattgt aaccgtagcc aagatgtacg   1020
```

gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa actcgagcgg ctataaatac gtacctacgc acgctgcgct 1980
accatcccac aaccaccaag ctcaatctca agcagcagca tcacaccaca ccaggtacc 2039

<210> SEQ ID NO 26
<211> LENGTH: 2116
<212> TYPE: DNA
<213> ORGANISM: Artificial Sequence
<220> FEATURE:
<223> OTHER INFORMATION: SHP104

<400> SEQUENCE: 26
gggtgttgat ccttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020

```
gtggcataaa ccttggagat attttgttct ctcttccctt catagaggac aaccttcatg   1080
taatggacat actaacgaca attaaattat ttatcatttt aaaagattaa atatttttc    1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atcttttta cacacaaatg aatcccaata aacatggttg ggatttattt gagttcttaa    1620
ctttaggaac caaatatata ataatttttt tttttaaaa aaaaagaaga taaatataga    1680
agaaaaggat gtgataaagg caagagaagc gtgtgaacaa gagagagacg aatctaggtg   1740
gatttgacgt acgttgaatg aatgttgaat ataagtaata acgctgaggc tgtaggtgtg   1800
ggtaataaaa aaagagagaa gccgcatcaa catcatccaa tatatggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt atctatcact cgagcggcta taaatacgta   2040
cctacgcacg ctgcgctacc atcccacaac caccaagctc aatctcaagc agcagcatca   2100
caccacacca ggtacc                                                   2116
```

```
<210> SEQ ID NO 27
<211> LENGTH: 2116
<212> TYPE: DNA
<213> ORGANISM: Artificial Sequence
<220> FEATURE:
<223> OTHER INFORMATION: SHP105

<400> SEQUENCE: 27
```

```
gggtgttgat ccttttctc tccccttgtt ggggctttaa ctgaatctta cttgactgat      60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
```

attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtac aaataacgta tttttgataa tatttttttac 1500 acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt atctatcact cgagcggcta taaatacgta 2040
cctacgcacg ctgcgctacc atcccacaac caccaagctc aatctcaagc agcagcatca 2100
caccacacca ggtacc 2116

<210> SEQ ID NO 28
<211> LENGTH: 2116
<212> TYPE: DNA
<213> ORGANISM: Artificial Sequence
<220> FEATURE:
<223> OTHER INFORMATION: SHP106

<400> SEQUENCE: 28
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180 atccccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840

-continued

```
agatgaggat gatcctcttg ttagtgtgtt ttgattgttc tttatagttt atacctaatt     900

ttatctatat aagcttatta aattaaattt atgtgcaata gtgacccctg atcttctgta     960

attatcattc aatagctgta gtcattttgt ttccaattgt aaccgtagcc aagatgtacg    1020

gtggcataaa ccttggagat attttgttct ctcttccctt catagaggac aaccttcatg    1080

taatggacat actaacgaca attaaattat ttatcatttt aaaagattaa atattttttc    1140

ttaaattatt cctgtgcttt aaaattctta acagaaaatt taaaattaga catttgtacc    1200

attagagaaa aactgtggga ctcatttgtt tattagatta tttcagctag caactgactc    1260

tcttgtacat ttcattttta cattccttta attatgcatc attaacagta gtagattgca    1320

tctcttaaaa aaaaaattag attgcagtat tgccttggaa atatggaatt acaatgtcaa    1380

aatattttaa cgaataacga tgcgtagctt aaagttcaag acacaatttt aacgttatat    1440

agtgcatcaa tgtttgaaat tttagtgtac aaataacgta tttttgataa tattttttac    1500

acaacaatcc tcttaaattt tcttatctta tttcatttaa ccgttctctt aaattgtctt    1560

atcttttta cacacaaatg aatcccaata aacatggttg ggatttattt gagttcttaa    1620

ctttaggaac caaatatata ataatttttt ttttttaaaa aaaaagaaga taaatataga    1680

agaaaaggat gtgataaagg caagagaagc gtgtgaacaa gagagagacg aatctaggtg    1740

gatttgacgt acgttgaatg aatgttgaat ataagtaata acgctgaggc tgtaggtgtg    1800

ggtaataaaa aaagagagaa gccgcatcaa catcatccaa tagatggacg ttaaaagagc    1860

gtcgtaatcc atttccattt ctcatctatc ttcacttcct cgtcctcatc ctcatccacc    1920

tattctcaac ccagacgcaa tgcccatgta cactccatca ctctccgcac cctcctccaa    1980

tcacattcaa ccaagtgtca cactcccctt atctatcact cgagcggcta taaatacgta    2040

cctacgcacg ctgcgctacc atcccacaac caccaagctc aatctcaagc agcagcatca    2100

caccacacca ggtacc                                                     2116
```

```
<210> SEQ ID NO 29
<211> LENGTH: 2116
<212> TYPE: DNA
<213> ORGANISM: Artificial Sequence
<220> FEATURE:
<223> OTHER INFORMATION: SHP107

<400> SEQUENCE: 29
```

```
gggtgttgat ccttttctc tccccttgtt ggggctttaa ctgaatctta cttgactgat      60

ttgaatttct ttttcagtct ttgaaaatta tgagattgtg atagattcat tgagacaagc     120

atctgaagaa ctccaacttt tggaggtatg caaactttct gccttttaat cttttgtgta     180

atcccttgtg agaggaagaa aaatgagagt tcatgtgaat gaatgtgtct tgactacaca     240

gtggagactc ttatttataa ttagaactgc aaatacagta gataattgtc atataattat     300

acaactcata atatccctaa tttacaatac ttcttttaca caatatatta cataattaca     360

agcttccgaa cagttgtcat tggtcctttt tcatttgtaa gcctttttgc tgcatctctg     420

cttcccgcca aagttcactt ggatacatga ttgcatgctt gtgatagatg ctagagttgt     480

gtaaagcgta aaatgaagta gggatgactg tcgcaatgaa aaaccagtgc aaaccaaaag     540

cagaggcata cattatattc gggcatatag atactggata aatgtttatc aaattgattt     600

tatggggtct taatacttgc aagatttatg ttgtgatggt gaaagctcac tagtcttaat     660

acacccaaat ccccttctat tgctttttat ttaagatttg attttcttgc agtttcatga     720

actggcagct gaagctttct atctgatggc catggtatat gacaaactgg ggcaattaga     780
```

agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcact cgagcggcta taaatacgta 2040
cctacgcacg ctgcgctacc atcccacaac caccaagctc aatctcaagc agcagcatca 2100
caccacacca ggtacc 2116

<210> SEQ ID NO 30
<211> LENGTH: 2116
<212> TYPE: DNA
<213> ORGANISM: Artificial Sequence
<220> FEATURE:
<223> OTHER INFORMATION: SHP108

<400> SEQUENCE: 30
gggtgttgat ccttttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660

-continued acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtcc gaataacgta tttttgataa tatttttttac 1500 acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt agcaatcact cgagcggcta taaatacgta 2040
cctacgcacg ctgcgctacc atcccacaac caccaagctc aatctcaagc agcagcatca 2100
caccacacca ggtacc 2116

<210> SEQ ID NO 31
<211> LENGTH: 2116
<212> TYPE: DNA
<213> ORGANISM: Artificial Sequence
<220> FEATURE:
<223> OTHER INFORMATION: SHP109

<400> SEQUENCE: 31
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600

```
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atatttttc    1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtcc gaataacgta tttttgataa tattttttac   1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt ttttttaaaa aaaaagaaga taaatataga   1680
agaaaaggat gtgataaagg caagagaagc gtgtgaacaa gagagagacg aatctaggtg   1740
gatttgacgt acgttgaatg aatgttgaat ataagtaata acgctgaggc tgtaggtgtg   1800
ggtaataaaa aaagagagaa gccgcatcaa catcatccaa cagatggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt agcaatcact cgagcggcta taaatacgta   2040
cctacgcacg ctgcgctacc atcccacaac caccaagctc aatctcaagc agcagcatca   2100
caccacacca ggtacc                                                   2116
```

<210> SEQ ID NO 32
<211> LENGTH: 1648
<212> TYPE: DNA
<213> ORGANISM: Artificial Sequence
<220> FEATURE:
<223> OTHER INFORMATION: SHP201

<400> SEQUENCE: 32

```
gggtgttgat cctttttctc tccccttgtt ggggctttaa ctgaatctta cttgactgat     60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
```

gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa ctcgatccta tgcgtatggt atgacgtgtg ttcaagatga tgacttcaaa 1500
cctacctatg acgtatggta tgacgtgtgt cgactgatga cttagatcca ctcgagcggc 1560
tataaatacg tacctacgca cgctgcgcta ccatcccaca accaccaagc tcaatctcaa 1620
gcagcagcat cacaccacac caggtacc 1648

<210> SEQ ID NO 33
<211> LENGTH: 1776
<212> TYPE: DNA
<213> ORGANISM: Artificial Sequence
<220> FEATURE:
<223> OTHER INFORMATION: SHP202

<400> SEQUENCE: 33
gggtgttgat ccttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560 atcttttta cacacaaact cgatcctatg cgtatggtat gacgtgtgtt caagatgatg 1620
acttcaaacc tacctatgac gtatggtatg acgtgtgtcg actgatgact tagatccact 1680
cgagcggcta taaatacgta cctacgcacg ctgcgctacc atcccacaac caccaagctc 1740
aatctcaagc agcagcatca caccacacca ggtacc 1776

<210> SEQ ID NO 34
<211> LENGTH: 2139
<212> TYPE: DNA
<213> ORGANISM: Artificial Sequence
<220> FEATURE:
<223> OTHER INFORMATION: SHP203

<400> SEQUENCE: 34
gggtgttgat ccttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140

-continued ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa actcgatcct atgcgtatgg tatgacgtgt gttcaagatg 1980
atgacttcaa acctacctat gacgtatggt atgacgtgtg tcgactgatg acttagatcc 2040
actcgagcgg ctataaatac gtacctacgc acgctgcgct accatcccac aaccaccaag 2100
ctcaatctca agcagcagca tcacaccaca ccaggtacc 2139

<210> SEQ ID NO 35
<211> LENGTH: 2216
<212> TYPE: DNA
<213> ORGANISM: Artificial Sequence
<220> FEATURE:
<223> OTHER INFORMATION: SHP204

<400> SEQUENCE: 35
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080

-continued

```
taatggacat actaacgaca attaaattat ttatcatttt aaaagattaa atatttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atcttttta cacacaaatg aatcccaata aacatggttg ggatttattt gagttcttaa   1620
ctttaggaac caaatatata ataatttttt tttttaaaa aaaaagaaga taaatataga   1680
agaaaaggat gtgataaagg caagagaagc gtgtgaacaa gagagagacg aatctaggtg   1740
gatttgacgt acgttgaatg aatgttgaat ataagtaata acgctgaggc tgtaggtgtg   1800
ggtaataaaa aaagagagaa gccgcatcaa catcatccaa tatatggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt atctatcact cgatcctatg cgtatggtat   2040
gacgtgtgtt caagatgatg acttcaaacc tacctatgac gtatggtatg acgtgtgtcg   2100
actgatgact tagatccact cgagcggcta taaatacgta cctacgcacg ctgcgctacc   2160
atcccacaac caccaagctc aatctcaagc agcagcatca caccacacca ggtacc       2216
```

```
<210> SEQ ID NO 36
<211> LENGTH: 2216
<212> TYPE: DNA
<213> ORGANISM: Artificial Sequence
<220> FEATURE:
<223> OTHER INFORMATION: SHP205

<400> SEQUENCE: 36
```

```
gggtgttgat ccttttctc tccccttgtt ggggctttaa ctgaatctta cttgactgat     60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
```

ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140
ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtac aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcccctt atctatcact cgatcctatg cgtatggtat 2040
gacgtgtgtt caagatgatg acttcaaacc tacctatgac gtatggtatg acgtgtgtcg 2100
actgatgact tagatccact cgagcggcta taaatacgta cctacgcacg ctgcgctacc 2160
atcccacaac caccaagctc aatctcaagc agcagcatca caccacacca ggtacc 2216

<210> SEQ ID NO 37
<211> LENGTH: 2216
<212> TYPE: DNA
<213> ORGANISM: Artificial Sequence
<220> FEATURE:
<223> OTHER INFORMATION: SHP206

<400> SEQUENCE: 37
gggtgttgat ccttttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780

-continued

```
agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtac aaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tagatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt atctatcact cgatcctatg cgtatggtat   2040

gacgtgtgtt caagatgatg acttcaaacc tacctatgac gtatggtatg acgtgtgtcg   2100

actgatgact tagatccact cgagcggcta taaatacgta cctacgcacg ctgcgctacc   2160

atcccacaac caccaagctc aatctcaagc agcagcatca caccacacca ggtacc       2216


<210> SEQ ID NO 38
<211> LENGTH: 2216
<212> TYPE: DNA
<213> ORGANISM: Artificial Sequence
<220> FEATURE:
<223> OTHER INFORMATION: SHP207

<400> SEQUENCE: 38

gggtgttgat ccttttctc tccccttgtt ggggctttaa ctgaatctta cttgactgat      60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gccttttttgc tgcatctctg   420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600
```

-continued

```
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atattttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt tttttaaaa aaaaagaaga taaatataga   1680
agaaaaggat gtgataaagg caagagaagc gtgtgaacaa gagagagacg aatctaggtg   1740
gatttgacgt acgttgaatg aatgttgaat ataagtaata acgctgaggc tgtaggtgtg   1800
ggtaataaaa aaagagagaa gccgcatcaa catcatccaa tatatggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt agcaatcact cgatcctatg cgtatggtat   2040
gacgtgtgtt caagatgatg acttcaaacc tacctatgac gtatggtatg acgtgtgtcg   2100
actgatgact tagatccact cgagcggcta taaatacgta cctacgcacg ctgcgctacc   2160
atcccacaac caccaagctc aatctcaagc agcagcatca caccacacca ggtacc       2216
```

```
<210> SEQ ID NO 39
<211> LENGTH: 2216
<212> TYPE: DNA
<213> ORGANISM: Artificial Sequence
<220> FEATURE:
<223> OTHER INFORMATION: SHP208

<400> SEQUENCE: 39
```

```
gggtgttgat ccttttctc tccccttgtt ggggctttaa ctgaatctta cttgactgat      60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
```

-continued

```
gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtcc gaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt agcaatcact cgatcctatg cgtatggtat   2040

gacgtgtgtt caagatgatg acttcaaacc tacctatgac gtatggtatg acgtgtgtcg   2100

actgatgact tagatccact cgagcggcta taaatacgta cctacgcacg ctgcgctacc   2160

atcccacaac caccaagctc aatctcaagc agcagcatca caccacacca ggtacc       2216
```

```
<210> SEQ ID NO 40
<211> LENGTH: 2216
<212> TYPE: DNA
<213> ORGANISM: Artificial Sequence
<220> FEATURE:
<223> OTHER INFORMATION: SHP209

<400> SEQUENCE: 40
```

```
gggtgttgat ccttttctc tccccttgtt ggggctttaa ctgaatctta cttgactgat      60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300
```

-continued

```
acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtcc gaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt ttttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa cagatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt agcaatcact cgatcctatg cgtatggtat   2040

gacgtgtgtt caagatgatg acttcaaacc tacctatgac gtatggtatg acgtgtgtcg   2100

actgatgact tagatccact cgagcggcta taaatacgta cctacgcacg ctgcgctacc   2160

atcccacaac caccaagctc aatctcaagc agcagcatca caccacacca ggtacc       2216
```

<210> SEQ ID NO 41
<211> LENGTH: 2054
<212> TYPE: DNA
<213> ORGANISM: Artificial Sequence
<220> FEATURE:
<223> OTHER INFORMATION: SHP110

<400> SEQUENCE: 41

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180
```

-continued

```
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gccttttttgc tgcatctctg    420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atattttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tatttttttac  1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt ttttttaaaa aaaaagaaga taaatataga   1680
agaaaaggat gtgataaagg caagagaagc gtgtgaacaa gagagagacg aatctaggtg   1740
gatttgacgt acgttgaatg aatgttactc gagcggctat aaatacgtac ctacgcacgc   1800
tgcgctacca tcccaataaa aaaagagaga agccgcatca acatcatcca atatatggac   1860
gttaaaagag cgtcgtaatc catttccatt tctcatctat cttcacttcc tcgtcctcat   1920
cctcatccac ctattctcaa cccagacgca atgcccatgt acactccatc actctccgca   1980
ccctcctcca atcacattca accaagtgtc acactcccct tatatatcac aaccaccaag   2040
ctcaatctca agca                                                     2054
```

<210> SEQ ID NO 42
<211> LENGTH: 22
<212> TYPE: DNA
<213> ORGANISM: Artificial Sequence
<220> FEATURE:
<223> OTHER INFORMATION: forward primer

<400> SEQUENCE: 42

```
gcaagtattt caatacaata gc                                              22
```

<210> SEQ ID NO 43

-continued

<211> LENGTH: 20
<212> TYPE: DNA
<213> ORGANISM: Artificial Sequence
<220> FEATURE:
<223> OTHER INFORMATION: reverse primer

<400> SEQUENCE: 43
gttatctgat atgatgttgc 20

<210> SEQ ID NO 44
<211> LENGTH: 10
<212> TYPE: DNA
<213> ORGANISM: Glycine max
<220> FEATURE:
<221> NAME/KEY: TATA_signal
<222> LOCATION: (1)...(10)
<223> OTHER INFORMATION: TATA1

<400> SEQUENCE: 44
gtataaataa 10

<210> SEQ ID NO 45
<211> LENGTH: 10
<212> TYPE: DNA
<213> ORGANISM: Glycine max
<220> FEATURE:
<221> NAME/KEY: TATA_signal
<222> LOCATION: (1)...(10)
<223> OTHER INFORMATION: TATA2

<400> SEQUENCE: 45
ccaatatatg 10

<210> SEQ ID NO 46
<211> LENGTH: 11
<212> TYPE: DNA
<213> ORGANISM: Glycine max
<220> FEATURE:
<221> NAME/KEY: TATA_signal
<222> LOCATION: (1)...(11)
<223> OTHER INFORMATION: TATA3

<400> SEQUENCE: 46
ccttatatat c 11

<210> SEQ ID NO 47
<211> LENGTH: 10
<212> TYPE: DNA
<213> ORGANISM: Glycine max
<220> FEATURE:
<221> NAME/KEY: TATA_signal
<222> LOCATION: (1)...(10)
<223> OTHER INFORMATION: TATA4

<400> SEQUENCE: 47
tatataataa 10

<210> SEQ ID NO 48
<211> LENGTH: 9
<212> TYPE: DNA
<213> ORGANISM: Glycine max
<220> FEATURE:
<221> NAME/KEY: TATA_signal
<222> LOCATION: (1)...(9)
<223> OTHER INFORMATION: TATA5

<400> SEQUENCE: 48 gaatataag 9

<210> SEQ ID NO 49
<211> LENGTH: 29
<212> TYPE: DNA
<213> ORGANISM: Glycine max
<220> FEATURE:
<221> NAME/KEY: misc_feature
<222> LOCATION: (1)...(29)
<223> OTHER INFORMATION: 5' fragment

<400> SEQUENCE: 49
gtaataaaaa aagagagaag ccgcatcaa 29

<210> SEQ ID NO 50
<211> LENGTH: 29
<212> TYPE: DNA
<213> ORGANISM: Glycine max
<220> FEATURE:
<221> NAME/KEY: misc_feature
<222> LOCATION: (1)...(29)
<223> OTHER INFORMATION: 5' fragment

<400> SEQUENCE: 50
aagcagcagc atcacaccac accaatgcc 29

<210> SEQ ID NO 51
<211> LENGTH: 21
<212> TYPE: DNA
<213> ORGANISM: Artificial Sequence
<220> FEATURE:
<223> OTHER INFORMATION: forward primer hp0234

<400> SEQUENCE: 51
gttttccgcg ggtgttgatc c 21

<210> SEQ ID NO 52
<211> LENGTH: 30
<212> TYPE: DNA
<213> ORGANISM: Artificial Sequence
<220> FEATURE:
<223> OTHER INFORMATION: reverse primer hp2296

<400> SEQUENCE: 52
tcattggtac ctggtgtggt gtgatgctgc 30

<210> SEQ ID NO 53
<211> LENGTH: 27
<212> TYPE: DNA
<213> ORGANISM: Artificial Sequence
<220> FEATURE:
<223> OTHER INFORMATION: reverse primer hp2154

<400> SEQUENCE: 53
agcatggtac cttgcgtctg ggttgag 27

<210> SEQ ID NO 54
<211> LENGTH: 25
<212> TYPE: DNA
<213> ORGANISM: Artificial Sequence
<220> FEATURE:
<223> OTHER INFORMATION: reverse primer hp1962

<400> SEQUENCE: 54
aggaggtacc gtcaaatcca cctag 25

<210> SEQ ID NO 55

<211> LENGTH: 28
<212> TYPE: DNA
<213> ORGANISM: Artificial Sequence
<220> FEATURE:
<223> OTHER INFORMATION: reverse primer hp1663

<400> SEQUENCE: 55
tccttggtac ctgatgcact atataacg 28

<210> SEQ ID NO 56
<211> LENGTH: 45
<212> TYPE: DNA
<213> ORGANISM: Glycine max
<220> FEATURE:
<221> NAME/KEY: 5'UTR
<222> LOCATION: (1)...(45)
<223> OTHER INFORMATION: putative 5' UTR

<400> SEQUENCE: 56
acaaccacca agctcaatct caagcagcag catcacacca cacca 45

<210> SEQ ID NO 57
<211> LENGTH: 2064
<212> TYPE: DNA
<213> ORGANISM: Glycine max

<400> SEQUENCE: 57
gtaataaaaa aagagagaag ccgcatcaac atcatccaat atatggacgt taaaagagcg 60
tcgtaatcca tttccatttc tcatctatct tcacttcctc gtcctcatcc tcatccacct 120
attctcaacc cagacgcaat gcccatgtac actccatcac tctccgcacc ctcctccaat 180
cacattcaac caagtgtcac actcccctta tatatcacaa ccaccaagct caatctcaag 240
cagcagcatc acaccacacc aatgccaata cccatgtgca acgaaattca agcccaagcc 300
caagcccaag cccaacctgg gtttaagctc gtcggtttca aaaacttcgt ccgaaccaat 360
cctaagtcgg accgctttca agtcaaccgc ttccaccaca tcgagttctg gtgcaccgat 420
gccaccaacg cctctcgccg attctcttgg ggacttggaa tgcctattgt ggcaaaatct 480
gatctctcca ccggaaacca aatccacgcc tcctacctcc tccgctccgg cgacctctcc 540
ttcctcttct ccgctcctta ctctccctct ctctccgccg gctcctccgc tgcctcctcc 600
gcctccattc ccagtttcga cgccgccacc tgccttgcct tcgctgccaa acacggcttc 660
ggcgtccgcg ccatcgcctt ggaagtcgcc gacgcggaag ccgctttcag cgccagcgtc 720
gcgaaaggag ccgagccggc gtcgccgccg gttctcgtcg acgatcgcac cggcttcgcg 780
gaggtgcgcc tctacggcga cgtggtgctc cgctacgtca gctacaagga cgccgcgccg 840
caggcgccac acgcagatcc gtcgcggtgg ttcctgccgg gattcgaggc cgcggcgtcg 900
tcgtcttcgt ttccggagct ggactacggg atccggcggc tggaccacgc cgtcgggaac 960
gttccggagc tggcgccggc ggtgaggtac ctgaaaggct tcagcggatt ccacgagttc 1020
gcggagttca ccgcggagga cgtgggaacg agcgagagcg ggttgaactc ggtggttctg 1080
gcgaacaact cggagacggt gttgctgccg ctgaacgagc cggtttacgg aacgaagagg 1140
aagagccaga ttgagacgta tttggaacac aacgaaggtg ctggtgtgca gcaccttgcg 1200
cttgttactc acgacatctt caccacactg agagagatga gaaagcgaag tttccttggt 1260
ggatttgagt tcatgccttc tcctcctccc acctattacg ccaacctcca caaccgtgcc 1320
gctgatgtgt tgaccgttga ccagattaag cagtgtgagg agcttgggat tcttgttgac 1380
agagatgatc agggcactct gcttcagatt ttcactaagc ctgttgggga caggttcttc 1440

-continued

```
atttctgct tctttttttt ttttttgttt ttttaatccc tgctaaacaa ctttattata   1500
actctcacat tctattagcc tagccttgat gacttttaat ttacgttaaa ctgtgctttt   1560
tattctccta ctttgttagt tttttttta tataaaattt taatttttca attataactt   1620
tcaataatta acaaatgatg tacagtatag tgttatgtca gagtggatgt acttgatgta   1680
gcagttcatc agagtgtttc ccactacaaa ttgtactttt gtccctttcc tgacataaag   1740
tttacgacat tgaaaaaatt gatagataaa agtgcaattt atttatcttc cgctttgaac   1800
tgattgaaag tggtaaaagt tagattaaca atttgacagt gtttgtgtgt tggagggtgg   1860
tgattagtta aatgtgtttt gtgttgaatt gacaggccaa cgatattcat agagataatt   1920
cagaggatcg ggtgcatggt ggaggatgag gaagggaagg tgtaccagaa gggtgcatgt   1980
gggggttttg ggaaaggcaa tttttctgag cttttcaaat ccattgaaga atatgagaag   2040
actttggaag ctaaaagaac cgcg                                          2064
```

<210> SEQ ID NO 58
<211> LENGTH: 488
<212> TYPE: PRT
<213> ORGANISM: Glycine max

<400> SEQUENCE: 58

```
Met Pro Met Tyr Thr Pro Ser Leu Ser Ala Pro Ser Ser Asn His Ile
 1               5                  10                  15

Gln Pro Ser Val Thr Leu Pro Leu Tyr Ile Thr Thr Thr Lys Leu Asn
            20                  25                  30

Leu Lys Gln Gln His His Thr Thr Pro Met Pro Ile Pro Met Cys Asn
        35                  40                  45

Glu Ile Gln Ala Gln Ala Gln Ala Gln Ala Gln Pro Gly Phe Lys Leu
    50                  55                  60

Val Gly Phe Lys Asn Phe Val Arg Thr Asn Pro Lys Ser Asp Arg Phe
65                  70                  75                  80

Gln Val Asn Arg Phe His His Ile Glu Phe Trp Cys Thr Asp Ala Thr
                85                  90                  95

Asn Ala Ser Arg Arg Phe Ser Trp Gly Leu Gly Met Pro Ile Val Ala
            100                 105                 110

Lys Ser Asp Leu Ser Thr Gly Asn Gln Ile His Ala Ser Tyr Leu Leu
        115                 120                 125

Arg Ser Gly Asp Leu Ser Phe Leu Phe Ser Ala Pro Tyr Ser Pro Ser
    130                 135                 140

Leu Ser Ala Gly Ser Ser Ala Ala Ser Ser Ala Ser Ile Pro Ser Phe
145                 150                 155                 160

Asp Ala Ala Thr Cys Leu Ala Phe Ala Ala Lys His Gly Phe Gly Val
                165                 170                 175

Arg Ala Ile Ala Leu Glu Val Ala Asp Ala Glu Ala Ala Phe Ser Ala
            180                 185                 190

Ser Val Ala Lys Gly Ala Glu Pro Ala Ser Pro Pro Val Leu Val Asp
        195                 200                 205

Asp Arg Thr Gly Phe Ala Glu Val Arg Leu Tyr Gly Asp Val Val Leu
    210                 215                 220

Arg Tyr Val Ser Tyr Lys Asp Ala Ala Pro Gln Ala Pro His Ala Asp
225                 230                 235                 240

Pro Ser Arg Trp Phe Leu Pro Gly Phe Glu Ala Ala Ala Ser Ser Ser
                245                 250                 255
```

-continued

```
Ser Phe Pro Glu Leu Asp Tyr Gly Ile Arg Arg Leu Asp His Ala Val
            260                 265                 270

Gly Asn Val Pro Glu Leu Ala Pro Ala Val Arg Tyr Leu Lys Gly Phe
        275                 280                 285

Ser Gly Phe His Glu Phe Ala Glu Phe Thr Ala Glu Asp Val Gly Thr
    290                 295                 300

Ser Glu Ser Gly Leu Asn Ser Val Val Leu Ala Asn Asn Ser Glu Thr
305                 310                 315                 320

Val Leu Leu Pro Leu Asn Glu Pro Val Tyr Gly Thr Lys Arg Lys Ser
                325                 330                 335

Gln Ile Glu Thr Tyr Leu Glu His Asn Glu Gly Ala Gly Val Gln His
            340                 345                 350

Leu Ala Leu Val Thr His Asp Ile Phe Thr Thr Leu Arg Glu Met Arg
        355                 360                 365

Lys Arg Ser Phe Leu Gly Gly Phe Glu Phe Met Pro Ser Pro Pro Pro
    370                 375                 380

Thr Tyr Tyr Ala Asn Leu His Asn Arg Ala Ala Asp Val Leu Thr Val
385                 390                 395                 400

Asp Gln Ile Lys Gln Cys Glu Glu Leu Gly Ile Leu Val Asp Arg Asp
                405                 410                 415

Asp Gln Gly Thr Leu Leu Gln Ile Phe Thr Lys Pro Val Gly Asp Arg
            420                 425                 430

Pro Thr Ile Phe Ile Glu Ile Ile Gln Arg Ile Gly Cys Met Val Glu
        435                 440                 445

Asp Glu Glu Gly Lys Val Tyr Gln Lys Gly Ala Cys Gly Gly Phe Gly
    450                 455                 460

Lys Gly Asn Phe Ser Glu Leu Phe Lys Ser Ile Glu Glu Tyr Glu Lys
465                 470                 475                 480

Thr Leu Glu Ala Lys Arg Thr Ala
                485


<210> SEQ ID NO 59
<211> LENGTH: 258
<212> TYPE: PRT
<213> ORGANISM: Glycine max

<400> SEQUENCE: 59

Ala Thr Gly Cys Cys Cys Ala Thr Gly Thr Ala Cys Ala Cys Thr Cys
 1               5                  10                  15

Cys Ala Thr Cys Ala Cys Thr Cys Thr Cys Cys Gly Cys Ala Cys Cys
            20                  25                  30

Cys Thr Cys Cys Thr Cys Cys Ala Ala Thr Cys Ala Cys Ala Thr Thr
        35                  40                  45

Cys Ala Ala Cys Cys Ala Ala Gly Thr Gly Thr Cys Ala Cys Ala Cys
    50                  55                  60

Thr Cys Cys Cys Cys Thr Thr Ala Thr Ala Thr Ala Thr Cys Ala Cys
65                  70                  75                  80

Ala Ala Cys Cys Ala Cys Cys Ala Ala Gly Cys Thr Cys Ala Ala Thr
                85                  90                  95

Cys Thr Cys Ala Ala Gly Cys Ala Gly Cys Ala Gly Cys Ala Thr Cys
            100                 105                 110

Ala Cys Ala Cys Cys Ala Cys Ala Cys Cys Ala Ala Thr Gly Cys Cys
        115                 120                 125

Ala Ala Thr Ala Cys Cys Cys Ala Thr Gly Thr Gly Cys Ala Ala Cys
    130                 135                 140
```

```
Gly Ala Ala Ala Thr Thr Cys Ala Ala Gly Cys Cys Cys Ala Ala Gly
145                 150                 155                 160

Cys Cys Cys Ala Ala Gly Cys Cys Cys Ala Ala Gly Cys Cys Cys Ala
                165                 170                 175

Ala Cys Cys Thr Gly Gly Gly Thr Thr Thr Ala Ala Gly Cys Thr Cys
            180                 185                 190

Gly Thr Cys Gly Gly Thr Thr Thr Cys Ala Ala Ala Ala Ala Cys Thr
        195                 200                 205

Thr Cys Gly Thr Cys Cys Gly Ala Ala Cys Cys Ala Ala Thr Cys Cys
    210                 215                 220

Thr Ala Ala Gly Thr Cys Gly Gly Ala Cys Cys Gly Cys Thr Thr Thr
225                 230                 235                 240

Cys Ala Ala Gly Thr Cys Ala Ala Cys Cys Gly Cys Thr Thr Cys Cys
                245                 250                 255

Ala Cys
```

<210> SEQ ID NO 60
<211> LENGTH: 86
<212> TYPE: PRT
<213> ORGANISM: Glycine max

<400> SEQUENCE: 60

```
Met Pro Met Tyr Thr Pro Ser Leu Ser Ala Pro Ser Ser Asn His Ile
 1               5                  10                  15

Gln Pro Ser Val Thr Leu Pro Leu Tyr Ile Thr Thr Thr Lys Leu Asn
            20                  25                  30

Leu Lys Gln Gln His His Thr Thr Pro Met Pro Ile Pro Met Cys Asn
        35                  40                  45

Glu Ile Gln Ala Gln Ala Gln Ala Gln Ala Gln Pro Gly Phe Lys Leu
    50                  55                  60

Val Gly Phe Lys Asn Phe Val Arg Thr Asn Pro Lys Ser Asp Arg Phe
65                  70                  75                  80

Gln Val Asn Arg Phe His
                85
```

<210> SEQ ID NO 61
<211> LENGTH: 447
<212> TYPE: PRT
<213> ORGANISM: Glycine max

<400> SEQUENCE: 61

```
Met Pro Ile Pro Met Cys Asn Glu Ile Gln Ala Gln Ala Gln Ala Gln
 1               5                  10                  15

Ala Gln Pro Gly Phe Lys Leu Val Gly Phe Lys Asn Phe Val Arg Thr
            20                  25                  30

Asn Pro Lys Ser Asp Arg Phe Gln Val Asn Arg Phe His His Ile Glu
        35                  40                  45

Phe Trp Cys Thr Asp Ala Thr Asn Ala Ser Arg Arg Phe Ser Trp Gly
    50                  55                  60

Leu Gly Met Pro Ile Val Ala Lys Ser Asp Leu Ser Thr Gly Asn Gln
65                  70                  75                  80

Ile His Ala Ser Tyr Leu Leu Arg Ser Gly Asp Leu Ser Phe Leu Phe
                85                  90                  95

Ser Ala Pro Tyr Ser Pro Ser Leu Ser Ala Gly Ser Ser Ala Ala Ser
            100                 105                 110
```

-continued

```
Ser Ala Ser Ile Pro Ser Phe Asp Ala Ala Thr Cys Leu Ala Phe Ala
        115                 120                 125

Ala Lys His Gly Phe Gly Val Arg Ala Ile Ala Leu Glu Val Ala Asp
    130                 135                 140

Ala Glu Ala Ala Phe Ser Ala Ser Val Ala Lys Gly Ala Glu Pro Ala
145                 150                 155                 160

Ser Pro Pro Val Leu Val Asp Asp Arg Thr Gly Phe Ala Glu Val Arg
                165                 170                 175

Leu Tyr Gly Asp Val Val Leu Arg Tyr Val Ser Tyr Lys Asp Ala Ala
            180                 185                 190

Pro Gln Ala Pro His Ala Asp Pro Ser Arg Trp Phe Leu Pro Gly Phe
        195                 200                 205

Glu Ala Ala Ala Ser Ser Ser Ser Phe Pro Glu Leu Asp Tyr Gly Ile
    210                 215                 220

Arg Arg Leu Asp His Ala Val Gly Asn Val Pro Glu Leu Ala Pro Ala
225                 230                 235                 240

Val Arg Tyr Leu Lys Gly Phe Ser Gly Phe His Glu Phe Ala Glu Phe
                245                 250                 255

Thr Ala Glu Asp Val Gly Thr Ser Glu Ser Gly Leu Asn Ser Val Val
            260                 265                 270

Leu Ala Asn Asn Ser Glu Thr Val Leu Leu Pro Leu Asn Glu Pro Val
        275                 280                 285

Tyr Gly Thr Lys Arg Lys Ser Gln Ile Glu Thr Tyr Leu Glu His Asn
    290                 295                 300

Glu Gly Ala Gly Val Gln His Leu Ala Leu Val Thr His Asp Ile Phe
305                 310                 315                 320

Thr Thr Leu Arg Glu Met Arg Lys Arg Ser Phe Leu Gly Gly Phe Glu
                325                 330                 335

Phe Met Pro Ser Pro Pro Pro Thr Tyr Tyr Ala Asn Leu His Asn Arg
            340                 345                 350

Ala Ala Asp Val Leu Thr Val Asp Gln Ile Lys Gln Cys Glu Glu Leu
        355                 360                 365

Gly Ile Leu Val Asp Arg Asp Asp Gln Gly Thr Leu Leu Gln Ile Phe
    370                 375                 380

Thr Lys Pro Val Gly Asp Arg Pro Thr Ile Phe Ile Glu Ile Ile Gln
385                 390                 395                 400

Arg Ile Gly Cys Met Val Glu Asp Glu Glu Gly Lys Val Tyr Gln Lys
                405                 410                 415

Gly Ala Cys Gly Gly Phe Gly Lys Gly Asn Phe Ser Glu Leu Phe Lys
            420                 425                 430

Ser Ile Glu Glu Tyr Glu Lys Thr Leu Glu Ala Lys Arg Thr Ala
        435                 440                 445
```

<210> SEQ ID NO 62
<211> LENGTH: 25
<212> TYPE: DNA
<213> ORGANISM: Artificial Sequence
<220> FEATURE:
<223> OTHER INFORMATION: reverse primer hp2048

<400> SEQUENCE: 62
atctggtacc tgatgttgat gcggc 25

<210> SEQ ID NO 63
<211> LENGTH: 33
<212> TYPE: DNA

<213> ORGANISM: Artificial Sequence
<220> FEATURE:
<223> OTHER INFORMATION: reverse primer hp1791

<400> SEQUENCE: 63
agcctggtac cttgtgtgta aaaaagataa gac 33

<210> SEQ ID NO 64
<211> LENGTH: 895
<212> TYPE: DNA
<213> ORGANISM: Arabidopsis thaliana

<400> SEQUENCE: 64
cgtataaaag aggtaaatat gagacacctt agagatagcg agttaagggt tcaccatcac 60
cacagatgcg tcttaatttt aagtttggct gttgtatgat acgaaattgg acaaacatta 120
agctaggagg catgatggat ttaatcatat tttagatggg aatgagagga tattaaggta 180
ccaaccctca aggcatattg tagactggtt tggtttggac atgtgaagag ttttgaagct 240
gaagtgtttg gtcactctag cattagatgt tgcaggtgta gttttgtaca tacatgtaaa 300
tgatgtctct ttcttacgca catttgttga catagagaag ctaatatttg cttaagcatg 360
ttgtaagctg taactttaga atttaacctc cactgtaaca tattacatat gcaatcaggc 420
aaacgaagat tcgatcaaac gggtcattgc aaatccagaa gtgtgagaag attgaccatt 480
aggaaactta taaagtggtt cagtctttta caaattaaat ttcctgtttc aaacaccaat 540
caaatccacc gaattaccaa agatttcatg tttgcctcta tccataatgg ttggaaaatt 600
ttcaattttt taagtaatag tttgatattg tggggaaaaa atactattct aaacggtaga 660
taggtcttac acgtgagcat tccgtaactg gacaaggatc aaccaaagag aaagcaggga 720
gatccatcac ggaacattat ctttgtaatc aaaatctgat cgtacacgtg tacactatga 780
tgtccactaa cagtccacat ctgttgacct gacattctca gacacacgag aggatctttt 840
ttctttctaa cctctaaaat attttaattt taaaataaaa taataaaatc cgtat 895

<210> SEQ ID NO 65
<211> LENGTH: 1200
<212> TYPE: DNA
<213> ORGANISM: Medicago truncatula

<400> SEQUENCE: 65
atattttgaa aataaacacg ataccaaagt gaaatgtata caaccgttaa aagtacacta 60
agcaaaaatt aagcatattg cctaaattat ctagcataac taataaactg gttcattcat 120
atcaacaaga attgagtgta gatttttact tcactgcata cgagtcttgg ttgagacaaa 180
tgtatacatt tgatgtttga tgtatctcac tgaaaaacaa aaatagaaaa aaaatgacac 240
ttggattaat acgacacttt tagataaatg atgctgacaa tttaaaacta ataagaggta 300
attgtggtgc tcgtaagtat gagcagagtt aagatgatgt ggttggaggc actgatagag 360
aatatgtttt gtagatagat atgaggtgct atgcttgttt ttggcaatgt aaattttgat 420
tggtttctaa caatgtattt aaagaatatg gtgatgagga tgctagattt tagttatatt 480
tttgggcata agtggtttat taattattat ttgtgaggat gtttgatgtg gaacatgctt 540
atcttgtgtt agataaacat ttttcaatat tttatatgtt taacttaaac tttaacggat 600
aaggaaaata tgatgtttat atttgtcgta ttcatacgtt taatatattg tagtcgtttg 660
attgagcttg tgtaattcgt attttaatat aaactatttg atttcgatca aaggactatt 720
aaagcgcaat tgtgacaaac tattcgaact taataattat ttttataaat aagacctaat 780
aaagtaatat ttattctaga gattgcaatt gtcattgcca ttcttatttg aagtttacta 840
acttaggttg ctttaatgaa agttgagtgt ggaggatgtt tttccaattc aatatttcta 900
aaaacattcc aacaaactat agaaagtcgt gtttttcttc tccacttccc atattttttt 960
atttgttgtc tatatcctat gaaattatca tcatcttcac catttttttcc ttcatcctca 1020 tccatccact ctcacacacc atttctccca cgcaacacac aaaactccaa ccacgccgcc 1080
actccattac tctcatccaa tcacattcct ccacgtttca catcccctca acataaaaac 1140
accaacactc ttacaaattc gaacaacaac accaagacaa acactaaaac aacaatctcc 1200

<210> SEQ ID NO 66
<211> LENGTH: 1200
<212> TYPE: DNA
<213> ORGANISM: Poplar

<400> SEQUENCE: 66
tgggttggcc tttatcattt tgatttacaa cagtattcta taccatatta caaaatatat 60
ctttttaatt tattaattta aaaaataaaa aaatattatt ttaatatatt ttcaattaac 120 ttttttttaaa aaaaacacct tacatcacat tactaatata tattactttt gtgtttaagt 180
tcatttaaaa aatttattta acttgaaaaa atattaaatt aattttttct agtttttttt 240
ttggataatt ttgatattat tatataaaaa ataaaaaaaa attaatatat taaaaaaaac 300
acataaaaat cacgtttcat cgcaatacta atgggggtat ttatttttca aaataaaaaa 360
ttccgtgaac tgatctgaac caccaattgt taatgactgt gattcgaaac gtcgttgact 420
tgacagctga accaaggtct agcttttaat ttgtaattta ataagattaa tcgattagtc 480
ctcatagttt ttaatttgtt acaacttact ccctctgtaa tttctctaac tgtgacccat 540
tttgatcttt ccccccctaat atatctctct ttctgactaa attctaatag cattgtaatt 600
ttttcccttc tttttcctca acttttaaac tcttcaacat aaattccata caaaaaaacca 660 agagctattt acctccatca taaattaggt tatgattgga aaggtaaaaa aaaaagaact 720
gtaaagaatt ttcttgaaac taagaatcaa agcagacaaa agaaatccac atgagaaaca 780
attttaaata tctaattatt attaatgaaa taataatcaa agctagttac aggattaata 840
tatagtttat gaaataagaa ggactggtta attaatttta ttaaacaata gagactaagt 900
tataatttac tcatcaacga ggttagaact gaacggtctg tcgccgcata atcccctcta 960
ctcgacaggt gtatctctaa actccagtcg ataaacacga gagcgattaa cttgacacgt 1020
catataaatc cacaggcgtc acgtttcaga atatcttact aaacacgaca agatctgacc 1080
atccccaaac ctccacgtgt acaaggcaat tgacctcaac ttgtaacatt aatttataat 1140
ttaaaaacct gtctccttcc cgttcaaaag gcagcaaacc agaaaaattg agagcaagta 1200

<210> SEQ ID NO 67
<211> LENGTH: 1495
<212> TYPE: DNA
<213> ORGANISM: Brassica rapa

<400> SEQUENCE: 67
ttccgtatgc gctggcaagc atctcttttt gccagtcatt caatttggat cttctcaaag 60
catcagctac tctcacgctg gccgagcttt ggcttggtct tggatcaaat catgccaaac 120
gggcgttaga ccttttgcat ggggctttcc ctatgattct cggccatgga ggtctggagt 180
tacgtgctcg agcatacatc tttgaagcaa actgctatct gtctgaccca agcttttcag 240
gtagcttttg ttgtcttgta cttgctttgg ctatatatag ttcattgtat tggttgcatg 300
atcataattt ttgtatgaat tggctgtgaa tatattccgc cagtttccac agattctgac 360
actgtcctgg attctctgag gcaagcttca gaagagcttc aagctttgga ggtaacttat 420
gccaataaga atgctatgta gcttttgttt cagaaacaag cctgaactct gttctatcgc 480
catattgcat aaacgatgct acgctgctat tggttaaact agatccagct tcggtttagc 540
tcatcgatgc ataatttgtt tcggattcta gtatatcgtg aattaccgtc tgttcacttg 600
ctaatcattg cgtttgttgt ggcagtacca tgaattggca gctgaagctt tttatttaat 660
ggcgatggta tacgacaagg tgggacagct tgaggagagg gaagaagctg cgactttgtt 720
taagatgcat ataacagctc tcgagaaccc tcaagacgag gaaccaaaca tggcgtgaga 780
gttcgtgacc ttatttaata agcttattgt gcaaagcttg taacttaagt tgtaacatgt 840
tccttgagac tttctagtga tttgtaggtt tatttcatga ccgagagcaa gtagcaacct 900
ttcataactt tgaaatgtag gaaattttag aagccaacta agtgatttga gaaattttct 960
tatgtaatac ctaacataat ctctgttttt aaatcgctga attgggatat gaacgtaatg 1020
atgtactact gtacatggga tgattccaag gtttgaacaa cgtcgatcga aaggtaaaat 1080
gtcacttgaa atatataact atcaaaccac ttttgcttca tcatcaatac tcatccatat 1140
ggttcggata acgtttccat caacgtgtca aaatggtaga tacgtcttac acatcagaac 1200
ttggtgacca tagacaagga gaaagaacga accaatcagc ttaaggtcaa gcaaactaga 1260
gagagatcca tcacgtaaag ctttgtttct aatgaaaatc tgaccgtaca cgtgtgttct 1320
tccacgtcca acaatagtca acatctgtga gttttaagac cagagataac gtctgaataa 1380
actgatatta aaacaaaaca aaatcctttt atatgtgtcc gtgtccatag ctcaacgaac 1440
cactcacaca gttccgtaag cagagtatag ttgcatcaga aggtgaaaaa caccc 1495

<210> SEQ ID NO 68
<211> LENGTH: 1402
<212> TYPE: DNA
<213> ORGANISM: Vitis vinifera

<400> SEQUENCE: 68
attgtgatgt tatatttggg ttgattggat tagacttagg ttagttgaaa tatataattt 60
aaaatccata atatttttaa aaagaaaact tttttcttta tatttatacc aaaatttaaa 120
tagtaattat gacaaaattt caagataaca acaaaaaaga aaaataaatt tatatatctt 180
tctaaaaaag aaaaatatat atgatacaat gtaatttgat attttaaaaa aaactaaaaa 240
gaaaatgaat attattatat agaataaaat acattataaa tgttataaaa acattaactt 300
gagttaggtt aggctcaaat tgtgttaatc atgacctcta ctcaatcata atattaaaaa 360
taatttccta aacttgccca aatgatgagc taggtagagt caacggccta tgttgcaccc 420
ctttaataga atcattctat attaagaaaa tatgtatatt ataactaaca atataatata 480
atatttttat ttttaaactc cagatatttt aatcataaat aagtttttca ttcctatttt 540
tctttcttat tttataaatt aaacataaat atgatgtaat atatcccatt gaatatatta 600
ctttctaaga tcattccacc ggatataata tctaaaaata tcatacttaa ctaaaaatga 660
tgttatagga tatgtttata ttatataata taaaaaaaaa tatcatattc aattaaaaat 720
aaaaaatgca caaacatact aatacaaagt atcatattca attcaaaatg atatatatat 780
atatattcat cttgggtaac caaaccccac ttgtattagc acaccataat ggaaatgata 840
acataatcga atttgtagtg aatcataata tatgtaaaaa agatgactta aaatctcgat 900
aaaagtgaat atgaaaataa atttttaagt tttattttta tttttaaaaa gattaatttt 960
cttttaagta tgtttagtta atcattatct tggataatta tatttttaa atatttattt 1020 atttatttaa ctttgctttt tgattaggtg tgtgtcgttg catccaaatc atattttatt 1080
ttaaatatat aaatgataat attttactta tatcagtatt ttttatattt gtaatattta 1140
tatttattaa cttattttat attatttgct tttttttctc ttttttttt caatttttca 1200 aaaaagaatt ttcattttta aaatatgttt tgaaaaacat tatgttttat atttttgacc 1260
gcagagaatt gttatgttag tgtcgtatac ttttgtccct gaacggaaaa ccgtttttta 1320
aaataaccgc ggaatgtacg tagaccatcg tcattgagat aagcatacgc tattgaaaaa 1380
gcaaacaaga taaatcactc ca 1402

<210> SEQ ID NO 69
<211> LENGTH: 1100
<212> TYPE: DNA
<213> ORGANISM: Sorghum bicolor

<400> SEQUENCE: 69
tgggctcaag tagaggccct gctgaagttg ctcttaggac actccgagcc ctcccaatgc 60
tagaaactat acatagttcc tatacctatt aatttccata aacactacat atagaaatca 120
tggttccaat agatagtttt tatataataa ttttttatcc aatcatattc attctcttcc 180
cattctcaac caatcacatc acttcatgtc ttggttctgg tgtagacatg gtttctaact 240
tagatccggt ttcttttatt tttgctctat cttttcaata actatcttgc cacattagca 300
aaatgcttag gagtttttgc aacgagagtg accttagcaa tcataatagc tagctagtta 360
ataggtcata attattgtta gatgctatta actactttgg ttcaactagt aaaaattagt 420
tgctaaccga atattcagct aacagttagc taaactataa actatacagt atagagaaaa 480
aaaaagcaaa ctactatctt cttagattag atcaaagggg gcctaaaacg aattacacaa 540
taaaggaaaa tagaactcca cacctttctt gtaggcaact ccacaaaaaa ttaaccacaa 600
catttcgatt ttcgttcccc attttccaca ggccttgttg agttcggatt tcccgtcaca 660
tcgaatttta tggcacatac atagaacttt aaatataaat aaaataaata actaatttta 720
atttgtgaga cgaatttttt gagcgtagtt agttaatgat tgaacaatat ttattaaata 780
taaacaaaag tgctatagtg tttattttgc aaaaatgttt taaaactaaa caaaaggctg 840
ttggtgccct agggccggtc agcaacttca tcagcttcac atcactacaa gctgtgaagg 900
agccactcac caacaaatac cagaagacaa atcacatccg caaccacaga attttctgtc 960
cacgtggccc catcaccacc ctttatttac cccgtcagtc atccctcatc ccagggtcac 1020
tcaccggtca gccaagcgca cctgcaactg caaagctgcg gaggccgcca cgccgccacg 1080
ccctccgaga gccaagcaca 1100

<210> SEQ ID NO 70
<211> LENGTH: 72
<212> TYPE: DNA
<213> ORGANISM: Artificial Sequence
<220> FEATURE:
<223> OTHER INFORMATION: SynII core

<400> SEQUENCE: 70
ggatccactc gagcggctat aaatacgtac ctacgcacgc tgcgctacca tcccgagcac 60
tgcagtgtcg ac 72

<210> SEQ ID NO 71
<211> LENGTH: 41
<212> TYPE: DNA
<213> ORGANISM: Artificial Sequence
<220> FEATURE:
<223> OTHER INFORMATION: Partial SynII core

<400> SEQUENCE: 71
cggctataaa tacgtaccta cgcacgctgc gctaccatcc c 41

<210> SEQ ID NO 72
<211> LENGTH: 30
<212> TYPE: DNA
<213> ORGANISM: Glycine max
<220> FEATURE:
<221> NAME/KEY: 5'UTR
<222> LOCATION: (1)...(30)
<223> OTHER INFORMATION: predicted 5' UTR

<400> SEQUENCE: 72
aatctcaagc agcagcatca caccacacca 30

<210> SEQ ID NO 73
<211> LENGTH: 96
<212> TYPE: DNA
<213> ORGANISM: Artificial Sequence
<220> FEATURE:
<223> OTHER INFORMATION: Rsyn7

<400> SEQUENCE: 73
ggatcctatg cgtatggtat gacgtgtgtt caagatgatg acttcaaacc tacctatgac 60
gtatggtatg acgtgtgtcg actgatgact tagatc 96

<210> SEQ ID NO 74
<211> LENGTH: 2038
<212> TYPE: DNA
<213> ORGANISM: Artificial Sequence
<220> FEATURE:
<223> OTHER INFORMATION: SHP120C

<400> SEQUENCE: 74
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900

```
ttatctatat aagcttatta aattaaattt atgtgcaata gtgacccctg atcttctgta    960
attatcattc aatagctgta gtcattttgt ttccaattgt aaccgtagcc aagatgtacg   1020
gtggcataaa ccttggagat attttgttct ctcttccctt catagaggac aaccttcatg   1080
taatggacat actaacgaca attaaattat ttatcatttt aaaagattaa atatttttc   1140
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt tttttaaaa aaaaagaaga taaatataga   1680
agaaaaggat gtgataaagg caagagaagc gtgtgaacaa gagagagacg aatctaggtg   1740
gatttgacgt acgttgaatg aatgttgaat ataagtaata acgctgaggc tgtaggtgtg   1800
ggtaataaaa aaagagagaa gccgcatcaa catcatccaa tatttggacg ttaaaagagc   1860
gtcgtaatcc atttccattt ctcatctatc ttcacttcct cgtcctcatc ctcatccacc   1920
tattctcaac ccagacgcaa tgcccatgta cactccatca ctctccgcac cctcctccaa   1980
tcacattcaa ccaagtgtca cactcccctt atatatcaca accaccaagc tcaatctc     2038
```

<210> SEQ ID NO 75
<211> LENGTH: 2038
<212> TYPE: DNA
<213> ORGANISM: Artificial Sequence
<220> FEATURE:
<223> OTHER INFORMATION: SHP121C

<400> SEQUENCE: 75

```
gggtgttgat cctttttctc tccccttgtt ggggctttaa ctgaatctta cttgactgat     60
ttgaatttct ttttcagtct ttgaaaatta tgagattgtg atagattcat tgagacaagc    120
atctgaagaa ctccaacttt tggaggtatg caaactttct gccttttaat cttttgtgta    180
atcccttgtg agaggaagaa aaatgagagt tcatgtgaat gaatgtgtct tgactacaca    240
gtggagactc ttatttataa ttagaactgc aaatacagta gataattgtc atataattat    300
acaactcata atatccctaa tttacaatac ttcttttaca caatatatta cataattaca    360
agcttccgaa cagttgtcat tggtcctttt tcatttgtaa gcctttttgc tgcatctctg    420
cttcccgcca aagttcactt ggatacatga ttgcatgctt gtgatagatg ctagagttgt    480
gtaaagcgta aaatgaagta gggatgactg tcgcaatgaa aaaccagtgc aaaccaaaag    540
cagaggcata cattatattc gggcatatag atactggata aatgtttatc aaattgattt    600
tatggggtct taatacttgc aagatttatg ttgtgatggt gaaagctcac tagtcttaat    660
acacccaaat ccccttctat tgctttttat ttaagatttg attttcttgc agtttcatga    720
actggcagct gaagctttct atctgatggc catggtatat gacaaactgg ggcaattaga    780
agaaagggaa gaagctgcag cttcatttca gaaacatatt ttggctctcc gcaatcctca    840
agatgaggat gatcctcttg ttagtgtgtt ttgattgttc tttatagttt atacctaatt    900
```

-continued

```
ttatctatat aagcttatta aattaaattt atgtgcaata gtgacccctg atcttctgta    960

attatcattc aatagctgta gtcattttgt ttccaattgt aaccgtagcc aagatgtacg   1020

gtggcataaa ccttggagat attttgttct ctcttccctt catagaggac aaccttcatg   1080

taatggacat actaacgaca attaaattat ttatcatttt aaaagattaa atattttttc   1140

ttaaattatt cctgtgcttt aaaattctta acagaaaatt taaaattaga catttgtacc   1200

attagagaaa aactgtggga ctcatttgtt tattagatta tttcagctag caactgactc   1260

tcttgtacat ttcattttta cattccttta attatgcatc attaacagta gtagattgca   1320

tctcttaaaa aaaaaattag attgcagtat tgccttggaa atatggaatt acaatgtcaa   1380

aatattttaa cgaataacga tgcgtagctt aaagttcaag acacaatttt aacgttatat   1440

agtgcatcaa tgtttgaaat tttagtgtat aaataacgta tttttgataa tattttttac   1500

acaacaatcc tcttaaattt tcttatctta tttcatttaa ccgttctctt aaattgtctt   1560

atctttttta cacacaaatg aatcccaata aacatggttg ggatttattt gagttcttaa   1620

ctttaggaac caaatatata ataatttttt tttttaaaa aaaaagaaga taaatataga   1680

agaaaaggat gtgataaagg caagagaagc gtgtgaacaa gagagagacg aatctaggtg   1740

gatttgacgt acgttgaatg aatgttgaat ataagtaata acgctgaggc tgtaggtgtg   1800

ggtaataaaa aaagagagaa gccgcatcaa catcatccaa tatatggacg ttaaaagagc   1860

gtcgtaatcc atttccattt ctcatctatc ttcacttcct cgtcctcatc ctcatccacc   1920

tattctcaac ccagacgcaa tgcccatgta cactccatca ctctccgcac cctcctccaa   1980

tcacattcaa ccaagtgtca cactcccctt atatatcaca accacctagc tcaatctc     2038
```

<210> SEQ ID NO 76
<211> LENGTH: 1801
<212> TYPE: DNA
<213> ORGANISM: Artificial Sequence
<220> FEATURE:
<223> OTHER INFORMATION: SHP122C

<400> SEQUENCE: 76

```
gggtgttgat cctttttctc tccccttgtt ggggctttaa ctgaatctta cttgactgat     60

ttgaatttct ttttcagtct ttgaaaatta tgagattgtg atagattcat tgagacaagc    120

atctgaagaa ctccaacttt tggaggtatg caaactttct gccttttaat cttttgtgta    180

atcccttgtg agaggaagaa aaatgagagt tcatgtgaat gaatgtgtct tgactacaca    240

gtggagactc ttatttataa ttagaactgc aaatacagta gataattgtc atataattat    300

acaactcata atatccctaa tttacaatac ttcttttaca caatatatta cataattaca    360

agcttccgaa cagttgtcat tggtcctttt tcatttgtaa gcctttttgc tgcatctctg    420

cttcccgcca aagttcactt ggatacatga ttgcatgctt gtgatagatg ctagagttgt    480

gtaaagcgta aaatgaagta gggatgactg tcgcaatgaa aaaccagtgc aaaccaaaag    540

cagaggcata cattatattc gggcatatag atactggata aatgtttatc aaattgattt    600

tatggggtct taatacttgc aagatttatg ttgtgatggt gaaagctcac tagtcttaat    660

acacccaaat ccccttctat tgctttttat ttaagatttg attttcttgc agtttcatga    720

actggcagct gaagctttct atctgatggc catggtatat gacaaactgg ggcaattaga    780

agaaagggaa gaagctgcag cttcatttca gaaacatatt ttggctctcc gcaatcctca    840

agatgaggat gatcctcttg ttagtgtgtt ttgattgttc tttatagttt atacctaatt    900

ttatctatat aagcttatta aattaaattt atgtgcaata gtgacccctg atcttctgta    960
```

attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atatttttc 1140 ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt ttttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
g 1801

<210> SEQ ID NO 77
<211> LENGTH: 2053
<212> TYPE: DNA
<213> ORGANISM: Artificial Sequence
<220> FEATURE:
<223> OTHER INFORMATION: SHP111

<400> SEQUENCE: 77
gggtgttgat ccttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180
atcccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atatttttc 1140 ttaaattatt cctgtgcttt aaaattctta acagaaaatt taaaattaga catttgtacc 1200
attagagaaa aactgtggga ctcatttgtt tattagatta tttcagctag caactgactc 1260
tcttgtacat ttcattttta cattccttta attatgcatc attaacagta gtagattgca 1320
tctcttaaaa aaaaaattag attgcagtat tgccttggaa atatggaatt acaatgtcaa 1380
aatattttaa cgaataacga tgcgtagctt aaagttcaag acacaatttt aacgttatat 1440
agtgcatcaa tgtttgaaat tttagtgtat aaataacgta tttttgataa tattttttac 1500
acaacaatcc tcttaaattt tcttatctta tttcatttaa ccgttctctt aaattgtctt 1560
atctttttta cacacaaatg aatcccaata aacatggttg ggatttattt gagttcttaa 1620
ctttaggaac caaatatata ataatttttt tttttaaaa aaaaagaaga taaatataga 1680
agaaaaggat gtgataaagg caagagaagc gtgtgaacaa gagagagacg aatctaggtg 1740
gatttgacgt acgttgaatg aatgttgaat ataagtaata acgctgaggc tgtaggtgtg 1800
ggtaataaaa aaagagagaa gccgcatcaa catcatccaa tatatggacg ttaaaagagc 1860
gtcgtaatcc atttccattt ctcatctatc ttcacttcct cgtcctcatc ctcatccacc 1920
tattctcaac ccagacgcaa tgcccatgta cactccatca ctctccgcac cctcctccaa 1980
tcacattcaa ccaagtgtca cactcactcg agcggctata aatacgtacc tacgcacgct 2040
gcgctaccat ccc 2053

<210> SEQ ID NO 78
<211> LENGTH: 2145
<212> TYPE: DNA
<213> ORGANISM: Artificial Sequence
<220> FEATURE:
<223> OTHER INFORMATION: SHP210

<400> SEQUENCE: 78
gggtgttgat cctttttctc tccccttgtt ggggctttaa ctgaatctta cttgactgat 60
ttgaatttct ttttcagtct ttgaaaatta tgagattgtg atagattcat tgagacaagc 120
atctgaagaa ctccaacttt tggaggtatg caaactttct gccttttaat cttttgtgta 180 atccccttgtg agaggaagaa aaatgagagt tcatgtgaat gaatgtgtct tgactacaca 240
gtggagactc ttatttataa ttagaactgc aaatacagta gataattgtc atataattat 300
acaactcata atatccctaa tttacaatac ttcttttaca caatatatta cataattaca 360
agcttccgaa cagttgtcat tggtcctttt tcatttgtaa gcctttttgc tgcatctctg 420
cttcccgcca aagttcactt ggatacatga ttgcatgctt gtgatagatg ctagagttgt 480
gtaaagcgta aaatgaagta gggatgactg tcgcaatgaa aaaccagtgc aaaccaaaag 540
cagaggcata cattatattc gggcatatag atactggata aatgtttatc aaattgattt 600
tatggggtct taatacttgc aagatttatg ttgtgatggt gaaagctcac tagtcttaat 660
acacccaaat ccccttctat tgctttttat ttaagatttg attttcttgc agtttcatga 720
actggcagct gaagctttct atctgatggc catggtatat gacaaactgg ggcaattaga 780
agaaagggaa gaagctgcag cttcatttca gaaacatatt ttggctctcc gcaatcctca 840
agatgaggat gatcctcttg ttagtgtgtt ttgattgttc tttatagttt atacctaatt 900
ttatctatat aagcttatta aattaaattt atgtgcaata gtgacccctg atcttctgta 960
attatcattc aatagctgta gtcattttgt ttccaattgt aaccgtagcc aagatgtacg 1020
gtggcataaa ccttggagat attttgttct ctcttccctt catagaggac aaccttcatg 1080
taatggacat actaacgaca attaaattat ttatcatttt aaaagattaa atattttttc 1140

```
ttaaattatt cctgtgcttt aaaattctta acagaaaatt taaaattaga catttgtacc   1200
attagagaaa aactgtggga ctcatttgtt tattagatta tttcagctag caactgactc   1260
tcttgtacat ttcattttta cattccttta attatgcatc attaacagta gtagattgca   1320
tctcttaaaa aaaaaattag attgcagtat tgccttggaa atatggaatt acaatgtcaa   1380
aatattttaa cgaataacga tgcgtagctt aaagttcaag acacaatttt aacgttatat   1440
agtgcatcaa tgtttgaaat tttagtgtat aaataacgta tttttgataa tattttttac   1500
acaacaatcc tcttaaattt tcttatctta tttcatttaa ccgttctctt aaattgtctt   1560
atctttttta cacacaaatg aatcccaata aacatggttg ggatttattt gagttcttaa   1620
ctttaggaac caaatatata ataatttttt tttttaaaa aaaaagaaga taaatataga   1680
agaaaaggat gtgataaagg caagagaagc gtgtgaacaa gagagagacg aatctaggtg   1740
gatttgacgt acgttgaatg aatgttatcc tatgcgtatg gtatgacgtg tgttcaagat   1800
gatgacttca aacctaccta tgacgtatgg tatgacgtgt gtcgactgat gacttagatc   1860
cactcgagcg gctataaata cgtacctacg cacgctgcgc taccatccca ataaaaaaag   1920
agagaagccg catcaacatc atccaatata tggacgttaa aagagcgtcg taatccattt   1980
ccatttctca tctatcttca cttcctcgtc ctcatcctca tccacctatt ctcaacccag   2040
acgcaatgcc catgtacact ccatcactct ccgcaccctc ctccaatcac attcaaccaa   2100
gtgtcacact ccccttatat atcacaacca ccaagctcaa tctca                   2145
```

<210> SEQ ID NO 79
<211> LENGTH: 1341
<212> TYPE: DNA
<213> ORGANISM: Glycine max

<400> SEQUENCE: 79

```
atgccaatac ccatgtgcaa cgaaattcaa gcccaagccc aagcccaagc ccaacctggg     60
tttaagctcg tcggtttcaa aaacttcgtc cgaaccaatc ctaagtcgga ccgctttcaa    120
gtcaaccgct tccaccacat cgagttctgg tgcaccgatg ccaccaacgc ctctcgccga    180
ttctcttggg gacttggaat gcctattgtg gcaaaatctg atctctccac cggaaaccaa    240
atccacgcct cctacctcct ccgctccggc gacctctcct tcctcttctc cgctccttac    300
tctccctctc tctccgccgg ctcctccgct gcctcctccg cctccattcc cagtttcgac    360
gccgccacct gccttgcctt cgctgccaaa cacggcttcg gcgtccgcgc catcgccttg    420
gaagtcgccg acgcggaagc cgctttcagc gccagcgtcg cgaaaggagc cgagccggcg    480
tcgccgccgg ttctcgtcga cgatcgcacc ggcttcgcgg aggtgcgcct ctacggcgac    540
gtggtgctcc gctacgtcag ctacaaggac gccgcgccgc aggcgccaca cgcagatccg    600
tcgcggtggt tcctgccggg attcgaggcc gcggcgtcgt cgtcttcgtt tccggagctg    660
gactacggga tccggcggct ggaccacgcc gtcgggaacg ttccggagct ggcgccggcg    720
gtgaggtacc tgaaaggctt cagcggattc cacgagttcg cggagttcac cgcggaggac    780
gtgggaacga gcgagagcgg gttgaactcg gtggttctgg cgaacaactc ggagacggtg    840
ttgctgccgc tgaacgagcc ggtttacgga acgaagagga agagccagat tgagacgtat    900
ttggaacaca acgaaggtgc tggtgtgcag caccttgcgc ttgttactca cgacatcttc    960
accacactga gagagatgag aaagcgaagt ttccttggtg gatttgagtt catgccttct   1020
```

-continued

```
cctcctccca cctattacgc caacctccac aaccgtgccg ctgatgtgtt gaccgttgac   1080

cagattaagc agtgtgagga gcttgggatt cttgttgaca gagatgatca gggcactctg   1140

cttcagattt tcactaagcc tgttggggac aggccaacga tattcataga gataattcag   1200

aggatcgggt gcatggtgga ggatgaggaa gggaaggtgt accagaaggg tgcatgtggg   1260

ggttttggga aaggcaattt ttctgagctt ttcaaatcca ttgaagaata tgagaagact   1320

ttggaagcta aaagaaccgc g                                              1341


<210> SEQ ID NO 80
<211> LENGTH: 50
<212> TYPE: PRT
<213> ORGANISM: Glycine max

<400> SEQUENCE: 80

Met Pro Met Tyr Thr Pro Ser Leu Ser Ala Pro Ser Ser Asn His Ile
 1               5                  10                  15

Gln Pro Ser Val Thr Leu Pro Leu Tyr Ile Thr Thr Thr Lys Leu Asn
            20                  25                  30

Leu Lys Gln Gln His His Thr Thr Pro Met Pro Ile Pro Met Cys Asn
        35                  40                  45

Glu Ile
    50


<210> SEQ ID NO 81
<211> LENGTH: 7
<212> TYPE: PRT
<213> ORGANISM: Glycine max

<400> SEQUENCE: 81

Met Asp Val Lys Arg Ala Ser
 1               5


<210> SEQ ID NO 82
<211> LENGTH: 9
<212> TYPE: PRT
<213> ORGANISM: Glycine max

<400> SEQUENCE: 82

Met Pro Ile Pro Met Cys Asn Glu Ile
 1               5


<210> SEQ ID NO 83
<211> LENGTH: 145
<212> TYPE: DNA
<213> ORGANISM: Artificial Sequence
<220> FEATURE:
<223> OTHER INFORMATION: Synthetic Element III

<400> SEQUENCE: 83

ttatcctatg cgtatggtat gacgtgtgtt caagatgatg acttcaaacc tacctatgac     60

gtatggtatg acgtgtgtcg actgatgact tagatccact cgagcggcta taaatacgta    120

cctacgcacg ctgcgctacc atccc                                          145
```

CHIMERIC PROMOTERS AND METHODS OF USE

CROSS-REFERENCE TO RELATED APPLICATION

This application claims the benefit of U.S. Provisional Application Ser. No. 61/401,456, filed Aug. 13, 2010; U.S. Provisional Ser. No. 61/393,507, filed Oct. 15, 2010; and, U.S. Provisional Ser. No. 61/501,042, filed Jun. 24, 2011; each of which is herein incorporated by reference.

FIELD OF THE INVENTION

The invention relates to the field of genetic manipulation of plants, particularly the modulation of gene activity in plants.

REFERENCE TO A SEQUENCE LISTING SUBMITTED ON COMPACT DISK

The official copy of the sequence listing is submitted electronically via EFS-Web as an ASCII formatted sequence listing with a file named 408392SEQLIST.txt, created on Aug. 12, 2011, and having a size of 139 KB and is filed concurrently with the specification. The sequence listing contained in this ASCII formatted document is part of the specification and is herein incorporated by reference in its entirety.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Modifications of the promoter sequences or additional regulatory sequences upstream and/or downstream from the promoter sequence may be included in expression constructs to bring about varying levels of expression of heterologous nucleotide sequences of interest in a transgenic plant.

Frequently it is desirable to modulate the level of expression of a nucleotide sequence of interest along with the temporal and spatial expression of the nucleotide sequence of interest in a plant. For example, increased resistance of a plant to infection by soil- and air-borne pathogens might be accomplished by genetic manipulation of the plant's genome to comprise a tissue-preferred promoter operably linked to a heterologous herbicide-resistance gene or heterologous pathogen-resistance gene. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Thus, isolation and characterization of promoter sequences that allow varying levels of expression, locations of expression, and inducible expression conditions of heterologous nucleotide sequences of interest in a transgenic plant are needed for genetic manipulation of plants.

BRIEF SUMMARY OF THE INVENTION

Compositions and methods comprising promoters from the 4-hydroxyphenylpyruvate dioxygenase (HPPD) gene and active variants and fragments thereof, as well as chimeric promoters employing regulatory regions of the HPPD promoters are provided. Further provided are expression cassettes and plants comprising the various promoters disclosed herein operably linked to a polynucleotide of interest. Methods employing the various promoters described herein to modulate the expression of polynucleotides of interest are further provided.

BRIEF DESCRIPTION OF THE DRAWINGS

FIG. 1 shows the conserved regions of the *Glycine max* HPPD gene promoter sequence (SEQ ID NO:1) (~1.2 Kbp shown upstream of predicted start of translation). Shaded motifs indicate some level of conservation among sequenced genomes, with bold having highest weight, and italic medium. The predicted TATA boxes are shown in boxes. Predicted transcription start site (TSS) "A" is shown bold and underlined. Experimentally determined transcription start sites "G" and "A" at position −231 and +7 relative to predicted TSS and the predicted translation start codons are shown underlined.

FIG. 8 shows schematics of the chimeric promoters described herein comprising a regulatory region of an HPPD promoter operably linked to synthetic element I (SEQ ID NO: 21). TATA motifs are indicated by T1 (TATA1), T2 (TATA2), T3 (TATA3), T4 (TATA4), and T5 (TATA5). Nucleotide point mutations are indicated by a "*" within the appropriate TATA motif.

(TATA2), T3 (TATA3), T4 (TATA4), and T5 (TATA5). Nucleotide point mutations are indicated by a "*" within the appropriate TATA motif.

Figure 10:
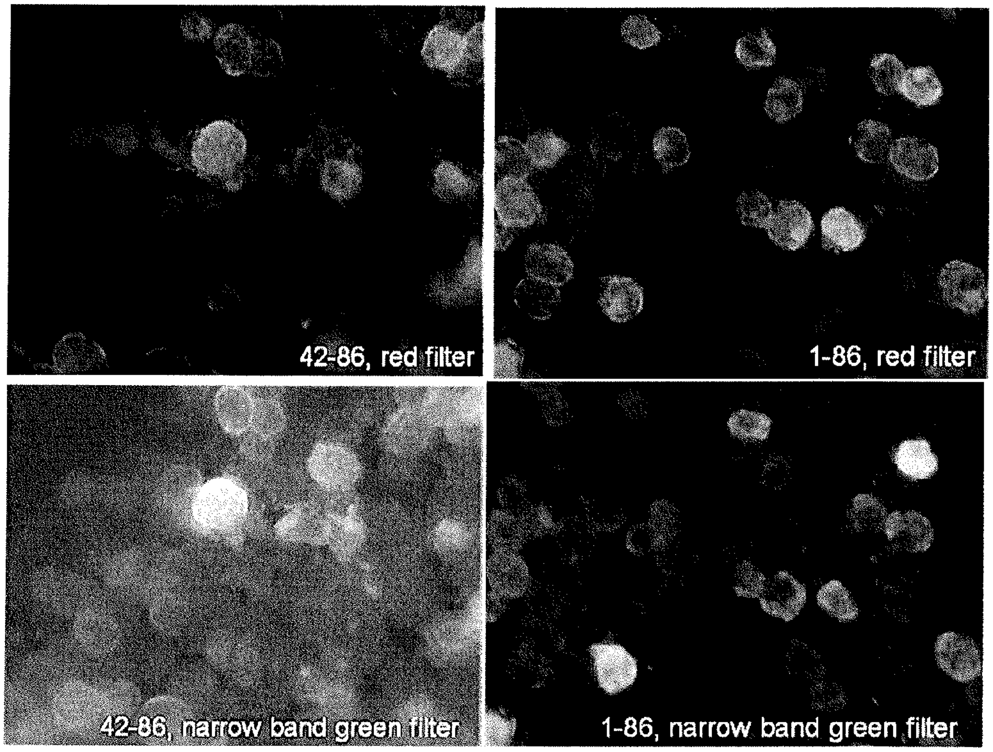

FIG. 10 shows transient expression of Gm HPPD-AcGFP fusion proteins in soy leaf cells. Epifluorescence micrographs of soy leaf sections infiltrated with both untargeted (cytoplasmic) DsRed2 and Gm-HPPD N terminus fusions to AcGFP. A and C. With both vectors red fluorescence is seen in the cytoplasm while plastids remain dark. B. When AcGFP is fused to Gm-HPPD amino acids 42-86 (from SEQ ID NO: 58), green fluorescence is seen in the cytoplasm and plastids remain dark. D. When AcGFP is fused to Gm HPPD amino acids 1-86 (from SEQ ID NO: 58), green fluorescence is clearly seen in plastids of infected cells.

Figure 11:
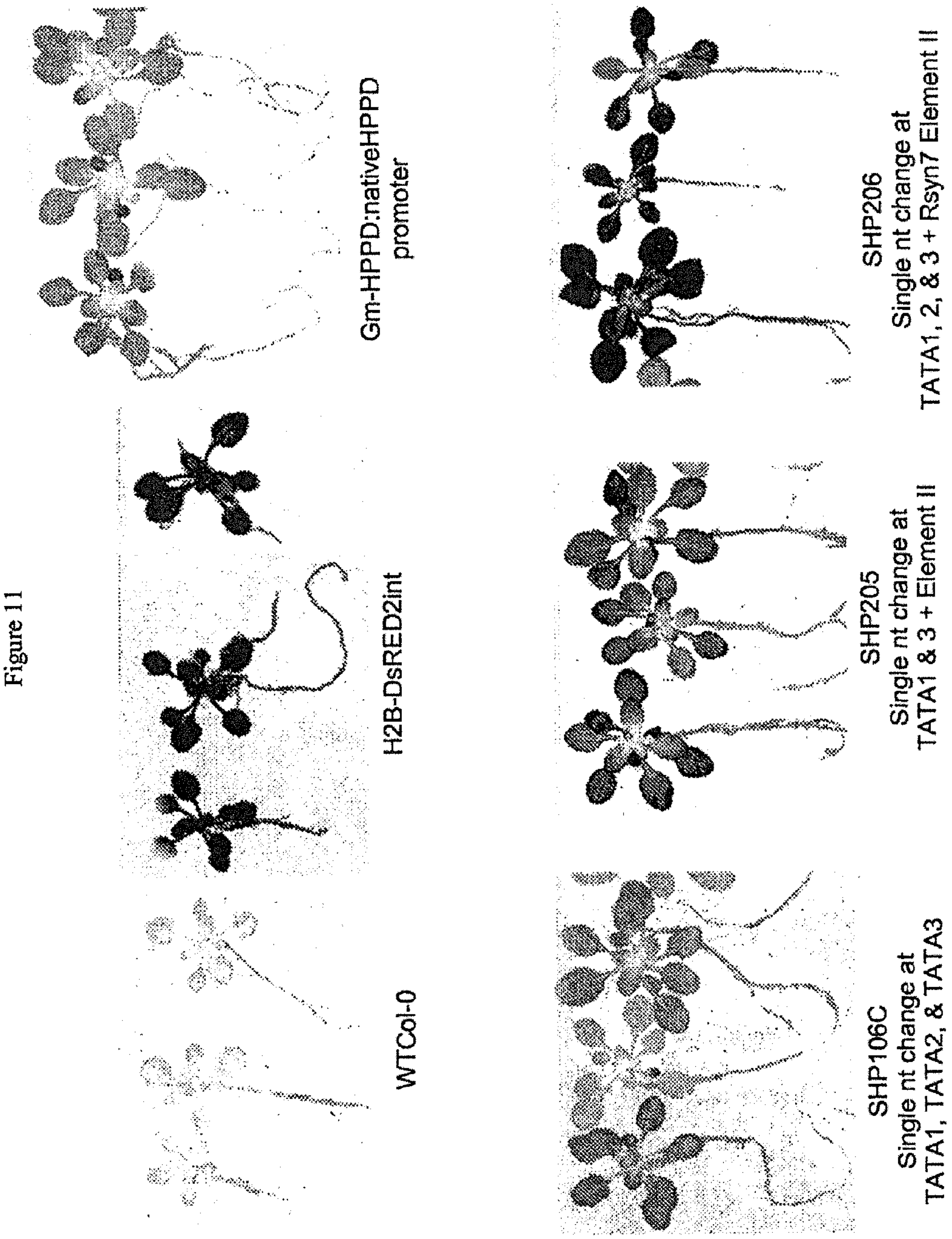

FIG. 11 depicts the pattern and relative level of DsRed2 expression detected by Typhoon variable mode imager from 24 day old stably transformed *Arabidopsis* plants indicating expression pattern and level of "wild-type" Col-0 (background fluorescence), H2B promoter, native GM-HPPD promoter and synthetic variants SHP106C, SHP205 and SHP206.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

Compositions disclosed herein provide HPPD promoters and chimeric promoters comprising a regulatory region of an HPPD promoter operably linked to a core promoter. The various promoters and chimeric promoters disclosed herein have "transcription regulatory activity" or "promoter activity". As used herein, "transcriptional regulatory activity" or "promoter activity" refers to the ability of a polynucleotide to direct the transcription of a polynucleotide of interest. Methods are available in the art for determining if a promoter sequence retains the ability to direct transcription. Such activity can be measured by Northern blot analysis. See, for example, Sambrook et al. (1989) *Molecular Cloning: A Laboratory Manual* (2d ed., Cold Spring Harbor Laboratory Press, Plainview, N.Y.), herein incorporated by reference. Alternatively, biological activity of the promoter can be measured using assays specifically designed for measuring the activity and or level of the polypeptide being expressed from the promoter. Such assays are known in the art. For example, transcriptional regulatory activity of the HPPD promoter and/or chimeric promoters and/or regulatory regions of an HPPD promoter or active fragments and variants thereof can be determined by measuring the activity or level of a polynucleotide of interest expressed from the HPPD promoter and/or chimeric promoters and/or regulatory regions of an HPPD promoter. Methods for measuring the activity and level of polynucleotides of interest are disclosed elsewhere herein.

By "modulating" the transcriptional regulatory activity is intended to mean the transcriptional regulatory activity of the promoter sequence is either increased or decreased when compared to an appropriate control. A decrease in transcriptional regulatory activity is intended to mean the transcription regulatory activity of the promoter is statistically lower than the activity of an appropriate control. An increase in transcriptional regulatory activity is intended to mean the transcription regulatory activity of the promoter is statistically higher than the activity of an appropriate control.

In particular embodiments, modulating the transcriptional regulatory activity results in at least a 95% decrease or increase, at least a 90% decrease or increase, at least a 80% decrease or increase, at least a 70% decrease or increase, at least a 60% decrease or increase, at least a 50% decrease or increase, at least a 40% decrease or increase, at least a 30% decrease or increase, at least a 20% decrease or increase, at least a 10% decrease or increase, or at least a 5% decrease or increase of the transcriptional regulatory activity of the promoter or active variant or fragment thereof when compared to an appropriate control. Alternatively, modulating the transcriptional regulatory activity can include about a 0.5 fold, 1 fold, 2 fold, 4 fold, 8 fold, 16 fold, or 32 fold overall decrease or increase of the transcriptional regulatory activity of the promoter or active variant or fragment thereof when compared to an appropriate control. In other embodiments, modulating the transcriptional regulatory activity of a promoter or active variant or fragment thereof results in a decrease or an increase in the transcription regulatory activity of about 3%-15%, 10%-25%, 20%-35%, 30%-45%, 40%-55%, 50%-65%, 60%-75%, 70%-90%, 70% to 80%, 70%-85%, 80%-95%, 90%-100% when compared to an appropriate control.

It is further recognized that the modulation of the transcriptional regulatory activity need not be an overall increase or decrease in activity but also includes a change in tissue distribution of the regulatory activity, a modification of the location within a cell of the product of the gene regulated by the promoter, or an alteration in response to specific inducing factors. If multiple transcripts are produced from a single polynucleotide sequence, modulation of the transcriptional regulatory activity could alter the native ratio of transcripts to increase one in relation to the other transcript or other transcripts.

A. Hydroxyphenylpyruvate Dioxygenase (HPPD) Promoters

Various promoters and active variants and fragments thereof from the hydroxyphenylpyruvate dioxygenase (HPPD) gene are provided herein. As used herein, an "HPPD promoter" encompasses the genomic region including and upstream of the transcription start site (TSS), including the furthest downstream TSS in the case of multiple TSS, and may include the untranslated region of the transcript up to the ATG, for a gene encoding HPPD. In specific embodiments, an HPPD promoter can comprise the genomic region found 5' to the translational start site. Such HPPD promoters include SEQ ID NO: 1, which comprises the native polynucleotide sequence of the *Glycine max* (soy) HPPD promoter, and active variants and fragments thereof. As used herein, a "native" or "wild type" polynucleotide comprises any naturally occurring nucleotide sequence. As discussed in further detail elsewhere herein, such HPPD promoters and active variants and fragments thereof find use in expression of polynucleotides of interest, and further when modified or constructed into a chimeric promoter, the expression profile (i.e.

temporal expression, tissue specific expression, or expression level) can be modulated. Such alterations in expression find use when one desires to refine the level or pattern of expression of a polynucleotide of interest.

Various compositions are provided which employ HPPD promoters and active fragments and variants thereof. As used herein, a "promoter" is a regulatory region of DNA usually comprising a TATA box capable of directing RNA polymerase II to initiate RNA syntheses at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences disclosed herein modulate transcription of an operably linked polynucleotide of interest. In one embodiment, novel promoters set forth in SEQ ID NO: 1, 2, 3, 4, 5, 6, 7, 8, 9, 10, 11, 12, 13, 14, 15, 16, 17, 18, 19, 20, 23, 24, 25, 26, 27, 28, 29, 30, 31, 32, 33, 34, 35, 36, 37, 38, 39, 40, 41, 74, 75, 76, 77, and 78 and variants and fragments thereof having transcriptional regulatory activity are provided.

The HPPD promoters and the active variants and fragments of the HPPD promoters disclosed herein have transcriptional regulatory activity. The transcriptional regulatory activity of the HPPD promoter or active variants and fragments thereof can reflect either an increase in transcriptional regulatory activity or a decrease in transcription regulatory activity when compared to a native HPPD promoter (such as the native soy HPPD promoter as set forth in SEQ ID NO:1). For example, an HPPD promoter or active variant or fragment thereof can regulate transcription of an operably linked polynucleotide. In specific embodiments, the HPPD promoter or active variant or fragment thereof has an increase or a decrease in transcriptional regulatory activity of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, or greater when compared to the transcriptional regulatory activity of a native HPPD promoter or to the native soy HPPD promoter set forth in SEQ ID NO:1. Alternatively, the increase or decrease in transcriptional regulatory activity can include about a 0.5 fold, 1 fold, 2 fold, 4 fold, 8 fold, 16 fold, or 32 overall increase or decrease in transcription when compared to the transcriptional regulatory activity of a native HPPD promoter or the native soy HPPD promoter set forth in SEQ ID NO:1.

Various alterations can be made in the HPPD promoters disclosed herein. In some embodiments, the HPPD promoters or active variants and fragments thereof have been altered such that the transcriptional regulatory activity is decreased when compared to the wild type HPPD promoter. In such embodiments, the HPPD promoter can comprise a deletion of at least one of the TATA motif polynucleotide segments in the HPPD promoter, including a deletion of the TATA1 motif (SEQ ID NO: 44), the TATA2 motif (SEQ ID NO: 45), the TATA3 motif (SEQ ID NO: 46), the TATA4 motif (SEQ ID NO: 47), and/or the TATA5 motif (SEQ ID NO: 48). See, also FIG. 1 and FIG. 3. Non-limiting examples of such active variants and fragments of an HPPD promoter are set forth in SEQ ID NO: 2, 3, 4, 11, 20, and 76.

Alternatively, an HPPD promoter or an active variant or fragment thereof can comprise at least one nucleic acid mutation of at least one TATA motif, including, for example, at least one mutation in the TATA1 motif, at least one mutation in the TATA2 motif, and/or at least one mutation in the TATA3 motif, or any combination thereof. As used herein, nucleic acid mutations encompass base additions, base deletions and base substitutions. In some embodiments an alteration of an HPPD promoter encompasses at least one or at least two alterations of at least one, at least two or at least three TATA motifs. In some embodiments, alteration of an HPPD promoter comprises both a deletion of at least one TATA motif and an alteration of at least one TATA motif. See, also FIG. 1 and Table 3. Non-limiting examples of such active variants and fragments of an HPPD promoter are set forth in SEQ ID NO: 5, 6, 7, 8, 9, 10, 12, 13, 14, 15, 16, 17, 18, 19, 74, or 75. It is further recognized that active variants and fragments of the HPPD promoter may contain a deletion of any one or more TATA motif in combination with at least one or more alterations in the remaining TATA motifs.

In specific embodiments, active fragments of the HPPD promoter as set forth in SEQ ID NO:1 are provided. Such fragments can include various 5' deletions of SEQ ID NO: 1 including but not limited to polynucleotides comprising nucleotides 100-2166 of SEQ ID NO: 1; 200-2166 of SEQ ID NO: 1; 300-2166 of SEQ ID NO: 1; 400-2166 of SEQ ID NO: 1; 500-2166 of SEQ ID NO: 1; 600-2166 of SEQ ID NO: 1; 700-2166 of SEQ ID NO: 1; 800-2166 of SEQ ID NO: 1; 900-2166 of SEQ ID NO: 1; 1000-2166 of SEQ ID NO: 1; 1200-2166 of SEQ ID NO: 1; 1400-2166 of SEQ ID NO: 1; 1600-2166 of SEQ ID NO: 1; 1800-2166 of SEQ ID NO: 1; or 2000-2166 of SEQ ID NO: 1, wherein the various fragments continue to have transcriptional regulatory activity. Further provided are active variants of the 5' deletions of SEQ ID NO:1. Such active variants can comprise at least 80%, 85%, 90%, 91%, 92%, 93%, 94%, 95%, 96%, 97%, 98%, 99% or more sequence identity to any one of the promoters comprising SEQ ID NO: 1 or polynucleotides comprising nucleotides 100-2166 of SEQ ID NO: 1; 200-2166 of SEQ ID NO: 1; 300-2166 of SEQ ID NO: 1; 400-2166 of SEQ ID NO: 1; 500-2166 of SEQ ID NO: 1; 600-2166 of SEQ ID NO: 1; 700-2166 of SEQ ID NO: 1; 800-2166 of SEQ ID NO: 1; 900-2166 of SEQ ID NO: 1; 1000-2166 of SEQ ID NO: 1; 1200-2166 of SEQ ID NO: 1; 1400-2166 of SEQ ID NO: 1; 1600-2166 of SEQ ID NO: 1; 1800-2166 of SEQ ID NO: 1; or 2000-2166 of SEQ ID NO: 1.

In specific embodiments, active fragments of the HPPD promoter as set forth in SEQ ID NO:1 are provided. Such fragments can include various 3' deletions of SEQ ID NO: 1 including but not limited to polynucleotides comprising nucleotides 1-2066 of SEQ ID NO: 1; 1-1966 of SEQ ID NO: 1; 1-1866 of SEQ ID NO: 1; 1-1766 of SEQ ID NO: 1; 1-1666 of SEQ ID NO: 1; 1-1566 of SEQ ID NO: 1; 1-1466 of SEQ ID NO: 1; 1-1366 of SEQ ID NO: 1; 1-1266 of SEQ ID NO: 1; 1-1166 of SEQ ID NO: 1; 1-966 of SEQ ID NO: 1; 1-766 of SEQ ID NO: 1; 1-566 of SEQ ID NO: 1; 1-366 of SEQ ID NO: 1; or 1-166 of SEQ ID NO: 1, wherein the various fragments continue to have regulatory activity. Further provided are active variants of the 3' deletions of SEQ ID NO:1. Such active variants can comprise at least 80%, 85%, 90%, 91%, 92%, 93%, 94%, 95%, 96%, 97%, 98%, 99% or more sequence identity to any one of the promoters comprising SEQ ID NO: 1 or polynucleotides comprising nucleotides 1-2066 of SEQ ID NO: 1; 1-1966 of SEQ ID NO: 1; 1-1866 of SEQ ID NO: 1; 1-1766 of SEQ ID NO: 1; 1-1666 of SEQ ID NO: 1; 1-1566 of SEQ ID NO: 1; 1-1466 of SEQ ID NO: 1; 1-1366 of SEQ ID NO: 1; 1-1266 of SEQ ID NO: 1; 1-1166 of SEQ ID NO: 1; 1-966 of SEQ ID NO: 1; 1-766 of SEQ ID NO: 1; 1-566 of SEQ ID NO: 1; 1-366 of SEQ ID NO: 1; or 1-166 of SEQ ID NO: 1.

Nucleic acid molecules that are fragments of a HPPD promoter comprise at least about 4, 6, 8, 10, 12, 16, 25, 50, 75, 100, 150, 200, 250, 300, 350, 400, 450, 500, 550, 600, 650, 700 or 800 consecutive nucleotides of SEQ ID NO:1 or up to the total number of nucleotides present in a full-length HPPD promoter sequence disclosed herein (i.e. 2166 polynucleotides of SEQ ID NO:1). In certain embodiments, fragments of a HPPD promoter comprise at least 6-8 polynucleotides of SEQ ID NO: 1, or of any length long enough to comprise transcriptional or regulatory features.

A structural gene or coding sequence is a DNA sequence that is transcribed into messenger RNA (mRNA) which is then translated into a sequence of amino acids characteristic of a specific polypeptide.

B. Chimeric Promoters

Further provided are chimeric promoter constructs or chimeric promoters which employ regulatory regions of the HPPD promoter operably linked to a core promoter region. As used herein a "chimeric promoter construct" refers to a first polynucleotide comprising a regulatory region operably linked to a second polynucleotide comprising a heterologous core promoter. Depending on the regulatory region of the HPPD promoter and the core promoter region employed in a given chimeric promoter, one can influence the transcriptional regulatory activity of the chimeric promoter and thus provide means to refine the manner in which a polynucleotide of interest is expressed (i.e. influence the temporal expression, tissue-specific expression or level of expression). In non-limiting embodiments, any one of the polynucleotides set forth in any one of SEQ ID NO: 23, 24, 25, 26, 27, 28, 29, 30, 31, 32, 33, 34, 35, 36, 37, 38, 39, 40, or 77, or active variants or fragments thereof, can comprise a chimeric promoter.

Various structures within eukaryotic promoters are known. See, for example, Kochetov, *Mol. Biol.,* 2002, 36:510-516; Priest, *Curr. Opin. in Plant Biol.,* 2009, 12:643-649; Fuda, *Nature,* 2009, 461: 186-192, and Saul, *The Plant Journal,* 2009, 60:1031-1042.

i. Regulatory Region of an HPPD Promoter

The chimeric promoters disclosed herein comprise a "regulatory region of an HPPD promoter" operably linked to a core promoter. As used herein, a "regulatory region of an HPPD promoter" comprises a fragment or variant of an HPPD promoter. Non-limiting examples of regulatory regions of the HPPD promoter can comprise the polynucleotide set forth in SEQ ID NO: 2, 3, 4, 5, 6, 7, 8, 9, 10, 11, 12, 13, 14, 15, 16, 17, 18, 19, 20, 74, 75, and 76 or active fragments and variants thereof.

In some embodiments, the regulatory region of the HPPD promoter or an active variant or fragment thereof has been modified to no longer retain regulatory activity in the absence of a core promoter. Such regulatory regions of the HPPD promoter when operably linked to a polynucleotide sequence of interest in the absence of a core promoter, reduce the expression of the polynucleotide sequence of interest to that of background levels. The regulatory activity of these regulatory regions of the HPPD promoter is increased when the regulatory region of the HPPD promoter is operably linked to a core promoter. It is further recognized that the modulation of the regulatory activity need not be an overall increase or decrease in activity but also includes a change in tissue distribution of the regulatory activity or an alteration in response to specific inducing factors. Thus, inactive fragments of the regulatory regions described herein can be made active by combination with a core promoter sequence or synthetic element, wherein the active regulatory region maintains the tissue or temporal specificity of the native HPPD promoter. Non-limiting examples of such regulatory regions of the HPPD promoter are set forth in SEQ ID NO: 2, 3, 4, 5, 6, 7, 8, 9, 10, 11, 12, 13, 14, 15, 16, 17, 18, 19, 20, 74, 75, and 76.

In other embodiments, the regulatory region of an HPPD promoter or an active variant or fragment thereof has regulatory activity equal to or less than 95%, 90%, 80%, 70%, 60%, 50%, 40%, 35%, 30%, 25%, 20%, 15%, 14%, 13%, 10%, 9%, 8%, 7%, 6%, 5%, 4%, 3%, 2% or 1% of the wild type HPPD promoter (such as that set forth in SEQ ID NO:1) in the absence of the core promoter. In some embodiments, the regulatory region of an HPPD promoter has regulatory activity between 10% and 20%, 20% and 30%, 23% and 36%, 30% and 40%, 40% and 50%, 50% and 60%, 60% and 70%, 70% and 80%, and 80% and 90% of the wild-type HPPD promoter (such as that set forth in SEQ ID NO:1) in the absence of the operably linked core promoter. Non-limiting examples of such regulatory regions of the HPPD promoter are set forth in SEQ ID NO: 2, 3, 4, 5, 6, 7, 8, 9, 10, 11, 12, 13, 14, 15, 16, 17, 18, 19, 20, 74, 75, and 76.

In specific embodiments, active fragments of the regulatory region of an HPPD promoter as set forth in SEQ ID NO:1 are provided. Such fragments can include various 5' deletions of SEQ ID NO: 1 including but not limited to polynucleotides comprising nucleotides 100-2166 of SEQ ID NO: 1; 200-2166 of SEQ ID NO: 1; 300-2166 of SEQ ID NO: 1; 400-2166 of SEQ ID NO: 1; 500-2166 of SEQ ID NO: 1; 600-2166 of SEQ ID NO: 1; 700-2166 of SEQ ID NO: 1; 800-2166 of SEQ ID NO: 1; 900-2166 of SEQ ID NO: 1; 1000-2166 of SEQ ID NO: 1; 1200-2166 of SEQ ID NO: 1; 1400-2166 of SEQ ID NO: 1; 1600-2166 of SEQ ID NO: 1; 1800-2166 of SEQ ID NO: 1; or 2000-2166 of SEQ ID NO: 1, wherein the various fragments continue to act as regulatory regions of HPPD promoters as described above.

Further provided are regulatory regions of an HPPD promoter which are active variants of the 5' deletions of SEQ ID NO: 1. Such active variants can comprise at least 80%, 85%, 90%, 91%, 92%, 93%, 94%, 95%, 96%, 97%, 98%, 99% or more sequence identity to any one of the polynucleotides comprising SEQ ID NO: 1 or comprising nucleotides 100-2166 of SEQ ID NO: 1; 200-2166 of SEQ ID NO: 1; 300-2166 of SEQ ID NO: 1; 400-2166 of SEQ ID NO: 1; 500-2166 of SEQ ID NO: 1; 600-2166 of SEQ ID NO: 1; 700-2166 of SEQ ID NO: 1; 800-2166 of SEQ ID NO: 1; 900-2166 of SEQ ID NO: 1; 1000-2166 of SEQ ID NO: 1; 1200-2166 of SEQ ID NO: 1; 1400-2166 of SEQ ID NO: 1; 1600-2166 of SEQ ID NO: 1; 1800-2166 of SEQ ID NO: 1; or 2000-2166 of SEQ ID NO: 1, wherein the various variants continue to act as regulatory regions of HPPD promoters as described above.

In specific embodiments, active fragments of the regulatory region of an HPPD promoter as set forth in SEQ ID NO:1 are provided. Such fragments can include various 3' deletions of SEQ ID NO: 1 including but not limited to polynucleotides comprising nucleotides 1-2066 of SEQ ID NO: 1; 1-1966 of SEQ ID NO: 1; 1-1866 of SEQ ID NO: 1; 1-1766 of SEQ ID NO: 1; 1-1666 of SEQ ID NO: 1; 1-1566 of SEQ ID NO: 1; 1-1466 of SEQ ID NO: 1; 1-1366 of SEQ ID NO: 1; 1-1266 of SEQ ID NO: 1; 1-1166 of SEQ ID NO: 1; 1-966 of SEQ ID NO: 1; 1-766 of SEQ ID NO: 1; 1-566 of SEQ ID NO: 1; 1-366 of SEQ ID NO: 1; or 1-166 of SEQ ID NO: 1, wherein the various fragments continue to act as regulatory regions of HPPD promoters as described above. Further provided are active variants of the 3' deletions of SEQ ID NO:1. Such active variants can comprise at least 80%, 85%, 90%, 91%, 92%, 93%, 94%, 95%, 96%, 97%, 98%, 99% or more sequence identity to any one of the promoters comprising SEQ ID NO: 1 or polynucleotides comprising nucleotides 1-2066 of SEQ ID NO: 1; 1-1966 of SEQ ID NO: 1; 1-1866 of SEQ ID NO: 1; 1-1766 of SEQ ID NO: 1; 1-1666 of SEQ ID NO: 1; 1-1566 of SEQ ID NO: 1; 1-1466 of SEQ ID NO: 1; 1-1366 of SEQ ID NO: 1; 1-1266 of SEQ ID NO: 1; 1-1166 of SEQ ID NO: 1; 1-966 of SEQ ID NO: 1; 1-766 of SEQ ID NO: 1; 1-566 of SEQ ID NO: 1; 1-366 of SEQ ID NO: 1; or 1-166 of SEQ ID NO: 1, wherein wherein the various fragments continue to act as regulatory regions of HPPD promoters as described above.

Additional non-limiting examples of active variants and fragments of a regulatory region of the HPPD promoter can include a deletion of a at least one of the TATA motif polynucleotide segments in the HPPD promoter, including a deletion of the TATA1 motif (SEQ ID NO: 44), the TATA2 motif (SEQ ID NO: 45), the TATA3 motif (SEQ ID NO: 46), the TATA4 motif (SEQ ID NO: 47), and/or the TATA5 motif (SEQ ID NO: 48). Alternatively, variants and fragments of a regulatory region of an HPPD promoter can comprise at least one nucleic acid mutation of at least one TATA motif, including, for example, at least one mutation in the TATA 1 motif, at least one mutation in the TATA2 motif, at least one mutation in the TATA3 motif, at least one mutation in the TATA4 motif, and/or at least one mutation in the TATA5 motif, or any combination thereof. As used herein, nucleic acid mutations encompass base additions, base deletions and base substitutions. In some embodiments an alteration of the regulatory region of an HPPD promoter encompasses at least one or at least two alterations of at least one, at least two or at least three TATA motifs. In some embodiments, alteration of the regulatory region comprises both a deletion of at least one TATA motif and an alteration of at least one TATA motif. See, for example, Table 3.

ii. Core Promoters

The chimeric promoter disclosed herein comprises a regulatory region of an HPPD promoter operably linked to a heterologous core promoter. As used herein, a "core promoter" refers to a polynucleotide comprising the essential nucleotide sequences for expression of an operably linked coding sequence, including, but not limited to, a TATA box and transcription start site. By this definition, a core promoter may or may not have detectable activity in the absence of specific sequences that may enhance the activity or confer tissue specific activity, such as the regulatory regions of the HPPD promoter. Such core promoter sequences are known. See for example, U.S. Pat. No. 6,072,050, U.S. Pat. No. 6,555,673, Vedel, *Plant Science,* 2011, 180:182-189, herein incorporated by reference in their entirety.

The core promoters described herein may also comprise heterologous or synthetic elements having core promoter activity. For example, core promoters may comprise the SynII core (SEQ ID NO: 70; U.S. Pat. No. 6,072,050, SEQ ID NO: 1), a 5' UTR, an enzyme recognition site, or other regions such as Rsyn7, or any combination thereof. Other elements that could be found in core promoters are identified in Smale, *Annu. Rev. Biochem.,* 2003, 72:449-79, herein incorporated by reference in its entirety In specific embodiments, the core promoter can comprise synthetic elements as set forth in SEQ ID NO: 21 or 22 or active fragments or variants thereof. Synthetic element I (SEQ ID NO: 21) was derived from SynII core (U.S. Pat. No. 6,072,050 SEQ ID NO: 1) sequences followed by the 45 bp putative 5' UTR sequence (SEQ ID NO: 56) including the predicted transcription start site from the soybean native HPPD gene.

In other embodiments, the core promoter comprises synthetic element II (SEQ ID NO: 22) or active fragments or variants thereof. Synthetic element II contains the Rsyn7 region derived from U.S. Pat. No. 6,072,050 SEQ ID NO: 2 immediately upstream of synthetic element I (SEQ ID NO: 22). SEQ ID NO: 21 and 22 were derived from SEQ ID NO: 1 and 2 of U.S. Pat. No. 6,072,050 which is herein incorporated by reference in its entirety. In particular embodiments, the core promoter comprises synthetic element III (SEQ ID NO: 83) or active fragments or variants thereof. Synthetic element III contains the Rsyn7 and SynII core.

Fragments and variants of the core promoter maintain core promoter activity. As used herein, by "core promoter activity" is intended the ability of the core promoter to modulate the regulatory activity of an operably linked regulatory region of an HPPD promoter when compared to the regulatory activity of the regulatory region of the HPPD promoter in the absence of the core promoter. Alternatively, "core promoter activity" can refer to the ability of a core promoter to direct transcription of a polynucleotide of interest in the absence of a regulatory region of an HPPD promoter. For example, a core promoter when operably linked to a regulatory region of an HPPD promoter can either decrease or increase the transcriptional regulatory activity of the regulatory region of the HPPD promoter when compared to the transcriptional regulatory activity of the regulatory region of an HPPD promoter in the absence of the core promoter. Such an increase or decrease in transcriptional regulatory activity can include about a 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, or greater increase or decrease in transcriptional regulatory activity when compared to the regulatory region of the HPPD promoter in the absence of the core promoter. Alternatively, the modulated activity of the regulatory region can include about a 0.5 fold, 1 fold, 2 fold, 4 fold, 8 fold, 16 fold, or 32 fold overall increase or decrease in transcriptional regulatory activity of the regulatory region of the HPPD promoter in the absence of the core promoter.

It is further recognized that the modulation of the transcriptional regulatory activity by the core promoter need not be an overall increase or decrease in activity, but also includes a change in tissue distribution of the regulatory activity.

In some embodiments, a core promoter is operably linked to a regulatory region of an HPPD promoter thereby modulating the transcriptional regulatory activity of the regulatory region. Any one of the polynucleotides set forth in any one of SEQ ID NO: 23, 24, 25, 26, 27, 28, 29, 30, 31, 32, 33, 34, 35, 36, 37, 38, 39, 40, 41, 77, or 78 or active variants or fragments thereof, can comprise a chimeric promoter.

C. Fragments and Variants

Fragments and variants of the disclosed HPPD promoters, chimeric promoters, core promoters and/or regulatory regions of an HPPD promoter are also encompassed herein. By "fragment" is intended a portion of an HPPD promoter, chimeric promoter, core promoter and/or regulatory region of an HPPD promoter. A fragment of a HPPD promoter, chimeric promoter, core promoter and/or regulatory region of an HPPD promoter may encode a biologically active portion of a HPPD promoter, chimeric promoter, core promoter and/or regulatory region of an HPPD promoter, or it may be a fragment that can be used as a hybridization probe, a PCR primer using methods disclosed below, or may be combined with another DNA fragment to create a new promoter. A biologically active portion of a HPPD promoter, chimeric promoter, core promoter and/or regulatory region of an HPPD promoter can be prepared by isolating a polynucleotide segment of an HPPD promoter, chimeric promoter, core promoter and/or regulatory region of an HPPD promoter disclosed herein, and assessing the activity of the portion of the promoter polynucleotide. Polynucleotides that are fragments of an HPPD promoter, chimeric promoter, core promoter and/or regulatory region of an HPPD promoter comprise at least 16, 20, 50, 75, 100, 150, 200, 250, 300, 350, 400, 450, 500, 550, 600, 650, 700, 800, 900, 1,000, 1,100, 1,200, 1,300, or 1,450 contiguous nucleotides, or up to the number of nucleotides present in a full-length HPPD promoter, chimeric promoter, core promoter and/or regulatory region of an HPPD promoter disclosed herein. In some embodiments, a fragment comprises an HPPD promoter, chimeric promoter, core promoter and/or regulatory region of an HPPD promoter where 1-500, 500-1000, 1000-1500 or 1500-2000 nucleotides have been deleted from the 5' end of the promoter polynucleotide.

A fragment of an HPPD promoter, chimeric promoter, core promoter and/or regulatory region of an HPPD promoter can be a fragment of a variant of an HPPD promoter, chimeric promoter, core promoter and/or regulatory region of an HPPD promoter. For example, a fragment of an HPPD promoter, chimeric promoter, core promoter and/or regulatory region of an HPPD promoter encompasses fragments of polynucleotides having 40%, 45%, 50%, 55%, 60%, 65%, 70%, 75%, 80%, 85%, 90%, 91%, 92%, 93%, 94%, 95%, 96%, 97%, 98%, 99% or more sequence identity to the promoter polynucleotides of the invention.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide comprises a naturally occurring nucleotide sequence. Variants of the HPPD promoters, chimeric promoters, core promoters and/or regulatory regions of an HPPD promoter disclosed herein may retain activity of the HPPD promoter, chimeric promoter, core promoter and/or regulatory region of an HPPD promoter as described in detail elsewhere herein. Naturally occurring variant polynucleotides can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis. Generally, variants of a HPPD promoter, chimeric promoter, core promoter and/or regulatory region of an HPPD promoter disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein. Variant polynucleotides disclosed herein can also have 40%, 45%, 50%, 55%, 60%, 65%, 70%, 75%, 80%, 85%, 90%, 91%, 92%, 93%, 94%, 95%, 96%, 97%, 98%, 99% or more sequence identity to fragments of the HPPD promoter, chimeric promoter, core promoter and/or regulatory region of an HPPD promoter disclosed herein, including fragments where 1-500, 500-1000, 1000-1500 or 1500-2000 nucleotides of the 5' end of the HPPD promoter, chimeric promoter, core promoter and/or regulatory region of an HPPD promoter have been deleted, or where 1-500, 500-1000, 1000-1500 or 1500-2000 nucleotides of the 3' end of the HPPD promoter, chimeric promoter, core promoter and/or regulatory region of an HPPD promoter have been deleted.

Variant polynucleotides also encompass sequences derived from a mutagenic and recombinogenic procedure such as DNA shuffling. With such a procedure, one or more different HPPD promoters, chimeric promoters, core promoters and/or regulatory regions of an HPPD promoter can be manipulated to create a new HPPD promoter, chimeric promoter, core promoter and/or regulatory region of an HPPD promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

D. Sequence Comparison

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or promoter sequence, or the complete cDNA or promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FAST A, and TF ASTA in the GCG Wisconsin Genetics Software Package, Version 10 (available from Accelrys Inc., 9685 Scranton Road, San Diego, Calif., USA). Alignments using these programs can be performed using the default parameters. The CLUST AL program is well described by Higgins et al. (1988) *Gene* 73:237-244 (1988); Higgins et al. (1989) *CABIOS* 5: 151-153; Corpet et al. (1988) *Nucleic Acids Res.* 16:1 0881-90; Huang et al. (1992) *CABIOS* 8: 155-65; and Pearson et al. (1994) *Meth. Mol. Biol.* 24:307-331. The BLAST programs of Altschul et al (1990) *J. Mol. Biol.* 215: 403 are based on the algorithm of Karlin and Altschul (1990) supra.BLAST nucleotide searches can be performed with the BLASTN program, score=100, word length=12, to obtain nucleotide sequences homologous to a nucleotide sequence of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotide sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

E. DNA Constructs

The various HPPD promoters, chimeric promoters, core promoters and/or regulatory regions of an HPPD promoter of the invention can be provided in DNA constructs or expression cassettes for expression in plants of interest. The cassette will include the HPPD promoter, chimeric promoter, core promoter and/or regulatory region of an HPPD promoter disclosed herein operably linked to a polynucleotide of interest. "Operably linked" is intended to mean a functional linkage between two or more elements. For example, an operable linkage between a polynucleotide of interest and an HPPD promoter, chimeric promoter, core promoter and/or regulatory region of an HPPD promoter is a functional link that allows for expression of the polynucleotide of interest. An operable linkage between a regulatory region of an HPPD promoter and a core promoter is a linkage that allows the core promoter to modulate the transcriptional regulatory activity of the regulatory region of the HPPD promoter. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide of interest to be under the transcriptional regulation of an HPPD promoter, chimeric promoter, core promoter and/or regulatory region of an HPPD promoter of the invention. The expression cassette may additionally contain selectable marker genes.

The expression cassette can include in the 5'-3' direction of transcription, an HPPD promoter, chimeric promoter, core promoter and/or regulatory region of an HPPD promoter, a polynucleotide of interest, and a transcriptional and translational termination region (i.e., termination region) functional in plants. The regulatory regions (i.e., promoters, core promoters, and regulatory regions) of the invention and/or the polynucleotide of interest may be native/analogous to the host cell or to each other. Alternatively, the regulatory regions of the invention and/or the HPPD polynucleotide may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, an HPPD promoter and/or chimeric promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

It is recognized that expression cassettes comprising the various HPPD promoters and chimeric HPPD promoters disclosed herein can be generated in vivo. For example, the native HPPD gene can be modified in vivo such that the structure of the native HPPD promoter is altered to reflect one of the HPPD promoters disclosed herein. Methods for targeted mutagenesis in vivo are known. For example, a DNA sequence having the desired sequence alteration can be flanked by sequences homologous to the genomic target. One can then select or screen for a successful homologous recombination event. See, U.S. Pat. No. 5,527,695. Generally, such a vector construct is designed having two regions of homology to the genomic target which flank a polynucleotide having the desired sequence. Introduction of the vector into a plant cell will allow homologous recombination to occur and to produce an exchange of sequences between the homologous regions at the target site.

Such methods of homologous recombination can further be combined with agents that induce site-specific genomic double-stranded breaks in plant cells. Such double strand break agents can be engineered to produce the break at a targeted site and thereby enhance the homologous recombination events. See, for example, Puchta, et al., (1996) *Proc Natl Acad Sci USA* 93:5055-5060; US Patent Application Publication Number 2005/0172365A1; US Patent Application Publication Number 2006/0282914, WO 2005/028942; WO 2004/067736 published Aug. 12, 2004; U.S. Pat. No. 5,792,632; U.S. Pat. No. 6,610,545; Chevalier et al., (2002) *Mol Cell* 10:895-905; Chevalier et al., (2001) *Nucleic Acids Res* 29:3757-3774; Seligman et al., (2002) *Nucleic Acids Res* 30:3870-3879; US Application publication 2009-0133152; and, WO 2005/049842, each of which is herein incorporated by reference in their entirety.

The HPPD promoter or chimeric promoter used to express a polynucleotide of interest can be selected based on the desired outcome. For example, the selection of the HPPD promoter or chimeric promoter used in the expression cassettes described herein can determine the level of expression along with the spatial expression and/or temporal expression pattern of an operably linked polynucleotide of interest in plants, plant cells or plant explants. HPPD promoters and/or chimeric promoters disclosed herein can be selected to express polynucleotides of interest in specific cell types (such as leaf epidermal cells, mesophyll cells, root cortex cells) or in specific tissues or organs (roots, leaves, seeds, or flowers, for example) and the selection reflects the desired location of accumulation of the gene product. Alternatively, the HPPD promoters and/or chimeric promoters disclosed herein can be selected to drive expression of the HPPD polynucleotide under various inducing conditions. The HPPD promoters and/or chimeric promoters also vary in their strength, i.e., ability to promote transcription. In one embodiment, the HPPD promoter and/or chimeric promoter described herein is selected to express an HPPD polypeptide, having insensitivity to an HPPD inhibitor, in sufficient levels in a plant to impart tolerance of the plant to the HPPD inhibitor.

The termination region may be native with the transcriptional initiation region of interest, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

The HPPD promoter and/or chimeric promoter described herein can further be operably linked to additional regulatory elements that influence transcription, including, but not limited to, introns, 5' untranslated regions and enhancer elements. As used herein, an "enhancer sequence," "enhancer domain," "enhancer element," or "enhancer," when operably linked to an appropriate promoter, will modulate the level of transcription of an operably linked polynucleotide of interest. For example, the HPPD promoter and/or chimeric promoter described herein could be operably linked to the 35S enhancer as described in US 2007-0061917, herein incorporated by reference in its entirety. In specific embodiments, the enhancer of the invention can alter normal promoter expression patterns. Thus, the HPPD promoter and/or chimeric promoter described herein can further comprise at least one, two, three, four or more copies of an enhancer domain or an active variant or fragment of the domain.

The HPPD promoters and/or chimeric promoters described herein can further comprise additional portions of other regulatory regions. Thus, the HPPD promoters and/or chimeric promoters described herein can comprise upstream regulatory elements such as those responsible for tissue and temporal expression of the coding polynucleotide of interest. In the context of this disclosure, the term "regulatory element" also refers to a sequence of DNA, usually, but not always, upstream (5') to the coding sequence of a structural gene or polynucleotide of interest, which includes sequences which modulate the expression of the polynucleotide of interest. It is to be understood that nucleotide sequences, located within introns, or 3' of the polynucleotide of interest may also contribute to the regulation of expression of a polynucleotide of interest. Examples of suitable introns include, but are not limited to, the maize IVS6 intron, the maize actin intron, or maize adh1. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In some embodiments, the expression cassettes disclosed herein contain a polynucleotide in which the 5' untranslated region (UTR) of the promoter polynucleotide has been partially or completely deleted. As used herein, the 5' UTR, or leader sequence, refers to a particular section of mRNA and the encoding DNA, beginning at the transcription start site and ending one nucleotide before the first nucleotide of the start codon. The 5' UTR can also refer to the region of a promoter polynucleotide of the invention downstream of the transcriptional start site. The 5' UTR of the promoter polynucleotides of the invention can comprise at least 10, 15, 20, 25, 30, 35, 40, 45, 50, 60, 70, 80, 90, 100, 250 or 500 consecutive nucleotides.

In some embodiments, the expression cassettes disclosed herein include cis-elements, for example the transcription factor sequences such as found in Rsyn7, to alter the pattern or strength of the transcriptional regulatory activity of the promoter (see Priest et al. (2009) Curr. Opin. Plant Bio. 12:643-649 and references described elsewhere herein all of which are hereby incorporated by reference).

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, substitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention, including for example, DsRed as described in Examples 3 and 4 and Table 2.

F. Polynucleotides of Interest

Any polynucleotide of interest may be operably linked to the HPPD promoters and/or chimeric promoters disclosed herein. Such polynucleotides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest for the present invention include, but are not limited to, genes that improve crop yield, polypeptides that improve desirability of crops, genes encoding proteins conferring resistance to abiotic stress, such as drought, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. It is recognized that any polynucleotides of interest can be operably linked to the HPPD promoters and/or chimeric promoters of the invention and expressed in a plant. The expression level of the polynucleotide or polypeptide of interest may be measured directly, for example, by assaying for the level of the polypeptide or polynucleotide in the organism, or indirectly, for example, by measuring the activity of the polypeptide or polypeptide in the organism. These nucleotide sequences of interest may encode proteins involved in providing disease or pest resistance. By “disease resistance” or “pest resistance” is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products.

As used herein, the term “pest” includes, but is not limited to, insects, fungi, bacteria, viruses, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

An “herbicide resistance protein” or a protein resulting from expression of an “herbicide resistance-encoding nucleic acid molecule” includes proteins that confer upon a cell the ability to tolerate a higher concentration of an herbicide than cells that do not express the protein, or to tolerate a certain concentration of an herbicide for a longer period of time than cells that do not express the protein. In one embodiment, the polynucleotide that confers tolerance to herbicide of interest comprises an ALS inhibitor tolerant polypeptide which confers tolerance of a dose of sulfonylurea, imidazolinone, triazolopyrimidines, pyrimidinyoxy(thio)benzoates, and/or sulfonylamino-carbonyl-triazonline herbicide. Sulfonylurea and imidazolinone herbicides inhibit growth of higher plants by blocking acetolactate synthase (ALS), also known as, acetohydroxy acid synthase (AHAS). For example, plants containing particular mutations in ALS (e.g., the S4 and/or HRA mutations) are tolerant to sulfonylurea herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor tolerant polypeptide comprises a sulfonamide-tolerant acetolactate synthase, a sulfonamide-tolerant acetohydroxy acid synthase, an imidazolinone-tolerant acetolactate synthase, or an imidazolinone-tolerant acetohydroxy acid synthase.

Polynucleotides coding for resistance to herbicides that act to inhibit action of glutamine synthase, such as phosphinothricin or basta (e.g., the bar gene), glyphosate (e.g., the EPSPS gene and the gat gene; see, for example, U.S. Publication No. 20040082770 and WO 03/092360) or other such genes known in the art can also be used. The bar gene encodes resistance to the herbicide basta, the nptII gene encodes resistance to the antibiotics kanamycin and geneticin, and the ALS gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481, 7,405,074, and 7,803,992 each of which are herein incorporated by reference.

Polypeptides conferring tolerance to herbicides which inhibit the enzyme glutamine synthase, such as phosphinothricin or glufosinate (e.g., the bar gene) can also be used. Glutamine synthetase (GS) appears to be an essential enzyme necessary for the development and life of most plant cells, and inhibitors of GS are toxic to plant cells. Glufosinate herbicides have been developed based on the toxic effect due to the inhibition of GS in plants. These herbicides are non-selective; that is, they inhibit growth of all the different species of plants present. The development of plants containing an exogenous phosphinothricin acetyltransferase is described in U.S. Pat. Nos. 5,969,213; 5,489,520; 5,550,318; 5,874,265; 5,919,675; 5,561,236; 5,648,477; 5,646,024; 6,177,616; and 5,879,903, which are incorporated herein by reference in their entireties for all purposes. Mutated phosphinothricin acetyltransferase having this activity are also disclosed.

In still other embodiments, polypeptides conferring tolerance to herbicides which inhibit protox (protoporphyrinogen oxidase) can be used. Protox is necessary for the production of chlorophyll, which is necessary for all plant survival. The protox enzyme serves as the target for a variety of herbicidal compounds. These herbicides also inhibit growth of all the different species of plants present. The development of plants containing altered protox activity which are resistant to these herbicides are described in U.S. Pat. Nos. 6,288,306; 6,282,837; and 5,767,373; and international publication WO 01/12825, which are incorporated herein by reference in their entireties for all purposes.

In still other embodiments, polypeptides involving other modes of herbicide resistance are employed. For example, hydroxyphenylpyruvatedioxygenases are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Plants more resistant to certain herbicides are described in U.S. Pat. Nos. 6,245,968; 6,268,549; and 6,069,115; and international publication WO 99/23886, which are incorporated herein by reference in their entireties for all purposes. Mutated hydroxyphenylpyruvatedioxygenase insensitive to HPPD inhibitors are also disclosed. For example, those polynucleotides disclosed in U.S. Utility application Ser. No. 13/208,966, entitled "Compositions and Methods Comprising Sequences Having Hydroxyphenylpyruvate Dioxygenase (HPPD) Activity" filed concurrently herewith and herein incorporated by reference may be operably linked to the HPPD promoters and/or chimeric promoters disclosed herein. Polynucleotides such as aad1, aad12, and dmo can be employed for their herbicide resistance properties. See for example, U.S. Pat. Nos. 7,838,733 and 7,884,262.

Additional herbicides, include but are not limited to, an acetyl Co-A carboxylase inhibitor such as quizalofop-P-ethyl, a synthetic auxin such as quinclorac, a protoporphyrinogen oxidase (PPO) inhibitor herbicide (such as sulfentrazone), a pigment synthesis inhibitor herbicide such as a hydroxyphenylpyruvate dioxygenase inhibitor (e.g., mesotrione or sulcotrione), a phosphinothricin acetyltransferase or a phytoene desaturase inhibitor like diflufenican, pigment synthesis inhibitor, auxin herbicides such as 2,4-D and dicamba, see for example U.S. Pat. Nos. 5,877,115 and 5,175,353.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase. Polynucleotides that improve desirability of crops include, for example, those that allow plants to have a reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

As noted, the polynucleotide of interest operably linked to an HPPD promoter and/or a chimeric promoter as described herein may encode a suppression element, such as an RNAi element. "RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced.

i. HPPD Polynucleotides of Interest

The HPPD polypeptide converts hydroxyphenylpyruvate, derived from the aromatic amino acid biosynthesis pathway, to homogentisate. Homogentisate is a precursor of tocopherols and plastoquinones, an electron carrier essential in the biosynthesis of carotenoids. Consequently, when HPPD is inhibited by herbicide inhibitors, the plant can not protect itself from the radicals generated by light activation of chlorophyll. More specifically, inhibition of HPPD polypeptide leads to the depletion of protective pigments in the plant tissue resulting in bleaching of tissues which leaves the plants vulnerable to damage by light. HPPD inhibitors are an important class of herbicides and transgenes that confer crop tolerance to HPPD inhibitors are of significant value, especially for managing weed resistance to glyphosate.

As used herein, "Hydroxyphenylpyruvate dioxygenase" and "HPPD" "4-hydroxy phenyl pyruvate (or pyruvic acid) dioxygenase (4-HPPD)" and "p-hydroxy phenyl pyruvate (or pyruvic acid) dioxygenase (p-OHPP)" are synonymous and refer to a non-heme iron-dependent oxygenase that catalyzes the conversion of 4-hydroxyphenylpyruvate to homogentisate. In organisms that degrade tyrosine, the reaction catalyzed by HPPD is the second step in the tyrosine degradation pathway. In plants, formation of homogentisate is necessary for the synthesis of plastoquinone, an essential redox cofactor, and tocopherol.

Various variants of HPPD sequences are also known. See, for example, U.S. Provisional Application 61/401,456, filed Aug. 13, 2010, Compositions and Methods Comprising Sequences having Hydroxyphenylpyruvate Dioxygenase (HPPD) Activity, herein incorporated by reference in it entirety. See, also, US 2003/0066102, WO97/49816, US 2010/0197503, U.S. Pat. No. 7,312,379, U.S. Pat. No. 6,768,044, U.S. Pat. No. 6,245,698, U.S. Pat. No. 6,268,549, and U.S. Pat. No. 6,118,050, the contents of each is herein incorporated by reference in its entirety. A review of the various structures of HPPD polypeptides from microbes, mammals and plants can be found, for example, in Moran et al. (2005) *Archives of Biochemistry and Biophysics* 433:117-128, herein incorporated by reference in its entirety.

HPPD polynucleotides may further comprise a chloroplast transit peptide (CTP) sequence to direct the transport of the expressed polypeptide to the chloroplast. CTP sequences are known. In one embodiment, the CTP sequence employed comprises a CTP as disclosed in U.S. Provisional application No. 61/393,507, entitled "Methods and Compositions for Targeting Sequences of Interest to the Chloroplast", filed Oct. 15, 2010.

As used herein, "hydroxyphenylpyruvate dioxygenase activity" or "HPPD activity" refers to the conversion of 4-hydroxyphenylpyruvate to homogentisate. As used herein, a polypeptide having "HPPD activity" comprises an HPPD polypeptide or an active variant or fragment thereof that retains sufficient HPPD activity such that (i) when expressed at sufficient levels in a cell that requires HPPD activity for viability, the HPPD polypeptide or active variant or fragment exhibits sufficient HPPD activity to maintain viability of the cell in which it is expressed; or (ii) when expressed in a cell that requires HPPD activity for viability, the HPPD polypeptide or active variant or fragment thereof, when expressed in combination with one or more additional HPPD polypeptides maintains the viability of the cell. As used herein, an "HPPD polynucleotide" refers to a polynucleotide encoding an active HPPD polypeptide.

HPPD activity can be assayed by utilizing the differences in light absorbance properties between 4-hydroxyphenylpyruvate (HPP) and maleylacetoacetate. HPPD catalyzes the conversion of HPP to homogentisate and homogentisate dioxygenase (HGD) catalyzes the conversion of homogentisate into maleylacetoacetate. While no difference in absorbance exists between HPP and homogentisate, a difference in absorbance can be observed at 320 nm between HPP and maleylacetoacetate. Thus, by combining HPP with both HPPD and HGD under the appropriate reaction conditions HPPD activity can be assayed.

As used herein, an "HPPD inhibitor" comprises any compound or combinations of compounds which decrease the ability of HPPD to catalyze the conversion of 4-hydroxyphenylpyruvate to homogentisate. In specific embodiments, the HPPD inhibitor comprises a herbicidal inhibitor of HPPD. Non-limiting examples of HPPD inhibitors include, triketones (such as, mesotrione, sulcotrione, topramezone, and tembotrione); isoxazoles (such as, pyrasulfotole and isoxaflutole); pyrazoles (such as, benzofenap, pyrazoxyfen, and pyrazolynate); and benzobicyclon. Agriculturally acceptable salts of the various inhibitors include salts, the cations or anions of which are known and accepted in the art for the formation of salts for agricultural or horticultural use. See, for example, WO2005/053407 herein incorporated by reference.

HPPD promoters and/or chimeric promoters disclosed herein can express HPPD polypeptides in different levels to provide different levels of tolerance to different HPPD-inhibitor herbicides. While a given promoter may provide a useful level of expression to offer tolerance to some HPPD-inhibitor herbicides it may be quite inadequate to provide expression levels to provide commercial levels of tolerance to a different HPPD-inhibitor herbicide which, for example, may control a different spectrum of weeds, be cheaper to make or offer environmental benefits. Thus, various promoters and HPPD polypeptides can be used in combination in a single plant, plant explant or plant cell to expand and/or improve the tolerance to a desired HPPD herbicide or combination of HPPD herbicides. Thus, in specific embodiments, the promoters and chimeric promoters disclosed herein are operably linked to an HPPD polynucleotide in order to allow sufficient expression of an active HPPD polypeptide, insensitive to HPPD inhibitors, to impart HPPD tolerance to the plant.

The insensitivity to an HPPD inhibitor can be determined by assaying the insensitivity of a cell, a plant, a plant cell expressing the HPPD polypeptide or active fragment or variant thereof. In such instances, the cell, plant, or plant cell expressing an HPPD sequence displays an insensitivity to an HPPD inhibitor or to a combination of HPPD inhibitors when compared to a control cell, plant or plant cell not expressing the HPPD sequence. "Increased tolerance" to a herbicide is demonstrated when plants which display the increased tolerance to a herbicide are subjected to the HPPD inhibitor and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially "resistant" or "tolerant" to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field.

G. Plants

Plants, plant cells, plant parts and seeds, and grain having the HPPD promoter and/or the chimeric promoter disclosed herein are provided. In specific embodiments, the plants and/or plant parts have stably incorporated at least one heterologous HPPD promoter or chimeric promoter disclosed herein or an active variant or fragment thereof. Thus, plants, plant cells, plant parts and seed are provided which comprise at least one heterologous HPPD promoter as set forth in any one of SEQ ID NO: 1, 2, 3, 4, 5, 6, 7, 8, 9, 10, 11, 12, 13, 14, 15, 16, 17, 18, 19, 20, 74, 75, or 76 or any one of other active fragments or variants disclosed herein. In another embodiment, the plants and/or plant parts have stably incorporated at least one heterologous chimeric promoter as disclosed herein or active variants or fragments thereof. Thus plants, plant cells, plant parts and seeds are provided which comprise at least one heterologous chimeric promoter as set forth in any on of SEQ ID NO: 23, 24, 25, 26, 27, 28, 29, 30, 31, 32, 33, 34, 35, 36, 37, 38, 39, 40, 41, 77, or 78 or active variants or fragments thereof. In specific embodiments, the HPPD promoter sequences are characterized as having transcriptional regulatory activity such that when the promoter sequence is operably linked to an HPPD polynucleotide having HPPD activity and insensitivity to an HPPD inhibitor, the HPPD polynucleotide is expressed in sufficient levels to impart tolerance of the plant to an HPPD inhibitor.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The promoter sequences and active variant and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments soybean plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, the polynucleotides comprising the HPPD promoter or the chimeric promoters operably linked to the polynucleotide encoding the polypeptide of interest are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Thus, in specific embodiments, the promoters and chimeric promoters disclosed herein are operably linked to an HPPD polynucleotide in order to allow sufficient expression of an active HPPD polypeptide, insensitive to HPPD inhibitors, to impart HPPD tolerance to the plant. Such constructs can then be stacked with any other sequence of interest, including any other herbicide tolerance conferring sequences. Non-limiting examples of such sequences are disclosed elsewhere herein. In some embodiments, the HPPD polynucleotides or active variants and fragments thereof disclosed herein are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term “stacked” includes having the multiple traits present in the same plant (i.e., both traits are incorporated into the nuclear genome, one trait is incorporated into the nuclear genome and one trait is incorporated into the genome of a plastid, or both traits are incorporated into the genome of a plastid). In one non-limiting example, “stacked traits” comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one HPPD inhibitor and/or at least one additional polynucleotide that confers tolerance to a second herbicide.

When one wants to express HPPD polypeptides, one can express such polypeptides as a stack, with promoters such as HPPD promoter polynucleotides, chimeric promoters, or any combination thereof. Thus, in one embodiment, the plants, plant cells or plant part having the promoters and chimeric promoters described herein operably linked to an HPPD polynucleotide or active variants or fragments thereof is stacked with at least one other HPPD sequence. Such HPPD sequence include the HPPD sequence and variants and fragment thereof disclosed herein, as well as other HPPD sequence, which include but are not limited to the HPPD sequences set forth in U.S. Pat. Nos. 6,245,968 B1; 6,268,549; and 6,069,115; and international publication WO 99/23886, each of which is herein incorporated by reference.

In still other embodiments, plants, plant cells, explants and expression cassettes comprising the promoters and chimeric promoters described herein operably linked to HPPD sequences or active variant and fragment thereof are stacked with a sequence that confers tolerance to HPPD inhibitors through a different mechanism than the HPPD polypeptide. For example, a P450 sequence could be employed which provides tolerance to HPPD-inhibitors by metabolism of the herbicide. Such sequences including, but are not limited to, the NSF1 gene. See, US 2007/0214515 and US 2008/0052797 both of which are herein incorporated by reference in their entirety.

In some embodiments, the plant or plant cells having the promoters and chimeric promoters described herein operably linked to HPPD polynucleotides or active variants or fragment thereof may be stacked with other herbicide-tolerance traits to create a transgenic plant of the invention with further improved properties. Other herbicide-tolerance polynucleotides that could be used in such embodiments include those conferring tolerance to glyphosate such as, for example, glyphosate N-acetyltransferase. See, for example, WO02/36782, US Publication 2004/0082770 and WO 2005/012515, U.S. Pat. No. 7,462,481, U.S. Pat. No. 7,405,074, each of which is herein incorporated by reference.

Additional glyphosate-tolerance traits include a sequence that encodes a glyphosate oxido-reductase enzyme as described more fully in U.S. Pat. Nos. 5,776,760 and 5,463,175. Other traits that could be combined with the HPPD sequence disclosed herein include those derived from polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747. Other traits that could be combined with the HPPD sequences include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In other embodiments, the plants or plant cell or plant part having the promoters and chimeric promoters described herein operably linked to an HPPD sequence or an active variant or fragment thereof is stacked with, for example, a sequence which confers tolerance to an ALS inhibitor. As used herein, an “ALS inhibitor-tolerant polypeptide” comprises any polypeptide which when expressed in a plant confers tolerance to at least one ALS inhibitor. A variety of ALS inhibitors are known and include, for example, sulfonylurea, imidazolinone, triazolopyrimidines, pryimidinyoxy(thio)benzoates, and/or sulfonylaminocarbonyltriazolinone herbicides. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio)benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. The soybean, maize, and *Arabidopsis* HRA sequences are disclosed, for example, in WO2007/024782, herein incorporated by reference.

In some embodiments, the ALS inhibitor-tolerant polypeptide confers tolerance to sulfonylurea and imidazolinone herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

In further embodiments, the plants or plant cell or plant part having the promoters and chimeric promoters described herein operably linked to an HPPD sequence or an active variant or fragment thereof is stacked with, or example, a sequence which confers tolerance to an ALS inhibitor and glyphosate tolerance. In one embodiment, the promoters described hererin operably linked to a HPPD sequence or active variant or fragment thereof is stacked with HRA and a glyphosate N-acetyltransferase. See, WO2007/024782, 2008/0051288 and WO 2008/112019, each of which is herein incorporated by reference.

In still other embodiments, the plant or plant cell or plant part having the promoters and chimeric promoters described herein operably linked to a HPPD sequence or an active variant or fragment thereof may be stacked with, for example, aryloxyalkanoate dioxygenase polynucleotides (which confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767, auxin polypeptides and an acetyl coenzyme A carboxylase (ACCase) polypeptides.

Other examples of herbicide-tolerance traits that could be combined with the plant or plant cell or plant part having the promoters and chimeric promoters described herein operably linked to a HPPD sequence or an active variant or fragment thereof include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the plants or plant cell or plant part having the promoters and chimeric promoters described herein operably linked to a HPPD sequence or an active variant or fragment thereof include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the plants or plant cell or plant part having the promoters and chimeric promoters described herein operably linked to a HPPD sequence or an active variant or fragment thereof include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the plants or plant cell or plant part having the HPPD sequence or an active variant or fragment thereof to provide a plant of the invention as well as methods of use thereof.

In still further embodiments, the HPPD sequences operably linked to the promoters and chimeric promoters described herein can be stacked with at least one polynucleotide encoding a homogentisate solanesyltransferase (HST). See, for example, WO2010023911 herein incorporated by reference in its entirety. In such embodiments, classes of herbicidal compounds—which act wholly or in part by inhibiting HST can be applied over the plants having the HTS polypeptide.

The plant or plant cell or plant part having the HPPD sequence or an active variant or fragment thereof operably linked to the promoters and chimeric promoters described herein can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The plant or plant cell or plant part having the HPPD sequence or an active variant or fragment thereof operably linked to the promoters and chimeric promoters described herein can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In other embodiments, the plant or plant cell or plant part having the HPPD sequence or an active variant or fragment thereof operably linked to the promoters and chimeric promoters described herein may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al, (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In another embodiment, the plant or plant cell or plant part having the HPPD sequence or an active variant or fragment thereof operably linked to the promoters and chimeric promoters described herein can also be combined with the Rcg1 sequence or biologically active variant or fragment thereof. The Rcg1 sequence is an anthracnose stalk rot resistance gene in corn. See, for example, U.S. patent application Ser. Nos. 11/397,153, 11/397,275, and 11/397,247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

II. Methods of Introducing

The methods of the invention comprise regulating the expression of a polynucleotide of interest by stably incorporating a polynucleotide comprising a HPPD promoter and/or a chimeric promoter disclosed herein into the genome of a plant or plant cell. The methods provided herein do not depend on a particular method for introducing a sequence into the host cell, only that the polynucleotide gains access to the interior of at least one cell of the host. Methods for introducing polynucleotides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide is introduced into the host (i.e., a plant) and expressed temporally.

Transformation protocols as well as protocols for introducing polynucleotide sequences into plants may vary depending on the type of plant or plant cell, i.e., monocot or dicot, targeted for transformation. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev.*

*Genet.* 22:421-477; Sanford et al. (1987) *Particulate Science and Technology* 5:27-37 (onion); Christou et al, (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. Methods of homologous recombination can also be employed. See, for example, US Publication No. 2010-0192253 and WO20051049842

In specific embodiments, the HPPD promoter and/or chimeric promoter disclosed herein can be provided to a plant using a variety of transient transformation methods. Such transient transformation methods include, but are not limited to, the introduction of the promoter polynucleotides or variants and fragments thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the HPPD promoter polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In other embodiments, HPPD promoter and/or chimeric promoter disclosed herein may be introduced into plants by contacting plants with a virus or viral nucleic acids. Generally, such methods involve incorporating a nucleotide construct of the invention within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having an HPPD promoter and/or chimeric promoter disclosed herein, stably incorporated into their genome.

III. Methods of Use

A method for modulating the expression of a polynucleotide of interest is provided. Such methods comprise stably incorporating in the genome of a plant or plant cell a polynucleotide sequence of interest operably linked to an HPPD promoter and/or chimeric promoter as described herein.

Depending on the polynucleotide of interest operably linked to the HPPD promoter and/or chimeric promoter as described herein, the transgenic plants, plant cells or seeds may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like.

In specific embodiments, the HPPD promoters and/or chimeric promoters of the invention modulate expression of an HPPD polynucleotide. Methods disclosed herein employ the HPPD promoters and/or chimeric promoters of the invention to express polynucleotides of interest encoding polypeptides conferring tolerance to herbicides, as described in detail elsewhere herein. In specific embodiments, the HPPD promoters and/or chimeric promoters of the invention modulate expression of a polynucleotide of interest in any plant. In specific embodiments, the plant comprises a dicot, and in further embodiments the dicot is soybean.

In some embodiments, the promoters and chimeric promoters disclosed herein modulate expression of an HPPD polynucleotide encoding an HPPD polypeptide having HPPD activity and having insensitivity to HPPD inhibitors such that the plant is tolerant to the HPPD inhibitors. Thus, a method of controlling weeds is provided comprising planting a plant or seed comprising the chimeric promoter and/or HPPD promoter disclosed herein operably linked to a polynucleotide encoding an HPPD polypeptide that is insensitive to an HPPD inhibitor and retains HPPD activity. An effective amount of an HPPD inhibitor is applied to the seed, plant, and/or area of cultivation, such that the growth of the weeds in the field is controlled and/or prevented and/or reduced. In such an embodiment, the transcriptional regulatory activity of the HPPD promoter or the chimeric promoter is sufficient to direct transcription of the HPPD polypeptide at sufficient levels and/or at a specific temporal and/or tissue specific matter to confer to the plant tolerance to the HPPD inhibitor.

Soybean HPPD Proteins and Methods of Use

Compositions are further provided comprising the soybean HPPD protein comprising the native soybean HPPD CTP, the polynucleotide encoding the same, and active variants and fragments thereof. Such sequences include the polynucleotide set forth in SEQ ID NO: 57 and the polypeptide set forth in SEQ ID NO: 58, and active variants and fragments thereof. Such polypeptides are capable of being transported into the chloroplast of a plant cell. In some embodiments, the polynucleotide set forth in SEQ ID NO: 57 or an active variant or fragment thereof is operably linked to a heterologous promoter. See, for example, U.S. Utility application Ser. No. 13/208,966 entitled "Compositions and Methods Comprising Sequences Having Hydroxyphenylpyruvate Dioxygenase (HPPD) Activity" filed concurrently herewith and herein incorporated by reference.

In specific embodiments, active fragments and variants of the HPPD sequence as set forth in SEQ ID NO: 57 are provided. Such fragments comprise at least 16, 20, 50, 75, 100, 150, 200, 250, 300, 350, 400, 450, 500, 550, 600, 650, 700, 800, 900, 1,000, 1,100, 1,200, 1,300, or 1,450 contiguous nucleotides, or up to the number of nucleotides present in SEQ ID NO: 57. Generally, variants of SEQ ID NO: 57 will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 57 as determined by sequence alignment programs and parameters described elsewhere herein. Active fragments and variants of SEQ ID NO: 57 will continue to encode a polypeptide having HPPD activity and which can be transported into the chloroplast of a plant cell.

Figure 5:
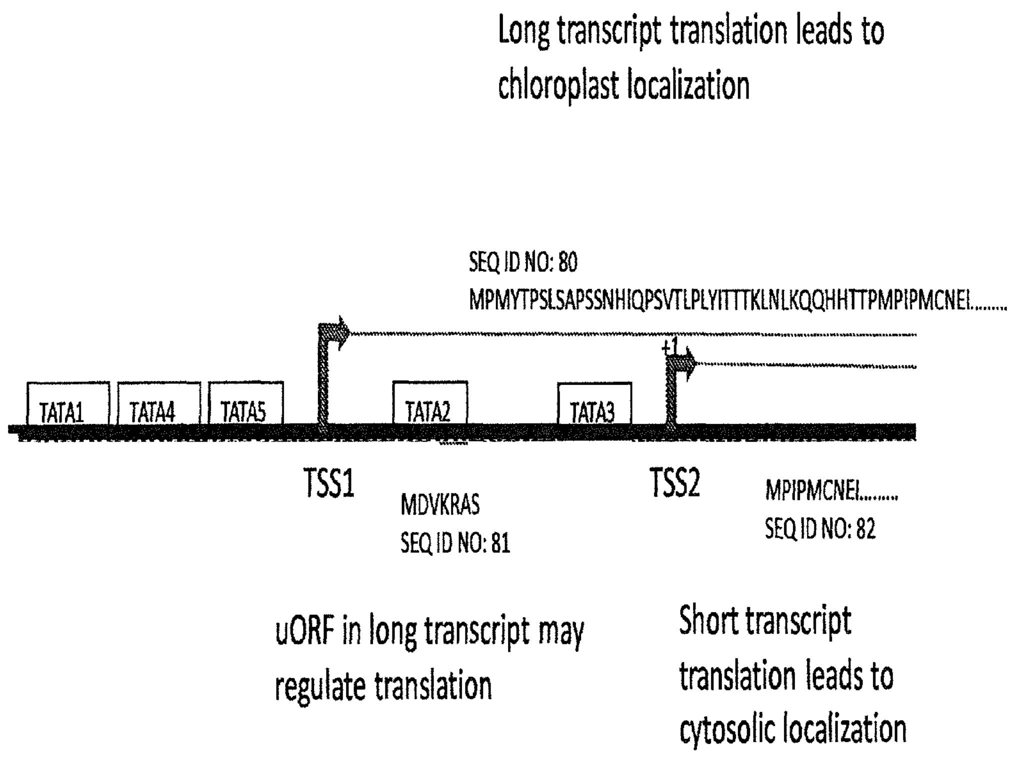
FIG. 5 depicts the *Glycine max* HPPD promoter and separate transcripts.
Figure 6:
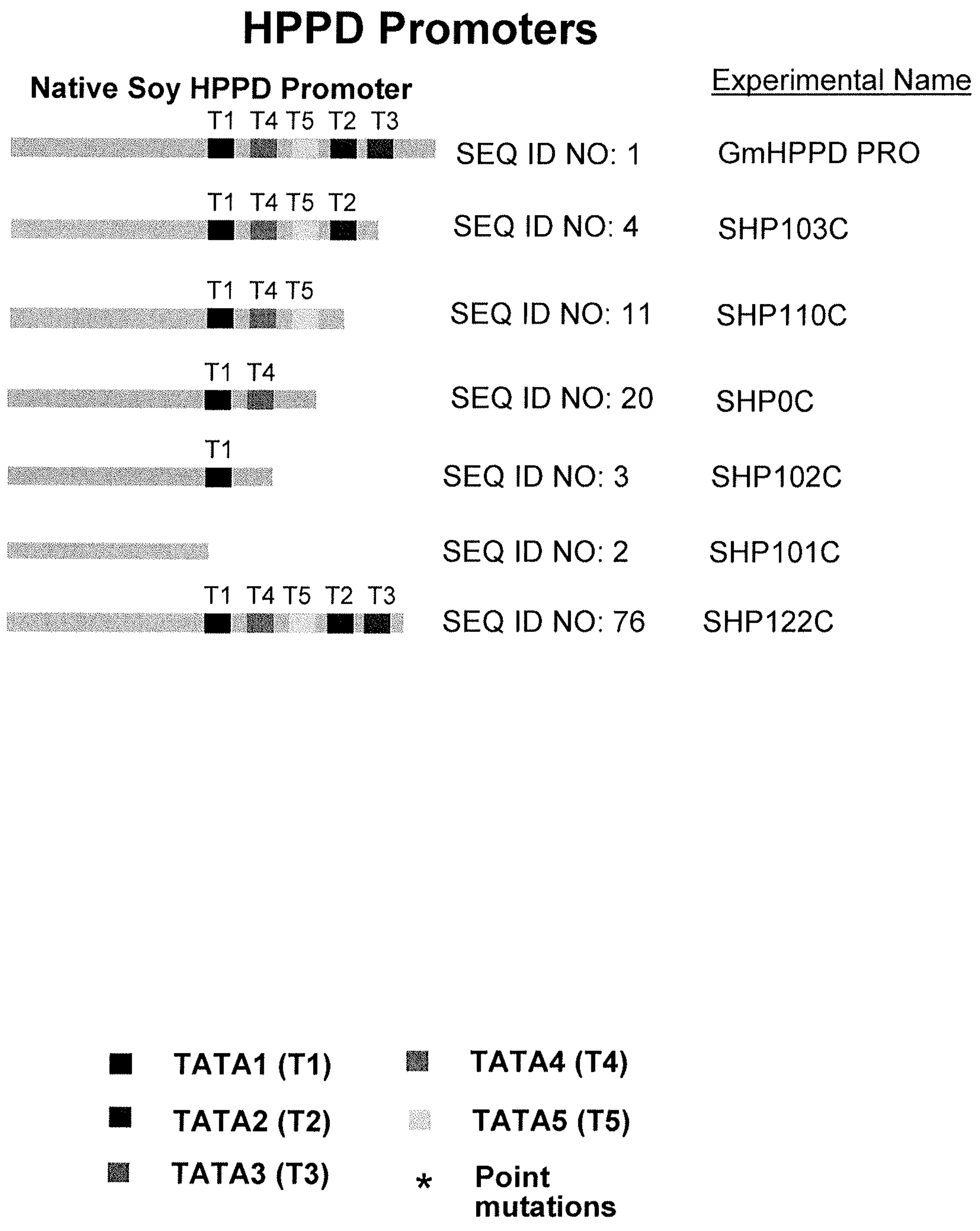
FIG. 6 shows schematics of the HPPD promoters described herein. TATA motifs are indicated by T1 (TATA1), T2 (TATA2), T3 (TATA3), T4 (TATA4), and T5 (TATA5).
Figure 7:
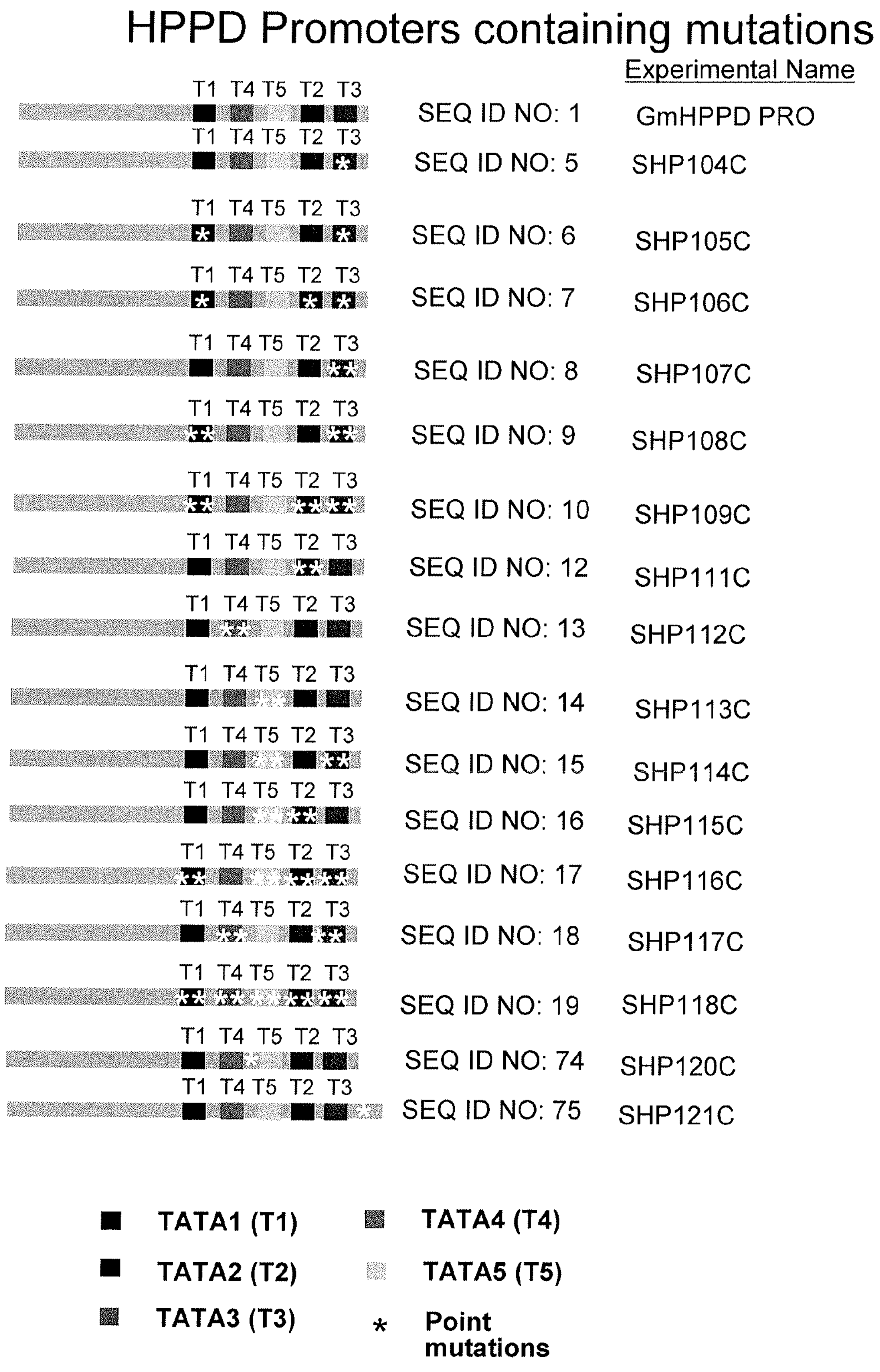
FIG. 7 shows schematics of the HPPD promoters having mutations within the TATA motif. Nucleotide point mutations are indicated by a "*" within the appropriate TATA motif.
Figure 9:
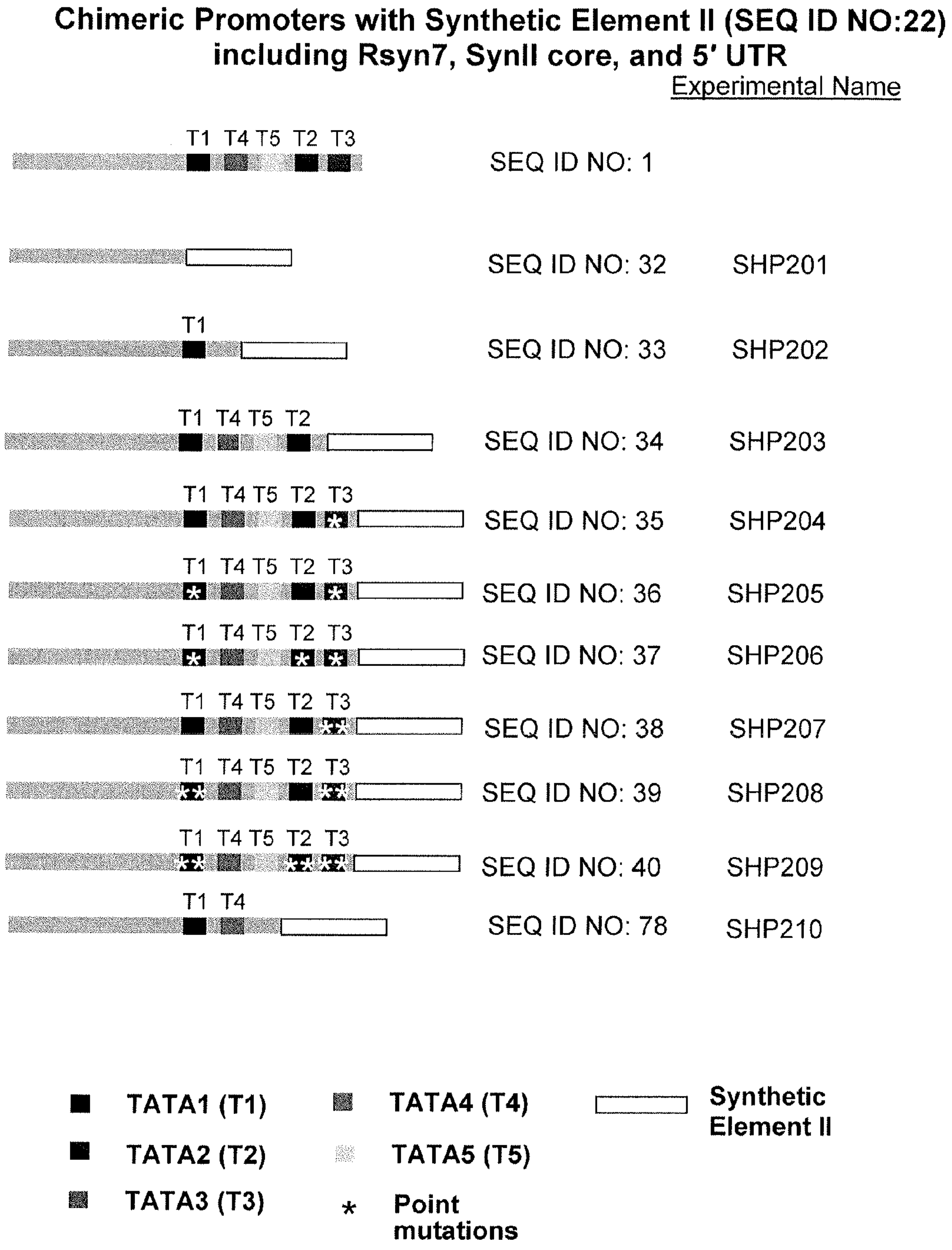
FIG. 9 shows schematics of the chimeric promoters described herein comprising a regulatory region of an HPPD promoter operably linked to synthetic element II (SEQ ID NO: 22). TATA motifs are indicated by T1 (TATA1), T2

The HPPD promoter as described in SEQ ID NO:1 leads to the production of at least two major transcripts from at least two transcription start sites (TSS1 and TSS2, see FIG. 5). The longer transcript initiates SEQ ID NO: 57 (encoding SEQ ID NO: 58). Parts of the genomic sequence transcribed to produce the longer transcript also act to promote transcriptional regulatory activity for the shorter transcript that initiates SEQ ID NO: 79 (encoding SEQ ID NO: 61). Various polynucleotide sequences are known in the art comprising multiple transcriptional start sites that encode products targeted to multiple cellular compartments. See for example, Small, *Plant Mol. Biol.,* 1998, 38:265-277 and Thatcher, *J of Biol. Chem.,* 2007, 282:28915-28928. SEQ ID NO: 58 polypeptide is localized to the chloroplast, while SEQ ID NO: 61 polypeptide is localized to the cytosol.

Further provided are variant HPPD proteins as set forth in SEQ ID NO: 58. "Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, HPPD activity and wherein the protein is transported into the chloroplast of a plant cell. Such variants may result from, for example, genetic polymorphism or from human manipulation. Biologically active variants of a HPPD proteins disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 58 as determined by sequence alignment programs and parameters described elsewhere herein. A biologically active variant of a protein of the invention may differ from SEQ ID NO: 58 by as few as 1-15 amino acid residues, as few as 1-10, such as 6-10, as few as 5, as few as 4, 3, 2, or even 1 amino acid residue.

Fragments of amino acid sequences include peptides comprising amino acid sequences sufficiently identical to or derived from the amino acid sequence of a HPPD protein, or a partial-length protein and exhibiting HPPD activity but which include fewer amino acids than the full-length HPPD-related proteins disclosed herein. A biologically active portion of a HPPD protein can be a polypeptide that is, for example, 10, 25, 50, 100, 150, 200 contiguous amino acids in length, or up to the total number of amino acids present in a full-length HPPD protein of the current invention (i.e., of SEQ ID NO: 58). Such biologically active portions can be prepared by recombinant techniques and evaluated for one or more of the functional activities of a native HPPD protein, including but not limited to transport into the chloroplast of a plant cell. As used herein, a fragment comprises at least 5 contiguous amino acids of SEQ ID NO: 58. The invention encompasses other fragments, however, such as any fragment in the protein greater than 6, 7, 8, or 9 amino acids.

The polynucleotide encoding SEQ ID NO: 58 or active fragments and variants thereof can be provided in an expression cassette for expression in a plant or organism of interest. The expression cassette can include 5' and 3' regulatory sequences operably linked to the polynucleotide of the invention. An operable linkage between a polynucleotide of interest and a regulatory sequence (i.e., a promoter) is a functional link that allows for expression of the polynucleotide of interest. Operably linked elements may be contiguous or non-contiguous. In some embodiments, the polynucleotide set forth in SEQ ID NO: 57 can be operably linked to a heterologous promoter. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

Further provided are plants, plant cells, and seeds having a heterologous polynucleotide construct comprising an expression cassette having a promoter operably linked to a polynucleotide encoding the polypeptide set forth in SEQ ID NO: 58 or an active variant or fragment thereof, wherein the promoter is heterologous to said polynucleotide.

Chloroplast Transit Peptides

The compositions provided herein further include recombinant polynucleotides comprising a nucleotide sequence encoding a novel chloroplast transit peptide (CTP) operably linked to a nucleotide sequence encoding a polypeptide of interest. In one embodiment, the CTP comprises the polypeptide sequence set forth in SEQ ID NO: 60, or active variants or fragments thereof, or comprises the polynucleotide sequence as set forth in SEQ ID NO: 59, or active variants and fragments thereof. Such CTP-encoding sequences, when assembled within a DNA construct such that the CTP-encoding sequence is operably linked to a nucleotide sequence encoding the polypeptide of interest, facilitate co-translational or post-translational transport of the peptide of interest to the chloroplast of a plant cell. See, for example, U.S. Utility application Ser. No. 13/208,960, entitled "Methods and Compositions for Targeting Sequences of Interest to a Chloroplast" filed concurrently herewith and herein incorporated by reference.

Fragments and variants of the CTP-sequences (i.e. SEQ ID NO: 59 and 60) are also encompassed herein. By "fragment" is intended a portion of the polynucleotide or a portion of the amino acid sequence and hence protein encoded thereby. Fragments of a polynucleotide may encode protein fragments that retain CTP activity when reconstituted in a CTP and are thus capable of facilitating the translocation of a polypeptide of interest into the chloroplast of a plant. Thus, fragments of a nucleotide sequence may range from at least about 10, 20, 30, 40, 50, 60, 70, 80 nucleotides or up to the full length CTP.

A fragment of a polynucleotide that encodes a biologically active portion of a CTP-polypeptide will encode at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 contiguous amino acids, or up to the total number of amino acids present in SEQ ID NO: 60.

"Variant" CTP is intended to mean a protein derived from the CTP (i.e. SEQ ID NO: 60) by deletion (i.e., truncation at the 5' and/or 3' end) and/or a deletion or addition of one or more amino acids at one or more internal sites in the CTP and/or substitution of one or more amino acids at one or more sites in the CTP, and/or substitution of one or more of the N-terminal, central, or C-terminal domains of the CTP and/or substitution of a portion of one or more of the N-terminal, central, or C-terminal domains of the CTP. Variant proteins encompassed are biologically active, that is they continue to possess the desired biological activity of the CTP, that is, have CTP activity when reconstituted in a CTP. Such variants may result from, for example, genetic polymorphism or from human manipulation.

Biologically active variants of a CTP provided herein (and the polynucleotide encoding the same) will have at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the polypeptide of SEQ ID NO: 60 or to any N-terminal domain or portion thereof, any central domain or portion thereof or any C-terminal domain or portion thereof from any one of SEQ ID NOS: 60 or any of the other CTPs disclosed herein. Variants of CTP polynucleotides provided herein will have at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the polynucleotide of SEQ ID NO: 59, and encode an active CTP.

The CTP-sequences and the active variants and fragments thereof may be altered in various ways including amino acid substitutions, deletions, truncations, and insertions. Methods for such manipulations are generally known in the art. For example, amino acid sequence variants and fragments of the CTPs can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different CTP-sequences can be manipulated to create a new CTP possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the CTP sequences disclosed herein and other known CTPs to obtain a new polynucleotide coding for a polypeptide with an improved property of interest, such as an improved efficiency of transport to the chloroplast. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences encoding the CTPs disclosed herein (i.e., SEQ ID NO: 60, 59 or active variant or fragments thereof) can be operably linked to any polynucleotide of interest. Such constructs, when operably linked to a promoter active in a plant, will allow for the translocation of the encoded polypeptide to the chloroplast. Thus, further provided are plants, plant cells and seed having stably incorporated into their genome a DNA construct comprising a promoter active in a plant operably linked to a nucleotide sequences encoding the CTP sequences disclosed herein (i.e., SEQ ID NO: 60, 59 or active variant or fragments thereof) operably linked to any polynucleotide of interest.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

TABLE 1

| SEQ ID NO: | Description |
|---|---|
| 1 | Nucleotide sequence of native *Glycine max* HPPD region 5' to annotated ATG gene coding region start site, comprising the HPPD promoter. |
| 2 | SHP101C, 613 nucleotide deletion in the 3'end of seq. 1 (with KpnI site added at the end) |
| 3 | SHP102C, 485 nucleotide deletion in the 3'end of seq. 1 (with KpnI site added at the end) |
| 4 | SHP103C, 122 nucleotide deletion in the 3'end of seq. 1 (with KpnI site added at the end) |
| 5 | SHP104C, A to C point mutation of seq. 1 at position −20 relative to putative transcription start site (with KpnI site added at the end). |
| 6 | SHP105C, T to C point mutation of seq. 5 at position −563 relative to the putative transcription site (with KpnI site added at the end). |
| 7 | SHP106C, T to G point mutation of seq. 6 at position −190 relative to the putative transcription site (with KpnI site added at the end). |
| 8 | SHP107C, TAT to GCA mutation of seq. 1 at position −21 relative to the putative transcription site (with KpnI site added at the end). |
| 9 | SHP108C, ATA to CCG mutation of seq. 8 at position −564 relative to the putative transcription site (with KpnI site added at the end). |
| 10 | SHP109C, TAT to CAG mutation of seq. 9 at position −192 relative to the putative transcription site (with KpnI site added at the end). |
| 11 | SHP110C, 227 nucleotide deletion in the 3'end of seq. 1 (with KpnI site added at the end). |
| 12 | SHP111C, TAT to CAG mutation of seq. 1 at position −192 relative to the putative transcription site (with KpnI site added at the end). |
| 13 | SHP112C, TAT to CAG mutation of seq. 1 at position −396 relative to the putative transcription site (with KpnI site added at the end). |
| 14 | SHP113C, TAT to CAG mutation of seq. 1 at position −263 relative to the putative transcription site (with KpnI site added at the end). |
| 15 | SHP114C, TAT to CAG mutation of seq. 8 at position −263 relative to the putative transcription site (with KpnI site added at the end). |
| 16 | SHP115C, TAT to CAG mutation of seq. 12 at position −263 relative to the putative transcription site (with KpnI site added at the end). |
| 17 | SHP116C, TAT to CAG mutation of seq. 10 at position −263 relative to the putative transcription site (with KpnI site added at the end). |
| 18 | SHP117C, TAT to CAG mutation of seq. 8 at position −396 relative to the putative transcription site (with KpnI site added at the end). |
| 19 | SHP118C, TAT to CAG mutation of seq. 17 at position −396 relative to the putative transcription site (with KpnI site added at the end). |
| 20 | SHP0C, 314 nucleotide deletion in the 3'end of seq. 1 (with KpnI site added at the end). |
| 21 | Element I including SynII core and soy 5'UTR (with KpnI site added at the end). |
| 22 | Element II including Rsyn7, SynII core, and soy 5'UTR (with KpnI site added at the end). |
| 23 | SHP101, seq. 21 joined at 3' end of seq. 2. |
| 24 | SHP102, seq. 21 joined at 3' end of seq. 3. |
| 25 | SHP103, seq. 21 joined at 3' end of seq. 4. |
| 26 | SHp104, seq. 21 joined at 3' end of seq. 5. |
| 27 | shp105, seq. 21 joined at 3' end of seq. 6. |
| 28 | Shp106, seq. 21 joined at 3' end of seq. 7. |
| 29 | shp107, seq. 21 joined at 3' end of seq. 8. |
| 30 | shp108, seq. 21 joined at 3' end of seq. 9. |
| 31 | shp109, seq. 21 joined at 3' end of seq. 10. |
| 32 | shp201, seq. 22 joined at 3' end of seq. 2. |
| 33 | shp202, seq. 22 joined at 3' end of seq. 3. |
| 34 | shp203, seq. 22 joined at 3' end of seq. 4. |
| 35 | shp204, seq. 22 joined at 3' end of seq. 5. |
| 36 | shp205, seq. 22 joined at 3' end of seq. 6. |
| 37 | shp206, seq. 22 joined at 3' end of seq. 7. |
| 38 | shp207, seq. 22 joined at 3' end of seq. 8. |
| 39 | shp208, seq. 22 joined at 3' end of seq. 9. |
| 40 | shp209, seq. 22 joined at 3' end of seq. 10. |
| 41 | SHP110, TATA5 of SEQ ID NO: 1 is replaced by the partial SynII core (SEQ ID NO 71) |
| 42 | Forward primer: GCAAGTATTTCAATACAATAGC |
| 43 | Reverse primer: GTTATCTGATATGATGTTGC |
| 44 | TATA1: GTATAAATAA |
| 45 | TATA2: CCAATATATG |
| 46 | TATA3: CCTTATATATC |
| 47 | TATA4: TATATAATAA |
| 48 | TATA5: GAATATAAG |
| 49 | 5' fragment of "long" HPPD protein: GTAATAAAAAAAGAGAGAAGCCGCATCAA |
| 50 | 5' fragment of "short" HPPD protein: AAGCAGCAGCATCACACCACACCAATGCC |
| 51 | Forward primer hp0234: GTTTTCCGCGGGTGTTGATCC |
| 52 | Reverse primer hp2296: TCATTGGTACCTGGTGTGGTGTGATGCTGC |

TABLE 1-continued

| SEQ ID NO: | Description |
|---|---|
| 53 | Reverse primer hp2154: AGCATGGTACCTTGCGTCTGGGTTGAG |
| 54 | Reverse primer hp1962: AGGAGGTACCGTCAAATCCACCTAG |
| 55 | Reverse primer hp1663: TCCTTGGTACCTGATGCACTATATAACG |
| 56 | Putative 5' UTR: ACAACCACCAAGCTCAATCTCAAGCAGCAGCATCACACCACACCA |
| 57 | Nucleotide sequence of the soybean HPPD polynucleotide (including the region encoding the native CTP) predicted from the longer transcript (5'TSS) |
| 58 | Amino Acid sequence of the soybean HPPD including the native CTP |
| 59 | 5' region of SEQ ID NO: 57 encoding native CTP |
| 60 | N-terminal region of SEQ ID NO: 58 comprising native soybean CTP |
| 61 | Soybean HPPD protein predicted from shorter transcript (3' TSS) |
| 62 | Reverse primer hp2048: ATCTGGTACCTGATGTTGATGCGGC |
| 63 | Reverse primer hp1791: AGCCTGGTACCTTGTGTGTAAAAAAGATAAGAC |
| 64 | Upstream HPPD genomic sequence of *Arabidopsis thaliana* |
| 65 | Upstream HPPD genomic sequence of *Medicago truncatula* |
| 66 | Upstream HPPD genomic sequence of Poplar |
| 67 | Upstream HPPD genomic sequence of *Brassica rapa* |
| 68 | Upstream genomic sequence of *Vitis vinifera* |
| 69 | Upstream HPPD genomic sequence of *Sorghum bicolor* |
| 70 | SynII core (SEQ ID NO: 1 from U.S. Pat. No. 6,072,050) |
| 71 | Partial SynII core sequence (containing TATA box and transcriptional start site) used to construct Element I and II |
| 72 | Predicted HPPD 5'UTR |
| 73 | Rsyn7 (U.S. Pat. No. 6,072,050 SEQ ID 2) |
| 74 | SHP120C; A to T mutation at nucleotide 1945 of SEQ ID NO: 1; this eliminates the start codon of the upORF element |
| 75 | SHP121C; A to T mutation at nucleotide 2128 of SEQ ID NO: 1; this introduces a translation stop codon just upstream of the +7 transcription start site |
| 76 | SHP122C; deletion of everything downstream of nucleotide 2040 in SEQ ID NO: 1 |
| 77 | SHP111; deletion of TATA3 through transcription start site at +7 (nucleotide 2106-2140 of SEQ ID NO: 1) and replaced with the Partial SynII Core |
| 78 | SHP210; deletion of TATA5 through transcription start site at −231 (1867-1905 of SEQ ID NO: 1) and replaced with Element III (SEQ ID NO: 83) |
| 79 | Nucleotide sequence of the soybean HPPD protein predicted from the shorter transcript (3' TSS) |
| 80 | Amino acid sequence of N-terminal end of longer HPPD transcript (*G. max*) |
| 81 | Predicted upstream ORF in longer HPPD transcript (*G. max*) |
| 82 | Amino acid sequence of N-terminal end of shorter HPPD transcript (*G. max*) |
| 83 | Element III, partial Element II (SEQ ID 22) sequence including Rsyn7 and SynII Core |

Non-limiting embodiments include:

1. A chimeric promoter construct comprising
 a first polynucleotide comprising a regulatory region of a 4-hydroxyphenylpyruvate dioxygenase (HPPD) promoter operably linked to a second polynucleotide comprising a heterologous core promoter functional in a plant,
 wherein said core promoter modulates the regulatory activity of said regulatory region of the HPPD promoter when compared to the regulatory activity of said regulatory region of the HPPD promoter alone;
 wherein said chimeric promoter has transcriptional regulatory activity in a plant.

2. The chimeric promoter construct of embodiment 1, wherein said regulatory region of the HPPD promoter comprises a variant or a fragment of SEQ ID NO:1.

3. The chimeric promoter construct of embodiment 2, wherein said transcriptional regulatory activity of said regulatory region of the HPPD promoter in the absence of said core promoter comprises less than 10% of the transcriptional regulatory activity of the HPPD promoter set forth in SEQ ID NO: 1.

4. The chimeric promoter construct of embodiment 2, wherein said transcriptional regulatory activity of said regulatory region of the HPPD promoter in the absence of said core promoter comprises at least 10% of the regulatory activity of the HPPD promoter as set forth in SEQ ID NO: 1.

5. The chimeric promoter construct of any one of embodiments 1-4, wherein said regulatory region of the HPPD promoter comprises a deletion selected from the group consisting of:
 (a) a deletion of a TATA motif; or
 (b) a deletion of at least one of the TATA1, TATA2, TATA3, TATA4 or TATA5 motifs.

6. The chimeric promoter construct of embodiment 5, wherein said regulatory region of the HPPD promoter comprises
 a) the polynucleotide set forth in any one of SEQ ID NO: 2, 3, 4, 11 or 20;
 b) a polynucleotide having at least 90% sequence identity to any one of SEQ ID NO: 2, 3, 4, 11, or 20; or
 c) a polynucleotide comprising a fragment comprising at least 300 consecutive nucleotides of SEQ ID NO: 2, 3, 4, 11, or 20.

7. The chimeric promoter construct of any one of embodiments 1-4, wherein said regulatory region of the HPPD promoter comprises at least one or more alterations in at least one of the TATA1, TATA2, TATA3, TATA4 or TATA5 elements.

8. The chimeric promoter construct of embodiment 7, wherein said regulatory region of the HPPD promoter comprises a) the polynucleotide set forth in any one of SEQ ID NO: 5, 6, 7, 8, 9, 10, 12, 13, 14, 15, 16, 17, 18, or 19;
b) a polynucleotide having at least 90% sequence identity to any one of SEQ ID NO: 5, 6, 7, 8, 9, 10, 12, 13, 14, 15, 16, 17, 18, or 19; or
c) a polynucleotide comprising a fragment comprising at least 300 consecutive nucleotides of SEQ ID NO: 5, 6, 7, 8, 9, 10, 12, 13, 14, 15, 16, 17, 18, or 19.

9. The chimeric promoter construct of any one of embodiments 1-8, wherein said core promoter increases the regulatory activity of said regulatory region of the HPPD promoter when compared to the regulatory activity of said regulatory region of the HPPD promoter alone.

10. The chimeric promoter construct of any one of embodiments 1-8, wherein said core promoter decreases the regulatory activity of said regulatory region of the HPPD promoter when compared to the regulatory activity of said regulatory region of the HPPD promoter alone.

11. The chimeric promoter construct of any one of embodiments 1-8, wherein said transcriptional regulatory activity of said chimeric promoter construct mimics the level of transcriptional regulatory activity of the HPPD promoter set forth SEQ ID NO:1.

12. The chimeric promoter construct of any one of embodiments 1-11, wherein said chimeric promoter, when operably linked to a polynucleotide encoding a HPPD polypeptide having HPPD activity and insensitivity to an HPPD inhibitor, allows for a sufficient level of expression of said HPPD polypeptide in a plant to impart tolerance of the plant to an HPPD inhibitor.

13. The chimeric promoter construct of any one of embodiments 1-12, wherein said core promoter comprises
a) the polynucleotide set forth in SEQ ID NO:71;
b) a polynucleotide having at least 90% sequence identity to SEQ ID NO:71, where said polynucleotide continues to have core promoter activity;
c) a polynucleotide comprising a fragment comprising at least 30 consecutive nucleotides of SEQ ID NO: 71;
d) the polynucleotide set forth in SEQ ID NO: 21; or
e) the polynucleotide set forth in SEQ ID NO: 83.

14. The chimeric promoter construct of embodiment 13, wherein said core promoter further comprises
a) a second polynucleotide as set forth in SEQ ID NO:72;
b) a second polynucleotide having at least 90% sequence identity to SEQ ID NO:72, where said second polynucleotide modulates the activity of the core promoter; or
c) a second polynucleotide comprising a fragment comprising at least 20 consecutive nucleotides of SEQ ID NO: 72.

15. The chimeric promoter construct of embodiment 13 or 14, wherein said core promoter further comprises
a) the polynucleotide set forth in SEQ ID NO:73;
b) a polynucleotide having at least 90% sequence identity to SEQ ID NO:73, where said polynucleotide continues to have core promoter activity;
c) a polynucleotide comprising a fragment comprising at least 30 consecutive nucleotides of SEQ ID NO: 73; or
d) the polynucleotide set forth in SEQ ID NO: 22.

16. The chimeric promoter construct of any one of embodiments 1-15, wherein said polynucleotide comprises
a) the sequence set forth in SEQ ID NO: 23, 24, 25, 26, 27, 28, 29, 30, 31, 32, 33, 34, 35, 36, 37, 38, 39, 40, 41, 74, 75, 76, 77, or 78;
b) a sequence having at least 85% sequence identity to the sequence set forth in SEQ ID NO: 23, 24, 25, 26, 27, 28, 29, 30, 31, 32, 33, 34, 35, 36, 37, 38, 39, 40; 41, 74, 75, 76, 77, or 78 or
c) a polynucleotide comprising a fragment comprising at least 300 consecutive nucleotides of SEQ ID NO: 23, 24, 25, 26, 27, 28, 29, 30, 31, 32, 33, 34, 35, 36, 37, 38, 39, 40, 41, 74, 75, 76, 77, or 78.
d) a polynucleotide comprising a fragment comprising at least 300 consecutive nucleotides of a sequence having at least 85% sequence identity to the sequence set forth in SEQ ID NO: 23, 24, 25, 26, 27, 28, 29, 30, 31, 32, 33, 34, 35, 36, 37, 38, 39, 40, 41, 74, 75, 76, 77, or 78.

17. An expression cassette comprising a promoter operably linked to a polynucleotide of interest, wherein said promoter comprises the chimeric promoter construct of any one of embodiments 1-16.

18. The expression cassette of embodiment 17, wherein said polynucleotide of interest encodes a polypeptide or a suppression element.

19. The expression cassette of embodiment 18, wherein said polynucleotide of interest encodes an HPPD polypeptide having HPPD activity and having insensitivity to an HPPD inhibitor.

20. An expression vector comprising the expression cassette of any one of embodiments 17-19.

21. A plant having stably incorporated into its genome at least one expression cassette of any one of embodiments 17-19.

22. The plant of embodiment 21, wherein said plant is a dicot.

23. The plant of embodiment 22, wherein said dicot is soybean.

24. The plant of embodiment 22, wherein said dicot is *Brassica*, sunflower, cotton, or alfalfa.

25. The plant of embodiment 21, wherein said plant is a monocot.

26. The plant of embodiment 25, wherein said monocot is maize, wheat, rice, barley, sorghum, or rye.

27. A method of regulating the expression of a polynucleotide of interest, said method comprising stably incorporating in the genome of a plant or plant cell the polynucleotide sequence of interest operably linked to a promoter wherein said promoter comprises the chimeric polynucleotide of any one of embodiments 1-16 or stably incorporating in the genome of the plant or plant cell an expression cassette of any one of embodiments 17-20.

28. The method of embodiment 27, wherein said plant is a dicot.

29. The method of embodiment 28, wherein said dicot is soybean.

30. The method of embodiment 28, wherein said dicot is *Brassica*, sunflower, cotton, or alfalfa.

31. The method of embodiment 27, wherein said plant is a monocot.

32. The method of embodiment 31, wherein said monocot is maize, wheat, rice, barley, sorghum, or rye.

33. A polynucleotide comprising a promoter capable of regulating transcription comprising:
(a) a nucleotide sequence comprising SEQ ID NO: 1, 2, 3, 4, 5, 6, 7, 8, 9, 10, 11, 12, 13, 14, 15, 16, 17, 18, 19, 20, 74, 75, or 76;
(b) a polynucleotide comprising a nucleotide sequence having at least 85% sequence identity to SEQ ID NO: 1, 2, 3, 4, 5, 6, 7, 8, 9, 10, 11, 12, 13, 14, 15, 16, 17, 18, 19, 20, 74, 75, or 76, wherein said polynucleotide has regulatory activity in a plant;

(c) a polynucleotide comprising a fragment comprising at least 300 consecutive nucleotides of SEQ ID NO: 1, 2, 3, 4, 5, 6, 7, 8, 9, 10, 11, 12, 13, 14, 15, 16, 17, 18, 19, 20, 74, 75, or 76, wherein said polynucleotide has transcriptional regulatory activity in a plant; or (d) a polynucleotide comprising a nucleotide sequence having at least 85% sequence identity to a fragment comprising at least 300 consecutive nucleotides of SEQ ID NO: 1, 2, 3, 4, 5, 6, 7, 8, 9, 10, 11, 12, 13, 14, 15, 16, 17, 18, 19, 20, 74, 75, or 76.

34. An expression cassette comprising a promoter operably linked to a polynucleotide of interest, wherein said promoter comprises the polynucleotide of embodiment 33.

35. The expression cassette of embodiment 34 wherein said polynucleotide of interest encodes a polypeptide or a suppression element.

36. The expression cassette of embodiment 36, wherein said polynucleotide of interest encodes an HPPD polypeptide having HPPD activity and having insensitivity to an HPPD inhibitor.

37. An expression vector comprising the expression cassette of any one of embodiments 34-36.

38. A plant having stably incorporated into its genome at least one expression cassette comprising a polynucleotide of interest operably linked to a promoter, wherein said promoter comprises the polynucleotide of embodiment 33 or the expression cassette of any one of embodiments 34-36.

39. The plant of embodiment 38, wherein said plant is a dicot.

40. The plant of embodiment 39, wherein said dicot is soybean.

41. The plant of embodiment 39, wherein said dicot is *Brassica*, sunflower, cotton, or alfalfa.

42. The plant of embodiment 38, wherein said plant is a monocot.

43. The plant of embodiment 42, wherein said monocot is maize, wheat, rice, barley, sorghum, or rye.

44. A method of expressing a polynucleotide of interest, said method comprising stably incorporating in the genome of a plant or plant cell the polynucleotide of interest operably linked to a promoter, wherein said promoter comprises the polynucleotide of embodiment 33 or stably incorporating into the genome of the plant or plant cell the expression cassette of any one of embodiments 34-36.

45. The method of embodiment 44, wherein said plant is a dicot.

46. The method of embodiment 45, wherein said dicot is soybean.

47. The method of embodiment 45, wherein said dicot is *Brassica*, sunflower, cotton, or alfalfa.

48. The method of embodiment 44, wherein said plant is a monocot.

49. The method of embodiment 48, wherein said monocot is maize, wheat, rice, barley, sorghum, or rye.

EXPERIMENTAL

Example 1

Isolation of a Chromosomal Region Comprising *Glycine max* HPPD Promoter

An EST (sgc5c.pk001.j9) coding for soybean HPPD was identified from DuPont/Pioneer's proprietary *Glycine max* EST database using conventional bioinformatic tools including BLAST as described in U.S. Pat. No. 7,226,745. The soybean HPPD coding region sequence (U.S. Pat. No. 7,226,745 SEQ ID NO: 35 and 36) was cloned into a T7-based bacterial expression vector. Expression, purification and characterization of the *G. max* HPPD protein proved that the encoded protein is a functional HPPD, able to catalyze the reaction from 4-hydroxyphenylpyruvate to homogentisate. Using this soybean HPPD coding sequence as query, Pioneer Unigene PSO409914 was identified. Search of the genome assembly database with the unigene as query resulted in approximately 2 kb virtual genomic sequence upstream of the EST. To validate the virtual genomic sequence, polymerase chain reaction (PCR) primers (Forward primer: GCAAGTATTTCAATACAATAGC (SEQ ID NO:42) and Reverse primer: GTTATCTGATATGATGTTGC (SEQ ID NO: 43)) were designed and used to amplify the HPPD locus from genomic DNA isolated from an elite soybean variety and the common Jack variety. Genomic DNA isolation protocols including those from Qiagen for plant DNA were followed. PCR reaction parameters were: Cycle1: 94 C, 2 min; Cycle 2 to 30: 94 C, 30 s; 65 C, 1 min; 72 C, 5 min; Cycle 31: 72 C, 10 min. A proof-reading DNA polymerase, pfu Turbo from Stratagene was used for PCR amplification. A 4306 bp fragment and a 4310 bp fragment were obtained from elite and Jack, respectively. These fragments were cloned into Zero blunt TOPO PCR cloning vectors (Invitrogen) and fully sequenced. The sequence comprises 3' sequences, HPPD coding region, and upstream genomic sequence. The locus is highly conserved in both soy varieties, with an overall of 99% sequence identity at the nucleotide level. A 462 bp intron and a 459 bp intron in the HPPD coding region were identified in elite and Jack, respectively. SEQ ID NO: 1 is the 2166 bp upstream genomic sequence of elite *G. max* comprising the HPPD promoter sequence.

Example 2

Characterization of the Genomic Sequence Upstream of *G. max* HPPD Coding Region The 1228 bp genomic sequence at the 3' end of SEQ ID NO:1 was subjected to promoter analysis using Pioneer's proprietary promoter analysis software, Promoter REAPer and Promoter Delineator (US2010/0138952A1). Genomic sequence from other species including *Arabidopsis thaliana*, (SEQ ID NO: 64), *Medicago truncatula* (SEQ ID NO: 65), Poplar (SEQ ID NO: 66), *Brassica rapa* (SEQ ID NO: 67), *Vitis vinifera* (SEQ ID NO: 68), and the monocot *Sorghum bicolor* (SEQ ID NO: 69) were included for comparison in this analysis. With the program Promoter REAPer, regions were identified in soy HPPD promoter that are predicted to be important for its activity based on the sequence conservation of a set of DNA motifs across seven plant species. A total of eleven regions, each 7 to 13 bp long and located no further than 880 bp from the translation start codon were predicted to have a high level of importance (see FIG. 1). About ten other 7 bp regions show a medium level of importance. Five putative TATA boxes, GTATAAATAA (TATA 1; SEQ ID NO: 44), CCAATATATG (TATA2; SEQ ID NO:45), CCTTATATATC (TATA3; SEQ ID NO:46), TATATAATAA (TATA4; SEQ ID NO: 47), and GAATATAAG (TATA5; SEQ ID NO:48) were identified. TATA3 (closest to the coding region) was predicted to be the primary TATA box for HPPD promoter activity. The encoded protein, starting from the first ATG after TATA3 (SEQ ID NO: 46), would have four more amino acid sequence (MPIP) compared with the annotated *G. max* HPPD protein sequence in Genbank EF608178. Using Promoter Delineator, the transcription start site (TSS) "A" was predicted and designated as +1.

RNA ligation mediated (RLM) 5' rapid cloning of cDNA ends (5' RACE) revealed alternate transcription start sites for the native Gm HPPD promoter. Using total RNA extracted from young soy leaves and the First Choice RLM-RACE kit (Ambion) per manufacturer's protocol, two major amplification products were observed, indicating two TSS. Cloning and sequencing of these PCR products revealed one transcript beginning with the sequence GTAATAAAAAAA-GAGAGAAGCCGCATCAA (SEQ ID NO: 49) at position −231 relative to the predicted TSS. A second transcript began with the sequence AAGCAGCAGCATCACACCACAC-CAATGCC (SEQ ID NO: 50) at position +7 relative to the predicted TSS. Sequence of multiple clones for each 5' RACE product indicated an approximately 4 nucleotide variation between individual transcripts for both sites.

Open reading frame (ORF) analysis of the TSS-231 mRNA indicates a short ORF (upORF) encoding 7 AAs starting at position −189. Downstream of this, another ORF begins at position −93 and continues in frame through the catalytic portion of the HPPD protein; the protein from this ORF begins with MPMY. The TSS+7 mRNA contains a single ORF, in the same reading frame as the protein encoded by the TSS−231 mRNA, but beginning 41 amino acids (123 nucleotides) downstream; the protein encoded by this ORF begins with MPIP.

Figure 2:
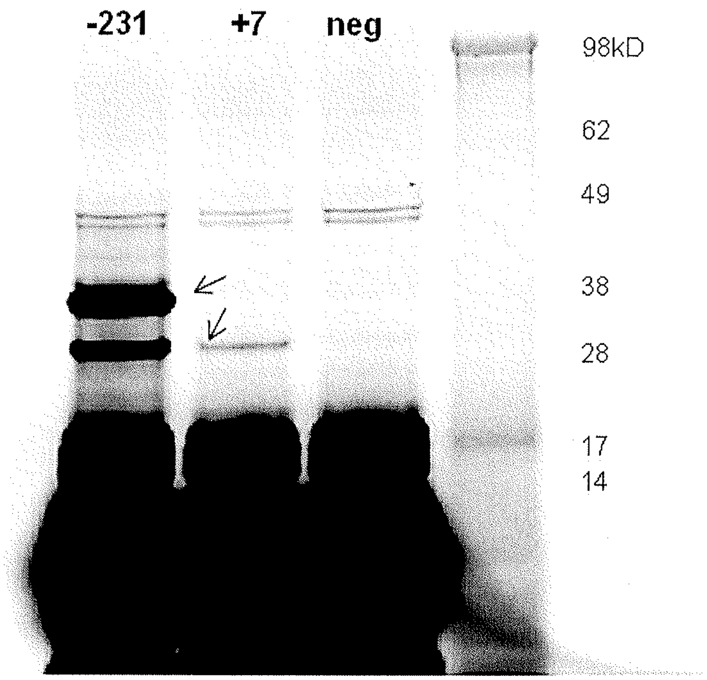
FIG. 2 shows a protein gel of in vitro translation products of the two *G. max* HPPD transcripts, deomonstrating that the predicted polypeptide products from the upstream and downstream in-frame ATG start codons are both made. Linked transcription-translation was performed in wheat germ extracts using 3' truncated Gm HPPD transcription vectors. Predicted protein mass from −231 mRNA: 30.6 kD; +7 mRNA: 26.0 kD.

Linked in vitro transcription and translation indicates both mRNAs are translated (see FIG. 2). The +7 transcript is translated to produce a single protein, designated the "short" protein. The −231 transcript yields two proteins, with the lower molecular weight band at the same MW as the single protein produced from the +7 transcript. The higher MW protein produced from the −231 transcript is designated the "long" protein.

Example 3

Synthetic Promoter Analysis by *Agrobacterium*-Mediated Transient Expression in Plants This example describes qualitative and quantitative assigned ranking of HPPD promoter variants using *Agrobacterium* infection and subsequent transient expression of the red fluorescence marker DsRed2 (Clonetech, Mountain View, Calif.). Agro-infiltration is a well described method (Kapila et. al. (1997) *Plant Science* 122: 101-108) of introducing an *Agrobacterium* cell suspension to plant cells of intact tissues so that reproducible infection and subsequent plant derived transgene expression may be measured or studied.

Leaf tissues of bush bean (common bean, *Phaseolus vulgaris*), were agro-infiltrated with normalized bacterial cell cultures of test and control strains. Up to 30 leaf discs infected with the same culture were pooled for analysis. Each pool of infiltrated leaf samples represented (about 260 mg fresh weight) tissue equally derived from 15 plants of uniform developmental stage.

Qualitative assessment of promoter strength was determined 4-5 days post-infection by visually inspecting treated samples under a stereo fluorescent microscope (Leica Microsystems—Wetzlar, Germany; M165 FC with DsRed Filter set; no. 10447412), and acquiring images (Leica Microsystems—Wetzlar, Germany; DFC300 FX R2) of representative examples at fixed exposure time of 7 seconds. Analysis of promoter strength in samples was determined 5 days post infection by protein extraction and quantitative measure of (red) fluorescence using a Typhoon Trio+ Variable Mode Imager configured appropriately for DsRed detection; 532 nm Excitation laser and 580 nm BP30 Emission filter, PMT=375-400V, 100 um pixel size resolution, and Image Quant TL image analysis software (GE Healthcare—Life Sciences, Piscataway, N.J.). Prior to scanning, homogenized plant extracts were prepared in 500 ul extraction buffer (100 mM potassium phosphate pH7.8, 1 mM EDTA, 7 mM beta-mercaptoethanol, 1% Triton X100, 10% glycerol), in 2 ml micro-centrifuge tubes using a Geno-Grinder 2000 (Spex CertiPrep, Metuchen, N.J.). 250 ul of supernatant was collected and filtered through a Milipore MultiScreen-HV (Millipore—Billerica, Mass.; cat no. MAHVN4550) multi-well filter-plate and then normalized to 50 ug total extracted protein, as determined by Bradford protein assay (Bio-Rad—Hercules, Calif.; Quick Start™ Bradford Protein Assay). 100 ul of normalized extract of samples was scanned in 96-well plates. Purified recombinant DsRed2 standard protein (Clonetech Cat. No. 632436) was scanned simultaneously to treated sample extracts and the data was represented as calculated ng concentration DsRed2, per 50 ug sample.

Example 4

Mutagenesis Analysis of the HPPD Promoter

A 2061 bp fragment corresponding to nucleotides 103-2163 of SEQ ID NO:1 was created by PCR with primers (Forward primer hp0234: GTTTTCCGCGGGTGTTGATCC (SEQ ID NO: 51) and Reverse primer hp2296: TCATTGG-TACCTGGTGTGGTGTGATGCTGC (SEQ ID NO: 52)) to introduce SacII and KpnI sites. This fragment was isolated via gel-purification, digested with restriction enzymes SacII and KpnI, and ligated with a DsRed2 marker gene (ClonTech) together with the transcription terminator sequence PIN II from potato, to form an expression unit.

Figure 3:
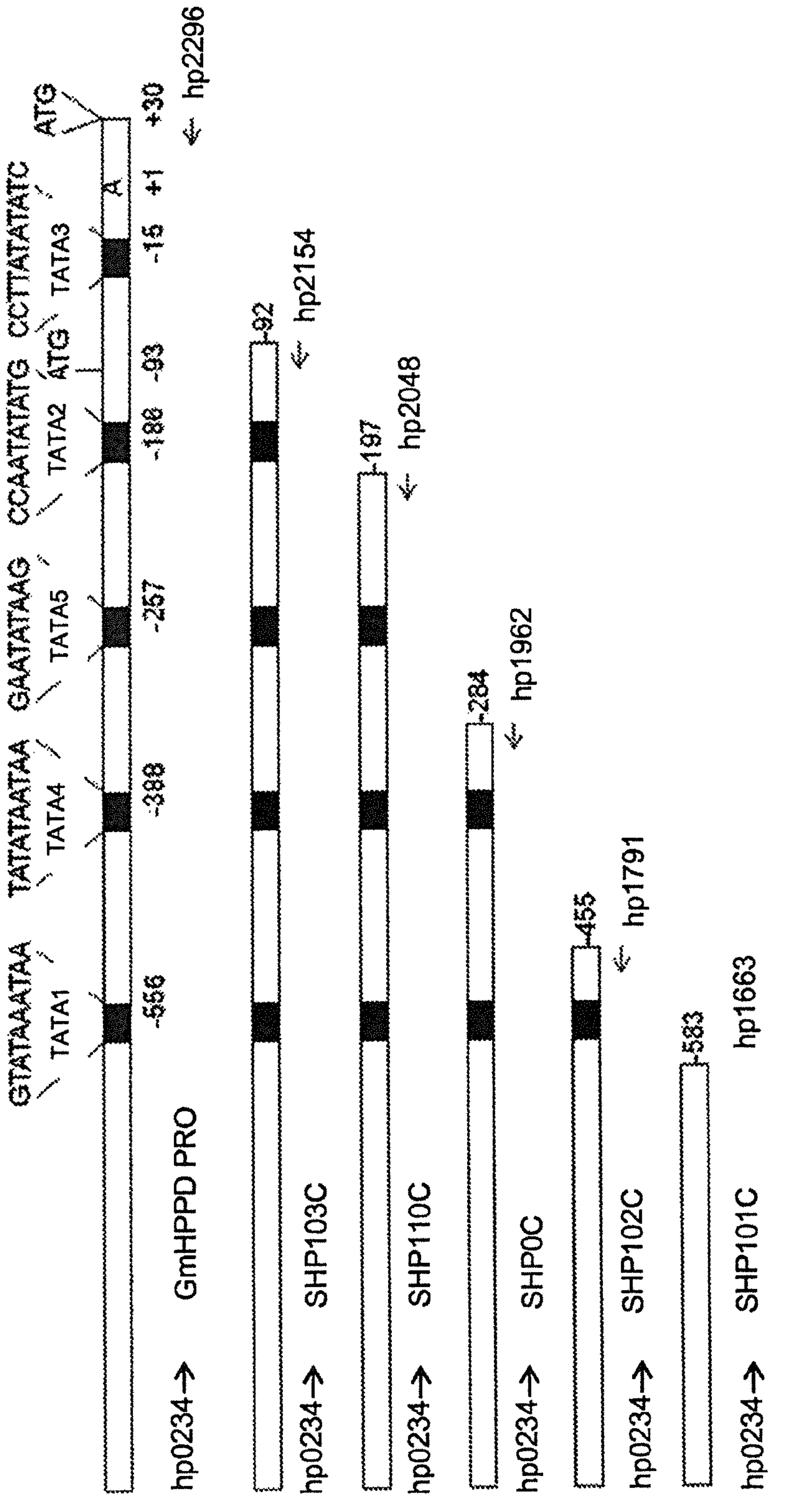
FIG. 3 provides a depiction of nested deletion mutants in the *G. max* HPPD promoter region. TATA1 (GTATAAATAA; SEQ ID NO: 44), TATA2 (CCAATATATG; SEQ ID NO: 45), TATA3 (CCTTATATATC; SEQ ID NO: 46), TATA4 (TATATAATAA; SEQ ID NO: 47), and TATA5 (GAATATAAG; SEQ ID NO: 48) are indicated by shaded regions.

To evaluate the predicted TATA boxes in promoter activity, nested deletion mutants of GmHPPD PRO (SEQ ID NO: 1) were created using PCR with primers (Forward primer hp0234: GTTTTCCGCGGGTGTTGATCC (SEQ ID NO: 51) and Reverse primers hp2154: AGCATGGTACCT-TGCGTCTGGGTTGAG (SEQ ID NO: 53), hp2048: ATCTGGTACCTGATGTTGATGCGGC (SEQ ID NO: 62) hp1962: AGGAGGTACCGTCAAATCCACCTAG (SEQ ID NO: 54), hp1791: AGCCTGGTACCTTGTGTG-TAAAAAAGATAAGAC (SEQ ID NO: 63), and hp1663: TCCTTGGTACCTGATGCACTATATAACG (SEQ ID NO: 55)) as depicted in FIG. 3. Resultant deletion mutant promoter fragments SHPOC (SEQ ID NO: 20), SHP101C (SEQ ID NO 2), SHP102C (SEQ ID NO 3), SHP103C (SEQ ID 4), and SHP110C (SEQ ID 11), were fused with DsRed2 to create various expression cassettes for expression activity analysis in infiltrated leaf tissues.

Figure 4:
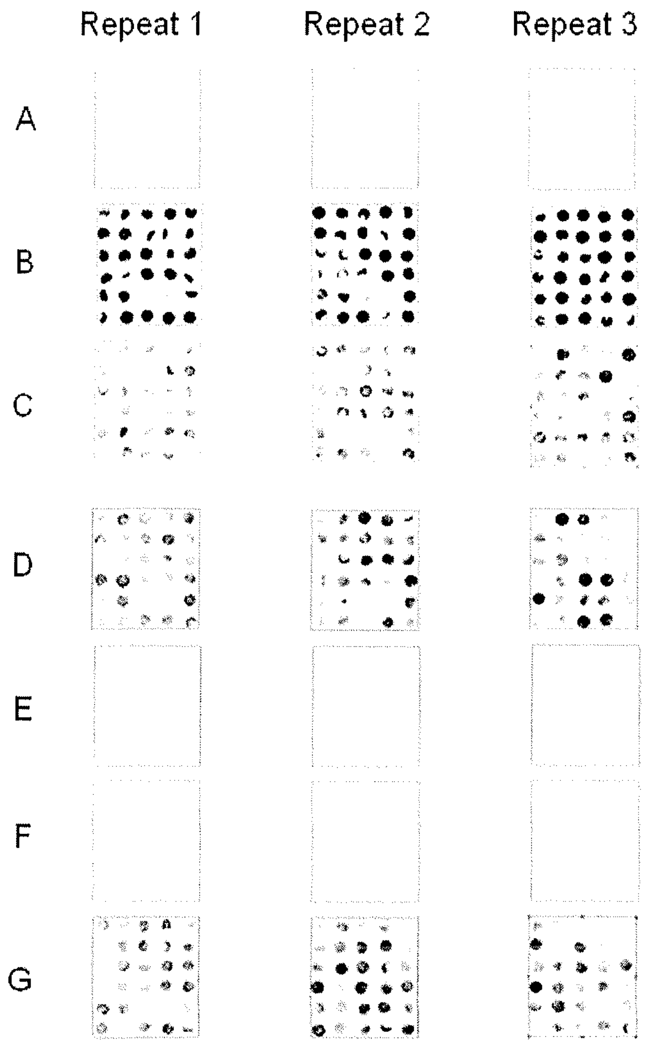
FIG. 4 shows fluorescence images from Agro-infiltrated leaf discs were captured as described in Example 3. Each plate contains 30 randomly picked leaf discs. A. dMMV (Dey and Matai, (1999) *Transgenics* 3:61-70) promoter driven GUS (negative control); B. dMMV promoter driven DsRed2; C. H2B promoter (U.S. Pat. No. 6,177,611) driven DsRed2; D. Native HPPD promoter driven DsRed2; E. SHP101C (deletion of all 5 TATA boxes) driven DsRed2; F. SHP102C (Deletion of TATA 2, 3, 4, and 5) driven DsRed2; G. SHP103C (deletion of TATA3) driven DsRed2.

These expression cassettes were introduced into a plant transformation binary vector via Gateway cloning (Invitrogen) and then introduced into *Agrobacterum* strain AGL1 via electroporation according to Shen and Forde (1989, *Nucleic Acids Res.* 17: 8385). As described in Example 3, the resultant *Agrobacterium* strains were infiltrated into bush bean leaf tissues. Infiltrated leaf discs were visually examined under a flourorescent microscope and scanned with Typhoon Trio+ Variable Mode Imager for red fluorescence produced from DsRED2 protein accumulation. FIG. 4 shows an example of the image obtained from Typhoon scanning. Infiltration analysis confirmed that the GmHPPD PRO DNA fragment was able to drive the expression of DsRed2 in infiltrated leaf tissues compared with fluorescent background from leaf tissues infiltrated with a dMMV (Dey and Matai, (1999) Transgenics 3:61-70) GUS construct (FIGS. 4. A and D).

As shown in FIG. 4, deletion of 613 bp DNA fragment, including all 5 putative TATA boxes, from the predicted transcription start site in SEQ ID: 1 resulted in a DNA fragment SHP101C that was not able to drive DsRed2 expression to a level above the background red fluorescence produced in leaf tissues infiltrated with a dMMV-GUS construct (A and E, FIG. 4). GUS protein is well known to not fluoresce under these detection conditions set for DsRed2. Nested deletion fragments SHP110C, SHP0C, and SHP102C (FIG. 3) containing deletion of TATA2 and 3, TATA2, 3, and 5, or TATA2, 3, 4, and 5, respectively, did not show promoter activity (Table 3). The next nested deletion mutant fragment SHP103C (FIG. 3) brings TATA2 back so that only TATA3 is deleted. This fragment was able to drive Ds-Red expression to a level similar to that of the native HPPD promoter (FIGS. 4, D and G), suggesting that TATA2 functions as the primary TATA element for the native HPPD promoter. Because the long transcript starts before TATA2, TATA5 and/or TATA4 are likely important elements in the promoter, operating together with TATA2 to drive the transcription of −231 mRNA. As shown in Example 2, this transcript could produce two HPPD variants, one starts translation at +31 and the other at −93. The resultant short HPPD variant starts with MPIP and the long variant starts with MPMY with 41 amino acids added to the N-term of the previously annotated soybean HPPD protein (SEQ ID 61). TATA3, positioned 160 bp downstream of TATA2, would encode part of the protein (see Example 2 for more details).

In addition to visual observations, relative promoter strength was determined by quantitative measurement of the red fluorescence generated from expressed DsRed2 protein in infiltrated leaf tissues. Briefly, 50 ug of total extracted protein from infiltrated leaf discs was scanned using a Typhoon Trio+ Variable Mode Imager as described in Example 3. Red fluorescence in the protein sample was quantitatively measured. Infiltration experiments for each construct were repeated at least three times. For each repeat experiment, the background red fluorescence detected in control leaf tissues infiltrated with a non-DsRED expressing construct, dMMV-GUS or promoterless DsRED, was subtracted for data normalization.

The DsRED2 readouts were used to calculate the level of DsRed2 from each construct relative to the DsRed2 expressed from the GmHPPD PRO construct (the entire 2061 promoter fragment), which was set to 100%. Table 2 shows the calculation of relative promoter strength for SHP101C, SHP102C, and SHP103C. Average relative promoter strength for all mutant promoter constructs was obtained with data from 3 or more repeat infiltration experiments and listed in Table 3. With 0% relative promoter strength, deletions in SHP101C and SHP102C eliminated the activity of the HPPD promoter, indicating that the upstream sequence through TATA 1 has no promoter activity in the transient expression in bushbean experiments. With 2-3% relative promoter strength, deletion mutants SHP0C and SHP110C led to very low but detectable expression of DsRED2, suggesting that the upstream sequence through TATA4 and TATA5 could serve as a weak promoter. Deletion mutant SHP103C in which only TATA3 is deleted retained 90% of the native HPPD promoter activity, suggesting that the upstream sequence through TATA2 is a fully functional promoter sequence.

TABLE 2

| | | Test 1 | | | Test 2 | | | Test 3 | | | Average | |
|---|---|---|---|---|---|---|---|---|---|---|---|---|
| Promoter Variant | Description | DsRED reading (PMT = 375) | Background subtraction | Relative pro strength (%) | DsRED reading (PMT = 400) | Background subtraction | Relative pro strength (%) | DsRED reading (PMT = 400) | Background subtraction | Relative pro strength (%) | relative pro strength (%) | Standard deviation |
| dMMV | dMMV-GUS (negative control) | 16,829 | 0 | 0 | 24,943 | 0 | 0 | 47000 | 0 | 0 | 0 | 0.0 |
| H2B | H2B-DsRED2 (positive control) | 447,374 | 430,545 | 65 | 2,540,112 | 2,515,169 | 104 | 2700000 | 2,653,000 | 99 | 89 | 21.1 |
| GmHPPD PRO | Native *Glycine max* HPPD promoter region | 676,198 | 659,369 | 100 | 2,439,513 | 2,414,570 | 100 | 2730000 | 2,683,000 | 100 | 100 | 0.0 |
| SHP101C | Deletion of all 5 TATA | 18,294 | 1,465 | 0 | 22,788 | −2,155 | 0 | 61000 | 14,000 | 1 | 0 | 0.3 |
| SHP102C | Deletion of TATA 2, 3, 4, and 5 | 13,977 | −2,852 | 0 | 23,684 | −1,259 | 0 | 69000 | 22,000 | 1 | 0 | 0.6 |
| SHP103C | Deletion of TATA3 | 613,261 | 596,432 | 90 | 1,996,294 | 1,971,351 | 82 | 2334000 | 2,287,000 | 85 | 86 | 4.4 |

Example 5

Site-Directed Mutagenesis Study of the HPPD Promoter

Using site-directed mutagenesis (SDM), mutations in the putative TATA boxes were created to generate another set of promoters (SHP104C to 109C and 111C to 118C) with varied strength. Site-directed mutagenesis protocols can be found in Stratagene's Quick Change manual. In SEQ ID NO: 5, a single A to C transversion in TATA3 of SEQ ID NO: 1 at position −20 relative to the putative transcription start site was created. In SEQ ID NO: 6, a T to C transition in TATA1 at position −563 relative to putative transcription start site was generated in addition to the A to C transversion at −20. In SEQ ID NO: 7, a third point mutation was added to SEQ ID NO: 6 at position −190 relative to the putative transcription start site (T to G transversion). These new promoter sequences, as SacII-KpnI fragments, were fused to DsRed2 to form expression units and analyzed for promoter activity as described in examples 3 and 4. As summarized in Table 3, with a point mutation in TATA3, the promoter activity of the resultant DNA fragment was reduced to 23% of the native HPPD promoter. In all cases if TATA3 is mutated, no matter what other mutations are present in the other TATA boxes, promoter activity is low but clearly detectable. This result provides evidence that TATA3 is important in maintaining full activity of the soy HPPD promoter but that other elements are also functional. Additional site-directed mutagenesis with two to three nucleotide changes in similar positions in the three putative TATA boxes 1, 2, and 3 was performed to generate another set of promoters. In SHP107C (SEQ ID NO: 8), a three nucleotide change was made in TATA3 (TAT to GCA) at position −21 relative to the putative transcription start site. In SHP108C (SEQ ID NO: 9), another set of three nucleotide changes (ATA to CCG) in TATA1 at position −564 was made in addition to the TAT to GCA change in TATA3. In SHP109C (SEQ ID NO: 10), in addition to the nucleotide changes in TATA1 and TATA3 as in SHP108C, three nucleotide changes (TAT to CAG) in TATA2 at position −192 were made. These promoter variants directed DsRed2 expression at a level slightly lower than the respective single point mutation variants (SHP104C, 105C, and 106C). Additional three nucleotide changes in TATA4 or 5 of fragments SHP107C and SHP109C were made. The resultant mutant fragments SHP114C, SHP116C, SHP117C, and SHP118C all resulted in DsRed2 expression at a further reduced level (Table 3). For example, SHP109C in which three nucleotide mutations were made in TATA1, 2, and 3 has 19% of native HPPD promoter activity. Adding three-nucleotide changes in TATA4 and 5 resulted in a variant SHP118C in which all five putative TATA boxes were mutated. SHP118C has only 9% of native HPPD promoter activity. This result shows that cryptic or unknown sites in the promoter region of SEQ ID NO: 1 may be involved in promoter function.

The next set of promoter variants was created with three nucleotide changes in other TATA boxes except for TATA3. Three nucleotide changes in TATA2 (TAT to CAG) at position −192 (SHP111C, SEQ ID NO: 12) allowed retention of 93% of the native HPPD promoter activity (Table 3). In fact, as long as TATA3 remain unchanged, SDM mutants in TATA2 or 4 or 5 or combinations, such as in the example of SHP115C, are all similar, having approximately 90% of native HPPD promoter activity (SEQ ID NO: 12, 13, 14, and 16, Table 3).

Taken together, these results suggest that the native HPPD promoter may have duplicate TATA elements in TATA2 and TATA3. TATA3 is essential for the full promoter activity to drive expression of HPPD protein. When TATA3 remains unchanged, mutations in other TATA boxes did not significantly alter the strength of native HPPD promoter. When TATA3 is mutated, either by point mutation or three nucleotide changes, plus or minus additional mutations in other putative TATA boxes (1, 2, 4, and 5), promoter activity of the resultant promoter variants is reduced to 9-30% of that of the native HPPD promoter. TATA4 and 5 may help with promoter activity that utilizes TATA3. TATA2 could be an important element for the upstream promoter (comparing SHP110C and SHP103C). When TATA3 is deleted, the promoter fragment still retained 93% of promoter activity, strongly suggest that the putative long transcript with 2 ATGs, one at −93 and the other −87, in-frame with HPPD protein, could be produced. Example 2 provides experimental proof that two transcripts of different lengths are indeed produced from the native HPPD promoter. TATA4, TATA5, or some other element must be functioning for the polymerase recognition for the generation of the long transcript.

TABLE 3

Comparison of promoter activity among variants of the native *G. max* HPPD promoter

| SEQ ID | Promoter Variant | Description | Average Relative Promoter Strength (%) from extract |
|---|---|---|---|
| 1 | GmHPPD PRO | Native *Glycine max* HPPD promoter region | 100 |
| 20 | SHP0C | Deletion of TATA2, TATA3, and TATA5 | 2 |
| 2 | SHP101C | Deletion of all 5 TATA | 0 |
| 3 | SHP102C | Deletion of TATA 2, 3, 4, and 5 | 0 |
| 4 | SHP103C | Deletion of TATA3 | 90 |
| 5 | SHP104C | A to C mutation in TATA3 | 23 |
| 6 | SHP105C | T to C in TATA1 and A to C in TATA3 | 30 |
| 7 | SHP106C | T to C in TATA1, T to G in TATA2, and A to C in TATA3 | 21 |
| 8 | SHP107C | TAT to GCA mutation in TATA3 | 15 |
| 9 | SHP108C | ATA to CCG in TATA1 and TAT to GCA in TATA3 | 19 |
| 10 | SHP109C | ATA to CCG in TATA1, TAT to CAG in TATA2, and TAT to GCA in TATA3 | 19 |
| 11 | SHP110C | Deletion of TATA2 and TATA3 | 3 |
| 12 | SHP111C | TAT to CAG mutation in TATA2 | 93 |
| 13 | SHP112C | TAT to CAG mutation in TATA4 | 97 |
| 14 | SHP113C | TAT to CAG mutation in TATA5 | 89 |
| 15 | SHP114C | TAT to CAG in TATA5, TAT to GCA in TATA3 | 11 |
| 16 | SHP115C | TAT to CAG in TATA5, TAT to CAG in TATA2 | 90 |
| 17 | SHP116C | ATA to CCG in TATA1, TAT to CAG in TATA2, TAT to GCA in TATA3, TAT to CAG in TATA5 | 12 |
| 18 | SHP117C | TAT to CAG mutation in TATA4, TAT to GCA mutation in TATA3 | 9 |
| 19 | SHP118C | ATA to CCG in TATA1, TAT to CAG in TATA2, TAT to GCA in TATA3, TAT to CAG in TATA4, TAT to CAG in TATA5 | 9 |

TABLE 3-continued

Comparison of promoter activity among variants of the native *G. max* HPPD promoter

| SEQ ID | Promoter Variant | Description | Average Relative Promoter Strength (%) from extract |
|---|---|---|---|
| 74 | 120C | Point mutation to eliminate upORF start codon | 105 |
| 75 | 121C | Point mutation to insert stop codon just upstream of downstream TSS | 92 |

Example 6

Construction of Synthetic Promoters and Their Activity

SHP101C and SHP102C lack promoter activity due to deletion of TATA binding sites. To create synthetic promoters using these non-promoter DNA fragments, synthetic element I (SED ID NO: 21) and II (SEQ ID NO: 22), each flanked by restriction sites XhoI and KpnI, were synthesized and ligated with the 3' ends of the HPPD promoter-derived DNA fragments. Synthetic element I comprises the SynII core (derived from U.S. Pat. No. 6,072,050 SEQ ID NO: 1) sequences followed by the 45 bp putative 5'UTR sequence including the predicted transcription start site from the soybean native HPPD gene (ACAACCACCAAGCTCAATCTCAAGCAG-CAGCATCACACCACACCA, (SEQ ID NO: 56) nucleotides between TATA3 and ATG, see FIG. 1). Synthetic element II contains the Rsyn7 region derived from U.S. Pat. No. 6,072,050 SEQ ID NO: 2 immediately upstream of synthetic element I (SEQ ID NO:21). These synthetic promoters were then fused with DsRed2 to evaluate their ability to drive DsRed2 expression in infiltrated leaf tissues. Table 4 contains results from various synthetic promoters and their relative promoter strength determined by DsRed2 expression as outlined in Example 3. As shown in Table 4, the addition of synthetic element II (SEQ ID NO: 22) to the non-promoter DNA fragments SHP101C and 102C restored promoter activity to 13% and 23% of that of the native HPPD promoter. Replacing synthetic element II (SEQ ID NO: 22) in these two SHP promoters with synthetic element I (SEQ ID NO: 21) resulted in low activity promoters.

With synthetic element I, synthetic promoters SHP103, SHP104, SHP105, SHP106, SHP107, SHP108, and SHP109 were created. SHP203, 204, 205, 206, 207, 208, and 209 were created with synthetic element II. These synthetic promoters were all more active than SHP101/102 and SHP201/202, with approximately one to four fold higher promoter activity when compared to that of the native HPPD promoter (Table 4).

Example 7

Use of SHP Promoters to Achieve Appropriate Transgene Expression

The rare representation of HPPD ESTs in leaf tissue in the soybean database suggests that soy HPPD is transcribed at an extremely low level and as inferred from tissue distribution may be expressed in a tissue-specific and/or developmental-stage specific manner. Cis-control elements embedded in the promoter region can be used in a chimeric promoter to drive expression of a transgene mimicking the expression pattern of the native HPPD. Examples of such transgenes include marker genes such as DsRed2 and GUS, genes in tyrosine metabolic pathway such as HPPD, PDH, and ADH, and genes involved in other metabolic pathways. In one example, to visualize native HPPD expression patterns, DsRed2 or GUS was fused with synthetic promoters such as SHP103 (SEQ ID NO: 25) or the native promoter (SEQ ID NO: 1) and delivered into *Arabidopsis* via floral-dip, a well-known *Agrobacterium*-mediated transformation procedure (Clough and Bent, Plant J. 1998. 16(6):735-43). Transgenic seeds, selected by kanamycin resistance, were germinated and plants were examined for the expression pattern of DsRed2. Similar constructs are also delivered into tobacco via *Agrobacterium*-mediated transformation and expression of the marker gene is analyzed by Northern, Western, and fluorescence scanning. In this way, sequences important for the tissue and temporal specific properties of the soy HPPD promoter can be explored.

The above mentioned synthetic promoters can also be used to drive HPPD transgene expression in *G. max* to enable successful engineering of an HPPD-inhibitor tolerance trait in plants. To mimic the level and pattern of native HPPD expression in soy, the maize wild-type HPPD and insensitive variants such as those disclosed in U.S. Provisional Patent Application 61/401,456, filed Aug. 13, 2010 were constructed with various SHP promoters and delivered into *G. max* via particle bombardment.

In one example, the insensitive maize HPPD variants were constructed with SHP promoters such that the 5' end of the long transcript is fused with the coding sequence, with or without N terminal truncation, of the insensitive variants to create a translational fusion between the soy HPPD coding sequence and the maize insensitive variants. Under the direction of SHP promoters, two transcripts are produced in the transgenic soybean plants in similar time and spatial pattern to the native HPPD transcripts but with higher expression level in one or both mRNA species. The resultant fusion proteins, one with an additional 41 amino acids at the N-terminus, are distributed in subcellular locations in a similar way to that of the native HPPD protein. Such transgenic plants are produced via particle bombardment-mediated transformation or *Agrobacterium*-mediated transformation. T0 plants are sprayed with 2×HPPD-inhibiting herbicides to test for gene efficacy and the next generations of plants are evaluated either in the greenhouse or in the field for agronomic evaluations. Transcription efficiency and pattern are examined using RT-PCR, northern, and primer extension analysis. Protein expression level and pattern are determined by western, Mass Spectrometry, and immuno-localization.

Example 8

Modifications in Synthetic Promoters to Alter Promoter Activity

The level or pattern of transgene expression conferred by designed HPPD promoters described above can be changed with further modifications in the sequence. In general, addition of enhancer elements increases promoter activity. For example, when a 2×35S enhancer element was added to SHP101 and SHP103 (SEQ ID NOS: 23 and 25, respectively), greater than 10 fold higher promoter activity was observed. Alternatively, changes made to the 5'UTR sequence in SHP promoters can alter promoter activity. Furthermore, insertion of SynII core or SynII core plus Rsyn7 or other TATA elements into upstream sequence of mutant promoter fragments described in Example 4 and 5 can also alter promoter activity. In SHP110 (SEQ ID NO: 41), partial SynII core sequence is inserted in place of TATA5. The transcription of the long mRNA is enhanced in SHP110. In SHP210 (SEQ ID NO:78) TATA5 through transcription start site at −231 is deleted (deletion=nt 1867-1905 of SEQ ID 1) and replaced with Rsyn7+ the partial SynII core sequence; transcription from the −231 TSS is expected to be further elevated compared to SHP110. In SHP111 (SEQ ID NO:77) TATA3 through transcription start site at +7 is deleted (deletion=nt 2106-2140 of SEQ ID 1) and replaced with the partial SynII Core; transcription from the +7 TSS is expected to be elevated relative to the native promoter. In SHP120C (SEQ ID NO:74) an A to T mutation at nt 1945 of SEQ ID 1 eliminates the start codon of the upORF element and may be expected to upregulate translation of mRNA from the −231 transcription start site. Other modifications include the addition of an intron in the 5'UTR. Further trimming at the 5' end of the SHP sequences can be made to further modulate promoter activity.

TABLE 4

Relative strength of SHP promoters

| SEQ ID | Promoter name | Base DNA Fragment | Added Sequence (SEQ ID) | Relative Strength (% Native HPPD Promoter) |
|---|---|---|---|---|
| 1 | GmHPPD PRO | GmHPPD PRO | NA | 100 |
| 23 | SHP101 | SHP101C | 21 | 3 |
| 24 | SHP102 | SHP102C | 21 | 4 |
| 25 | SHP103 | SHP103C | 21 | 310 |
| 26 | SHP104 | SHP104C | 21 | 181 |
| 27 | SHP105 | SHP105C | 21 | 210 |
| 28 | SHP106 | SHP106C | 21 | 377 |
| 29 | SHP107 | SHP107C | 21 | 129 |
| 30 | SHP108 | SHP108C | 21 | 150 |
| 31 | SHP109 | SHP109C | 21 | 266 |
| 32 | SHP201 | SHP101C | 22 | 23 |
| 33 | SHP202 | SHP102C | 22 | 13 |
| 34 | SHP203 | SHP103C | 22 | 272 |
| 35 | SHP204 | SHP104C | 22 | 277 |
| 36 | SHP205 | SHP105C | 22 | 152 |
| 37 | SHP206 | SHP106C | 22 | 195 |
| 38 | SHP207 | SHP107C | 22 | 231 |
| 39 | SHP208 | SHP108C | 22 | 213 |
| 40 | SHP209 | SHP109C | 22 | 230 |
| 41 | SHP110 | NA | 70 | 78 |

Example 9

Transient Expression of Gm HPPD-AcGFP Fusion Proteins

Numerous genes have been found to have two or more in-frame ATGs at the 5' end (For review, see Small et al., *Plant Molecular Biology,* 1998. 38: 265-277). Many of such genes are known to have multiple transcription starts to enable the production of two proteins from the same gene. Often, the "long" protein contains plastid targeting signal at the N-terminal while the "short" protein does not. Appropriate distribution of the "long" and "short" protein variants between two subcellular compartments is desired for the respective protein function to be carried our normally. The soy HPPD gene described here falls into this class of genes. No other HPPD gene is known to share the same description.

Transient expression experiments indicate that the long HPPD protein (SEQ ID NO: 58) is imported to chloroplasts, while the short protein (SEQ ID NO: 61) remains in the cytosol. Plant expression cassettes were constructed fusing portions of the N-terminus of Gm HPPD to an *Aequorea coerulescens* green fluorescent protein 1 (AcGFP1). One fusion contained amino acid residues 1-86 of the long Gm HPPD protein. Another contained residues 1-44 of the short HPPD protein (this corresponds to residues 42-86 of the long protein). These cassettes were incorporated into binary vectors which also contained an untargeted DsRed2 expression cassette and introduced into *A. tumefaciens* strain AGL1 and then used to infect leaf discs of *G. max* as described in Example 3. As shown in FIG. 10 below, green fluorescence is clearly visible in the chloroplasts of infected cells when AcGFP is fused to amino acid residues 1-86 of Gm HPPD. When the fusion is made with residues 42-86, corresponding to the 44 N-terminus residues of the short protein, green fluorescence is visible only in the cytoplasm.

Example 10

HPPD Promoter Expression Profiling in *Arabidopsis*

This example describes qualitative assessment of spatial and temporal expression pattern for engineered red fluorescence reporter (DsRed2; Clonetech, Mountain View, Calif. USA) driven by variants of the *G. max* HPPD promoter in stably transformed *Arabidopsis* plants.

*Agrobacterium* mediated transformation and selection of ecotype Columbia (Col-0) *Arabidopsis thaliana* was performed according to published protocols by Clough S. J., Bent A. 1998, *Plant J.* 16: 735-743, employing "floral spray" technique of bacterial suspension application to flowering plants, described by Chung M. H., Chen M. K., Pan S. M. 2000, *Transgenic Res.* 9: 471-476.

Harvested seed were sown on sterile agar plates with antibiotic selection and grown at 22° C./125 umol $m^{-2}$ $m^{-1}$/18 hour photoperiod in a growth chamber. Resistant seedlings were identified and transferred to soil (Sunshine Redi-earth Plug & Seedling; Sun Grow Horticulture Inc, Bellvue, Wash. USA) in 3" square pots at 8 days. Some seedlings were transferred to fresh selection medium in 110 mm Petri-dishes for further characterizing early vegetative expression pattern. Potted plants were grown under 22° C./225 umol $m^{-2}$ $m^{-1}$/18 hour photoperiod in growth rooms while Petri dishes were retained under growth chamber conditions.

Inspection and documentation of expression pattern was performed at 15, 24 and 33 days after sowing representing early and late vegetative and early reproductive plant development stages, respectively. Event populations were inspected and imaged under stereo epi-fluorescent microscope (M165 FC; Leica Microsystems—Wetzlar, Germany; with DsRed Filter set; no. 10447412 and DFC300 FX R2 digital camera system), acquiring fluorescence images of representative examples at fixed illumination, magnification and image capture time. Further examination of DsRed expression profiles were determined by Typhoon Trio+ Variable Mode Imager (p/n 63-0055-89; GE Healthcare—Life Sciences, Piscataway, N.J. USA) configured appropriately for DsRed2 detection; 532 nm excitation laser and 580 nm BP30 emission filter, PMT=400V, 50 um pixel size resolution, and analyzed with provided Image Quant TL image analysis software. Prior to scanning, whole plant samples were removed from and rinsed of soil, arrayed on 96-well black plates (part no. 655090; Greiner Bio-One N.A.—Monroe, N.C. USA), and covered with a universal assay plate lid (Costar #3099; Corning Incorporated, Corning N.Y. USA) to immobilize and position for uniform presentation on scanner platen. Scanned image size and contrast were normalized between scans to accurately represent relative pattern of DsRed2 expression between events and test constructs.

Test vectors and controls (Table 5) represent: Native GM-HPPD promoter, deletions and mutations (SHP promoters), an H2B promoter—DsRed2 reference and untransformed wild type Col-0 control. Expression pattern and level were found to vary depending on the changes made in the HPPD promoter (Table 5 and FIG. 11).

Table 5. Observed HPPD variant promoter driven DsRed expression pattern at 3 developmental stages in transgenic *Arabidopsis* plants.

| | DsRED2 expression (+/–) | | | | | | | | | | | | | | | |
|---|---|---|---|---|---|---|---|---|---|---|---|---|---|---|---|---|
| | | Developmentat stage: | | | | | | | | | | | | | | |
| | | early vegetative (day 14) | | | | late vegetative (day 24) | | | | | | early reproductive (day 34) | | | | |
| | Organ/tissue: | rt | hctyl | ctyl | grw pt | rt | hctyl | ctyl | leaf | grw pt | vascl | rt | leaf | grw pt | sepal | vascl |
| | Test promoter description | | | | | | | | | | | | | | | |
| pVER9480 | Gm-HPPD: native HPPD promoter | – | – | + | – | – | – | + | + | – | – | – | + | – | + | – |
| pVER9481 | SHP101C: 3 TATAs deletion | – | – | – | – | – | – | – | – | – | – | – | – | – | – | – |
| pVER9483 | SHP103C: TATA3 deletion | – | – | + | – | – | – | + | + | – | – | – | + | – | + | – |
| pVER9486 | SHP106C: single nt change @ TATA1, TATA2, & TATA3 | – | – | + | – | – | – | + | + | – | – | – | + | – | + | – |
| pHD1511 | SHP101: 3 TATAs deletion + Element I | – | – | – | – | – | – | – | – | – | – | – | – | – | – | – |
| pHD1513 | SHP103: TATA3 deletion + Element I | + | – | + | – | + | – | + | + | – | – | + | + | – | + | – |
| pHD1516 | SHP106: Single nt change @ TATA1 + 2 + 3 + Element I | – | – | + | – | – | – | + | + | – | – | – | + | – | + | – |
| pHD1519 | SHP109: 3 nts change @ TATA1, 2, & 3 + Element I | – | – | + | – | – | – | + | + | – | – | – | + | – | + | – |
| pHD1505 | SHP205: Single nt change @ TATA1 & 3 + Element II | + | + | + | – | + | + | + | + | – | – | + | + | – | + | – |
| pHD1506 | SHP206: Single nt change @ TATA1, 2, & 3 + Rsyn7 Element | + | + | + | – | + | + | + | + | – | – | + | + | – | + | – |
| pVER7974 | H2B-DsRED2INT (pVER7974) | + | + | + | + | + | + | + | + | + | + | + | + | + | + | + |
| | WT Col-0 | – | – | – | – | – | – | – | – | – | – | – | – | – | – | – |

rt = root,
hctyl = hypocotyl,
cytl = cotyledon,
vascl = vascular tissue,
grw pt = growing point,
sepal = flower sepals

That which is claimed:

1. A chimeric promoter construct comprising a first polynucleotide comprising a regulatory region of a 4-hydroxyphenylpyruvate dioxygenase (HPPD) promoter operably linked to a second polynucleotide comprising a heterologous core promoter functional in a plant, wherein said regulatory region of the HPPD promoter comprises a) the polynucleotide set forth in any one of SEQ ID NO: 2, 3, 4, 11 or 20;

b) a polynucleotide comprising a fragment comprising at least 300 consecutive nucleotides of SEQ ID NO: 2, 3, 4, 11, or 20;

c) the polynucleotide set forth in any one of SEQ ID NO: 5, 6, 7, 8, 9, 10, 12, 13, 14, 15, 16, 17, 18, or 19; or d) a polynucleotide comprising a fragment comprising at least 300 consecutive nucleotides of SEQ ID NO: 5, 6, 7, 8, 9, 10, 12, 13, 14, 15, 16, 17, 18, or 19;

wherein said core promoter modulates the regulatory activity of said regulatory region of the HPPD promoter when compared to the regulatory activity of said regulatory region of the HPPD promoter alone;

wherein said chimeric promoter has transcriptional regulatory activity in a plant.

2. The chimeric promoter construct of claim 1, wherein said transcriptional regulatory activity of said regulatory region of the HPPD promoter in the absence of said core promoter comprises less than 10% of the transcriptional regulatory activity of the HPPD promoter set forth in SEQ ID NO: 1.

3. The chimeric promoter construct of claim 1, wherein said transcriptional regulatory activity of said regulatory region of the HPPD promoter in the absence of said core promoter comprises at least 10% of the regulatory activity of the HPPD promoter as set forth in SEQ ID NO: 1.

4. The chimeric promoter construct of claim 1, wherein said regulatory region of the HPPD promoter comprises a deletion selected from the group consisting of:

(a) a deletion of a TATA motif; or (b) a deletion of at least one of the TATA1, TATA2, TATA3, TATA4 or TATA5 motifs.

5. The chimeric promoter construct of claim 1, wherein said regulatory region of the HPPD promoter comprises at least one or more alterations in at least one of the TATA1, TATA2, TATA3, TATA4 or TATA5 elements.

6. The chimeric promoter construct of claim 1, wherein said core promoter increases the regulatory activity of said regulatory region of the HPPD promoter when compared to the regulatory activity of said regulatory region of the HPPD promoter alone.

7. The chimeric promoter construct of claim 1, wherein said core promoter decreases the regulatory activity of said regulatory region of the HPPD promoter when compared to the regulatory activity of said regulatory region of the HPPD promoter alone.

8. The chimeric promoter construct of claim 1, wherein said transcriptional regulatory activity of said chimeric promoter construct mimics the level of transcriptional regulatory activity of the HPPD promoter set forth SEQ ID NO:1.

9. The chimeric promoter construct of claim 1, wherein said chimeric promoter, when operably linked to a polynucleotide encoding a HPPD polypeptide having HPPD activity and insensitivity to an HPPD inhibitor, provides a sufficient level of expression of said HPPD polypeptide in a plant to impart tolerance of the plant to an HPPD inhibitor.

10. The chimeric promoter construct of claim 1, wherein said core promoter comprises a) the polynucleotide set forth in SEQ ID NO:71;

b) a polynucleotide comprising a fragment comprising at least 30 consecutive nucleotides of SEQ ID NO: 71;

c) the polynucleotide set forth in SEQ ID NO: 21; or d) the polynucleotide set forth in SEQ ID NO: 83.

11. The chimeric promoter construct of claim 10, wherein said core promoter further comprises a) a second polynucleotide as set forth in SEQ ID NO:72; or b) a second polynucleotide comprising a fragment comprising at least 20 consecutive nucleotides of SEQ ID NO: 72.

12. The chimeric promoter construct of claim 11, wherein said core promoter further comprises a) the polynucleotide set forth in SEQ ID NO:73;

b) a polynucleotide comprising a fragment comprising at least 30 consecutive nucleotides of SEQ ID NO: 73; or c) the polynucleotide set forth in SEQ ID NO: 22.

13. The chimeric promoter construct of claim 1, wherein the chimeric promoter comprises a) the sequence set forth in SEQ ID NO: 23, 24, 25, 26, 27, 28, 29, 30, 31, 32, 33, 34, 35, 36, 37, 38, 39, 40, 41, 74, 75, 76, 77, or 78; or b) a polynucleotide comprising a fragment comprising at least 300 consecutive nucleotides of SEQ ID NO: 23, 24, 25, 26, 27, 28, 29, 30, 31, 32, 33, 34, 35, 36, 37, 38, 39, 40, 41, 74, 75, 76, 77, or 78.

14. An expression cassette comprising a promoter operably linked to a polynucleotide of interest, wherein said promoter comprises the chimeric promoter construct of claim 1.

15. The expression cassette of claim 14, wherein said polynucleotide of interest encodes a polypeptide or a suppression element.

16. The expression cassette of claim 15, wherein said polynucleotide of interest encodes an HPPD polypeptide having HPPD activity and having insensitivity to an HPPD inhibitor.

17. An expression vector comprising the expression cassette claim 14.

18. A plant having stably incorporated into its genome at least one expression cassette of claim 14.

19. The plant of claim 18, wherein said plant is a dicot.

20. The plant of claim 19, wherein said dicot is soybean.

21. The plant of claim 19, wherein said dicot is *Brassica*, sunflower, cotton, or alfalfa.

22. The plant of claim 18, wherein said plant is a monocot.

23. The plant of claim 22, wherein said monocot is maize, wheat, rice, barley, sorghum, or rye.

24. A method of regulating the expression of a polynucleotide of interest, said method comprising stably incorporating in the genome of a plant or plant cell the polynucleotide sequence of interest operably linked to a promoter wherein said promoter comprises the chimeric polynucleotide of claim 1.

25. The method of claim 24, wherein said plant is a dicot.

26. The method of claim 25, wherein said dicot is soybean.

27. The method of claim 25, wherein said dicot is *Brassica*, sunflower, cotton, or alfalfa.

28. The method of claim 24, wherein said plant is a monocot.

29. The method of claim 28, wherein said monocot is maize, wheat, rice, barley, sorghum, or rye.

30. A polynucleotide comprising a promoter operably linked to a heterologous polynucleotide of interest, wherein the promoter is capable of regulating transcription of the heterologous polynucleotide of interest, wherein the promoter comprises:

(a) a nucleotide sequence comprising SEQ ID NO: 1, 2, 3, 4, 5, 6, 7, 8, 9, 10, 11, 12, 13, 14, 15, 16, 17, 18, 19, 20, 74, 75, or 76; or (b) a polynucleotide comprising a fragment comprising at least 300 consecutive nucleotides of SEQ ID NO: 1, 2, 3, 4, 5, 6, 7, 8, 9, 10, 11, 12, 13, 14, 15, 16, 17, 18, 19, 20, 74, 75, or 76, wherein said polynucleotide has transcriptional regulatory activity in a plant.

31. An expression cassette comprising a promoter operably linked to a polynucleotide of interest, wherein said promoter comprises the polynucleotide of claim 30.

32. The expression cassette of claim 31 wherein said polynucleotide of interest encodes a polypeptide or a suppression element.

33. The expression cassette of claim 31, wherein said polynucleotide of interest encodes an HPPD polypeptide having HPPD activity and having insensitivity to an HPPD inhibitor.

34. An expression vector comprising the expression cassette of claim 31.

35. A plant having stably incorporated into its genome at least one expression cassette comprising a polynucleotide of interest operably linked to a promoter, wherein said promoter comprises the polynucleotide of claim 30.

36. The plant of claim 35, wherein said plant is a dicot.

37. The plant of claim 36, wherein said dicot is soybean.

38. The plant of claim 36, wherein said dicot is *Brassica*, sunflower, cotton, or alfalfa.

39. The plant of claim 35, wherein said plant is a monocot.

40. The plant of claim 39, wherein said monocot is maize, wheat, rice, barley, sorghum, or rye.

41. A method of expressing a polynucleotide of interest, said method comprising stably incorporating in the genome of a plant or plant cell the polynucleotide of interest operably linked to a promoter, wherein said promoter comprises the polynucleotide of claim 30.

42. The method of claim 41, wherein said plant is a dicot.

43. The method of claim 42, wherein said dicot is soybean.

44. The method of claim 42, wherein said dicot is *Brassica*, sunflower, cotton, or alfalfa.

45. The method of claim 41, wherein said plant is a monocot.

46. The method of claim 45, wherein said monocot is maize, wheat, rice, barley, sorghum, or rye.

* * * * *